(12) United States Patent
Dewey et al.

(10) Patent No.: US 10,347,359 B2
(45) Date of Patent: Jul. 9, 2019

(54) METHOD AND SYSTEM FOR NETWORK MODELING TO ENLARGE THE SEARCH SPACE OF CANDIDATE GENES FOR DISEASES

(75) Inventors: Frederick E. Dewey, Redwood City, CA (US); Euan A. Ashley, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 710 days.

(21) Appl. No.: 13/526,317

(22) Filed: Jun. 18, 2012

(65) Prior Publication Data
US 2013/0090908 A1    Apr. 11, 2013

Related U.S. Application Data

(60) Provisional application No. 61/497,542, filed on Jun. 16, 2011.

(51) Int. Cl.
*G01N 33/48* (2006.01)
*G16B 5/00* (2019.01)

(52) U.S. Cl.
CPC ...................... *G16B 5/00* (2019.02)

(58) Field of Classification Search
CPC ............ C12Q 1/6883; C12Q 2565/627; C12Q 1/6886; G01N 2500/00; G01N 33/5023; G01N 33/5082
See application file for complete search history.

(56) References Cited

U.S. PATENT DOCUMENTS

| | | |
|---|---|---|
| 7,493,253 B1 | 2/2009 | Ceusters et al. |
| 7,953,593 B2 | 5/2011 | Marchisio et al. |
| 8,050,870 B2 | 11/2011 | Heckerman et al. |
| 8,321,196 B2 | 11/2012 | Hale et al. |
| 8,433,715 B1 | 4/2013 | Mirhaji |
| 2006/0074836 A1 | 4/2006 | Gardner et al. |
| 2008/0162541 A1 | 7/2008 | Oresic et al. |
| 2009/0012842 A1 | 1/2009 | Srinivasan et al. |
| 2011/0087670 A1 | 4/2011 | Jorstad et al. |
| 2012/0011170 A1 | 1/2012 | Elad et al. |
| 2012/0290288 A1 | 11/2012 | Aït-Mokhtar |
| 2013/0073217 A1 | 3/2013 | Dewey et al. |
| 2013/0073571 A1 | 3/2013 | Coulet et al. |
| 2013/0080069 A1 | 3/2013 | Cordero et al. |
| 2013/0080365 A1 | 3/2013 | Dewey et al. |
| 2013/0090909 A1 | 4/2013 | Dudley et al. |
| 2014/0088942 A1 | 3/2014 | Li |
| 2015/0370959 A9 | 12/2015 | Dewey et al. |

(Continued)

OTHER PUBLICATIONS

US 9,443,056 B2, 09/2016, Dewey et al. (withdrawn)

(Continued)

*Primary Examiner* — Larry D Riggs, II
(74) *Attorney, Agent, or Firm* — KPPB LLP

(57) ABSTRACT

With the advent of low cost, high-throughput whole genome sequencing ("next generation sequencing"), tools are available to assay human genetic variation contributing to inherited disease syndromes. A method is disclosed for prioritization of genetic variants, and identification of disease genes, using network modeling of gene associations.

21 Claims, 43 Drawing Sheets

(56) References Cited

U.S. PATENT DOCUMENTS

2015/0370963 A9  12/2015  Dewey et al.

OTHER PUBLICATIONS

Ruan et al. (a general co-expression network-based approach to gene expression analysis: comparison and applications; BMC Systems Biology 2010, 4:8).*

Mao et al. (*Arabidopsis* gene co-expression network and its functional modules; BMC Bioinformatics, 2009, 10:346).*

Kumar et al., "Predicting the effects of coding non-synonymous variants on protein function using the SIFT algorithm", Nature Protocols, 2009, vol. 4, No. 8, 1073-1082.

Kuwahara et al., "NRSF regulates the fetal cardiac gene program and maintains normal cardiac structure and function", Embo Journal, 2003, vol. 22, No. 23, pp. 6310-6321.

Langfelder et al., "Defining clusters from a hierarchical cluster tree: the Dynamic Tree Cut package for R", Bioinformatics, 2008, vol. 24, No. 5, 719-720.

Langfelder et al., "Eigengene networks for studying the relationships between co-expression modules", BMC Syst. Biol., 2007, pp. 1-54, doi:10.1186/1752-0509.

Levy et al., "Identification of transcription factor binding sites in the human genome sequence", Mammalian Genome, 2002, vol. 13, pp. 510-514, DOI:10.1007/s003350010117.

Li et al., "Fast and accurate short read alignment with Burrows-Wheeler transform", Bioinformatics, May 18, 2009, vol. 25, No. 14, pp. 1754-1760.

Lyn et al., "Gene expression profile in mouse myocardium after ischemia", Physiol Genomics, 2000, vol. 2, pp. 93-100.

Macaya et al., "A synonymous mutation in TCOF1 causes Treacher Collins syndrome due to mis-splicing of a constitutive exon", American Journal of Medical Genetics Part A, Feb. 24, 2009, vol. 149A, pp. 1624-1627.

Marchini et al., "A new multipoint method for genome-wide association studies by imputation of genotypes", Nature Genetics, Jul. 2007, vol. 39, No. 7, pp. 906-913.

Margaglione et al., "The methylenetetrahydrofolate reductase TT677 genotype is associated with venous thrombosis independently of the coexistence of the FV Leiden and the prothrombin A20210 mutation", Thromb Haemost, 1998, vol. 79, pp. 907-911.

Matkovich et al., "Reciprocal regulation of myocardial microRNAs and messenger RNA in human cardiomyopathy and reversal of the microRNA signature by biomechanical support", Circulation, Mar. 10, 2009; vol. 119, pp. 1263-1271.

Morgan et al., "Likelihood ratios for genome medicine", Genome Medicine, 2010, vol. 2, No. 30, 5 pgs.

Myers et al., "Drive against hotspot motifs in primates implicates the PRDM9 gene in meiotic recombination", Science, Feb. 12, 2010, vol. 327, 876-879.

Nachman et al., "Estimate of the Mutation Rate per Nucelotide in Humans", Genetics, Sep. 2000, vol. 156, pp. 297-304.

Nakamura et al., "The mediator complex subunit 1 enhances transcription of genes needed for adrenal androgen production", General Endocrinology, Sep. 2009, vol. 150, No. 9, pp. 4145-4153.

Nelson et al., "The Population Reference Sample, POPRES: a resource for population, disease, and pharmacological genetics research", The American Journal of Human Genetics, Sep. 12, 2008, vol. 83, pp. 347-358.

Ng et al., "Accounting for Human Polymorphisms Predicted to Affect Protein Function", Genome Research, 2002, vol. 12, pp. 436-446.

Ng et al., "Predicting the Effects of Amino Acid Substitutions on Protein Function", Annu. Rev. Genomics Hum. Genet., 2006, vol. 7, pp. 61-80.

Ng et al., "SIFT: Predicting amino acid changes that affect protein function", Nucleic Acids Research, Feb. 28, 2003, vol. 31, No. 13, pp. 3812-3814.

Nowell et al., "Pharmacogenetics of human cytosolic sulfotransferases", Oncogene, 2006, vol. 25, pp. 1673-1678.

Oldham et al., "Conservation and evolution of gene coexpression networks in human and chimpanzee brains", Proc Natl Acad Sci U S A, Nov. 21, 2006, vol. 103, No. 47, pp. 17973-17978.

Ormond et al., "Challenges in the clinical application of whole-genome sequencing", Lancet, May 15, 2010, vol. 375, 1749-1751.

Paigen et al., "The recombinational anatomy of a mouse chromosome", PLoS Genettics, Jul. 2008, vol. 4, Issue 7, e1000119, 15 pgs., doi: 10.1371/journal.pgen.1000119.

Parvanov et al., "Prdm9 controls activation of mammalian recombination hotspots", Science, Feb. 12, 2010, vol. 327, vol. 5967: 835; 4 pgs., doi:10.1126/science.1181495.

Petkov et al., "Crossover interference underlies sex differences in recombination rates", Trends in Genetics, Oct. 26, 2007, vol. 23, No. 11, 539-542.

Price et al., "Principal components analysis corrects for stratification in genome-wide associate studies", Nature Genetics, Aug. 2006, vol. 38, No. 8, pp. 904-909.

Pruitt et al., "NCBI reference sequences (RefSeq): a curated non-redundant sequence database of genomes, transcripts and proteins", Nucleic Acids Res, vol. 35, 2007, D61-65, doi:10.1093/nar/gkl842.

Purcell et al., "PLINK: A Tool Set for Whole-Genome Association and Population-Based Linkage Analyses", The American Journal of Human Genetics, Sep. 2007, vol. 81, pp. 559-575.

Rajabi et al., "Return to the fetal gene program protects the stressed heart: a strong hypothesis", Heart Fail Rev., 2007, vol. 12, pp. 331-343.

Ramensky et al., "Human non-synonymous SNPs: server and survey", Nucleic Acids Research, 2002, vol. 30, No. 17, pp. 3894-3900.

Ridker et al., "Interrelation of hyperhomocyst(e)inemia, factor V Leiden, and risk of future venous thromboembolism", Circulation, 1997, vol. 95, pp. 1777-1782.

Ridker et al., "Mutation in the gene coding for coagulation factor V and the risk of myocardial infarction, stroke, and venous thrombosis in apparently healthy men", The New England Journal of Medicine, Apr. 6, 1995, vol. 332, pp. 912-917.

Rivas et al., "Secondary structure alone is generally not statistically significant for the detection of noncoding RNAs", Bioinformatics, 2000; vol. 16, No. 7, pp. 583-605.

Roach et al., "Analysis of genetic inheritance in a family quartet by whole-genome sequencing", Science, Apr. 30, 2010, vol. 328, pp. 636-639.

Roemisch et al., "The frequent Marburg I polymorphism impairs the pro-urokinase activating potency of the factor VII activating protease (FSAP)", Blood Coagulation and Fibrinolysis, Apr. 3, 2002, vol. 13, No. 5, pp. 433-441.

Schadt, "Molecular networks as sensors and drivers of common human diseases", Nature, Sep. 10, 2009, vol. 461, pp. 218-223.

Sedding et al., "The G534E polymorphism of the gene encoding the factor VII-activating protease is associated with cardiovascular risk due to increased neointima formation", J Exp Med, Dec. 25, 2006, vol. 203, No. 13, pp. 2801-2807.

Shendure et al., "Next-generation DNA sequencing", Nature Biotechnology, Oct. 2008, vol. 26, No. 10, 1135-1145.

Smith et al., "Mutations in ATP6N1B, encoding a new kidney vacuolar proton pump 116-kD subunit, cause recessive distal renal tubular acidosis with preserved hearing", Nature Genetics, Sep. 2000, vol. 26, pp. 71-75.

Storey et al., "Statistical methods for identifying differentially expressed genes in DNA microarrays", Methods Mol Biol., 2003, vol. 224, pp. 149-157.

Sunyaev et al., "PSIC: profile extraction from sequence alignments with position-specific counts of independent observations", Protein Engineering, 1999, vol. 12, No. 5, pp. 387-394.

Tajima et al., "Estimation of Evolutionary Distance between Nucleotide Sequences", Molecular Biology and Evolution, 1984, vol. 1, No. 3, pp. 269-285.

Thattaliyath et al., "HAND1 and HAND2 are expressed in the adult-rodent heart and are modulated during cardiac hypertrophy", Biochem Biophys Res Commun., 2002, vol. 297, pp. 870-875.

(56) References Cited

OTHER PUBLICATIONS

Thum et al., "MicroRNAs in the human heart: a clue to fetal gene reprogramming in heart failure", Circulation, Jul. 17, 2007, vol. 116, pp. 258-267.
Trivedi et al., "Hdac2 regulates the cardiac hypertrophic response by modulating Gsk3β activity", Nat Med., Mar. 2007, vol. 13, No. 3, pp. 324-331.
Van Rooij et al., "A signature pattern of stress-responsive microRNAs that can evoke cardiac hypertrophy and heart failure", Proc Natl Acad Sci USA, Nov. 28, 2006, vol. 103, No. 48, pp. 18255-18260.
Vanderheyden et al., "Myocardial gene expression in heart failure patients treated with cardiac resynchronization therapy: responders versus nonresponders", J Am Coll Cardiol., 2008, vol. 51, No. 2, pp. 129-136.
Vasen et al., "New Clinical Criteria for Hereditary Nonpolyposis Colorectal Cancer (HNPCC, Lynch Syndrome) Proposed by the International Collaborative Group on HNPCC", Gastroenterology, 1999, vol. 116, pp. 1453-1456.
Watterson, "On the number of segregating sites in genetical models without recombination", Theor Popul Biol, 1975, vol. 7, pp. 256-276.
Wheeler et al., "The complete genome of an individual by massively parallel DNA sequencing", Nature, Apr. 17, 2008, vol. 452, pp. 872-877.
Williams et al., "Rapid haplotype inference for nuclear families", Genome Biology, 2010, vol. 11, 17 pgs.
Wingender et al., "TRANSFAC: a database on transcription factors and their DNA binding sites", Nucleic Acids Res, 1996, vol. 24, No. 1, pp. 238-241.
Yang et al., "Validation of candidate causal genes for obesity that affect shared metabolic pathways and networks", Nat Genet., Apr. 2009, vol. 41, No. 4, 415-423.
Yeo et al., "Maximum entropy modeling of short sequence motifs with applications to RNA splicing signals", J Comput Biol., Feb. 2004, vol. 11 No. 2-3, pp. 377-394.
Yip et al., "Gene network interconnectedness and the generalized topological overlap measure", BMC Bioinformatics, Jan. 24, 2007, vol. 8, No. 22, 14 pgs.
Yue et al., "Post-infarction heart failure in the rat is associated with distinct alterations in cardiac myocyte molecular phenotype", J Mol Cell Cardiol., 1998, vol. 30, pp. 1615-1630.
Zhang et al., "A general framework for weighted gene co-expression network analysis", Stat Appl Genet Mol Biol., 2005, vol. 4, Article 17, 11 pages.
Zhang et al., "Generic Algorithm to Predict the Speed of Translational Elongation: Implications for Protein Biogenesis", PLoS One, Apr. 2009, vol. 4, Issue 4, e5036. doi: 1 0.1371/journal.pone.0005036, 9 pages.
Abecasis et al., "Merline—rapid analysis of dense genetic maps using sparse gene flow trees", Nature Genetics, Jan. 2002, vol. 30, pp. 97-101.
Adzhubei et al., "A method and server for predicting damaging missense mutations", Nat Methods, vol. 7, No. 4, Apr. 2010, 248-249.
Alexiou et al., "Lost in translation: an assessment and perspective for computational microRNA target identification", Bioinformatics, vol. 25, No. 23, 2009; pp. 3049-3055.
Ashley et al., "Clinical evaluation incorporating a personal genome", Lancet vol. 375, May 1, 2010, pp. 1525-1535; doi:10.1016/S0140-6736(10)60452-7.
Barabasi et al., "Emergence of Scaling in Random Networks", Science, vol. 286, Oct. 15, 1999, pp. 509-512.
Barbacioru et al., "Effect of various normalization methods on Applied Biosystems expression array system data", BMC Bioinformatics, vol. 7, No. 533, Dec. 15, 2006, 14 pgs.
Baudat et al., "PRDM9 is a major determinant of meiotic recombination hotspots in humans and mice", Science, vol. 327, 2010, pp. 836-840.

Bentley et al., "Accurate whole human genome sequencing using reversible terminator chemistry", Nature, Articles, Nov. 6, 2008, vol. 456, pp. 53-59.
Bezemer et al., "No association between the common MTHFR 677C->T polymorphism and venous thrombosis: results from the MEGA study", Arch Intern Med, vol. 167, Mar. 12, 2007, pp. 497-501.
Bodenreider, "The Unified Medical Language System (UMLS): integrating biomedical terminology", Nucleic Acids Research, Database issue, 2004, vol. 32 pp. D267-D270.
Broman et al., "Comprehensive human genetic maps: individual and sex-specific variation in recombination", Am. J. Hum. Genet., vol. 63, Aug. 7, 1998, pp. 861-869.
Candore et al., "Pharmacogenomics: A Tool to Prevent and Cure Coronary Heart Disease", Current Pharmaceutical Design, 2007, vol. 13, pp. 3726-3734.
Chamary et al., "Hearing silence: non-neutral evolution at synonymous sites in mammals", Nature Reviews Genetics, Feb. 2006, vol. 7, pp. 98-108.
Chen et al., "-717A>G polymorphism of human C-reactive protein gene associated with coronary heart disease in ethnic Han Chinese: the Beijing atherosclerosis study", Journal of Molecular Medicine, vol. 83, 2005, pp. 72-78.
Chen et al., "The reference human genome demonstrates high risk of type 1 diabetes and other disorders", Pac Symp Biocomput, 2011, 231-242.
Chen et al., "Variations in DNA elucidate molecular networks that cause disease", Nature, 2008, vol. 452, pp. 429-435; doi:10.1038/nature06757.
Chien, "Stress pathways and heart failure", Cell, Sep. 3, 1999, vol. 98, pp. 555-558.
Coffer et al., "Forkhead-box transcription factors and their role in the immune system", Nat Rev Immunology, Nov. 2004, vol. 4, pp. 889-899.
De Bakker et al., "A high-resolution HLA and SNP haplotype map for disease association studies in the extended human MHC", Nat Genet 38, Oct. 2006, vol. 38, No. 10, pp. 1166-1172.
Dennis et al., "DAVID: Database for Annotation, Visualization, and Integrated Discovery", Genome Biology, 2003, 4:R60, 11 pgs.
Dewey et al., "Phased Whole-Genome Genetic Risk in a Family Quartet Using a Major Allele Reference Sequence", PLoS Genetics, Sep. 2011, vol. 7, Issue 9, 15 pgs.
Donnelly, "The Probability that Related Individuals Share Some Section of Genome Identical by Descent", Theoretical Population Biology, 1983, vol. 23, pp. 34-63.
Durbin et al., "A map of human genome variation from population-scale sequencing", Nature, vol. 467, Oct. 28, 2010, pp. 1061-1073.
Eyre-Walker, "An analysis of codon usage in mammals: selection or mutation bias?", J. Mol. Evol., 1991, vol. 33, pp. 442-449.
Fan et al., "Noninvasive diagnosis of fetal aneuploidy by shotgun sequencing DNA from maternal blood", Proceedings of the National Academy of Sciences USA, Oct. 21, 2008, vol. 105, No. 42, pp. 16266-16271.
Feldman et al., "Selective changes in cardiac gene expression during compensated hypertrophy and the transition to cardiac decompensation in rats with chronic aortic banding", Circ Res., Jul. 1993, vol. 73, No. 1, pp. 184-192.
Fitch, "Toward Defining the Course of Evolution: Minimum Change for a Specific Tree Topology", Systematic Zoology, Dec. 1971, vol. 20, No. 4, pp. 406-416.
Gaur et al., "The heart of metamorphosing Mexican axolotl but not that of the cardiac mutant is associated with the upregulation of Hox A5", Biochemical and Biophysical Research Communications, 1998, vol. 245, Article No. RC988514, pp. 746-751.
Grier et al., "Quantification of Hox and surfactant protein-B transcription during murine lung development", Neonatology, 2009, vol. 96, pp. 50-60.
Grinberg et al., "The ZIC gene family in development and disease", Clinical Genetics, 2005, vol. 67, pp. 290-296.
Hamosh et al., "Online Mendelian Inheritance in Man (OMIM) a knowledgebase of human genes and genetic disorders", Nucleic Acids Research, 2002, vol. 30, pp. 52-55.

(56) References Cited

OTHER PUBLICATIONS

Hannenhalli et al., "Transcriptional genomics associates FOX transcription factors with human heart failure", Circulation, Sep. 19, 2006, vol. 114, pp. 1269-1276.
Hansson et al., "A switch in metabolism precedes increased mitochondrial biogenesis in respiratory chain-deficient mouse hearts", Proc Natl Acad Sci U S A, Mar. 2, 2004; vol. 101, No. 9, pp. 3136-3141.
Hidaka et al., "Differentiation of Pharyngeal Endoderm from Mouse Embryonic Stem Cell", Stem Cells and Development, 2010, vol. 19, No. 11, pp. 1735-1743.
Hofacker, "Vienna RNA secondary structure server", Nuc. Acid Res., 2003, vol. 31, No. 13, pp. 3429-3431.
Hoppe et al., "Marburg I polymorphism of factor VII-activating protease is associated with idiopathic venous thromboembolism", Blood, Feb. 15, 2005, vol. 105, No. 4, pp. 1549-1551.
Horvath et al., "Geometric interpretation of gene coexpression network analysis", PLoS Comput. Biol., Aug. 2008, vol. 4, Issue 8; 4:e1000117, 27 pgs.
Hoshijima et al., "Mixed signals in heart failure: cancer rules", J. Clin. Invest., 2002, vol. 109, No. 7, pp. 849-855.
Hu et al., "VisANT 3.5: multiscale network visualization, analysis and inference based on the gene ontology", Nucleic Acids Res., May 21, 2009, vol. 37, Web Server Issue, pp. W115-W121.
Huang et al., "Systematic and integrative analysis of large gene lists using DAVID bioinformatics resources", Nature Protocols, 2009, vol. 4, No. 1, pp. 44-57.
Ikemura, "Codon usage and tRNA content in unicellular and multicellular organisms", Mol. Biol. Evol., 1985, vol. 2, pp. 13-34.
Jeong et al., "Lethality and centrality in protein networks", Nature, May 3, 2001, vol. 411, pp. 41-42.
Jeong et al., "The large-scale organization of metabolic networks", Nature, Oct. 5, 2000, vol. 407, pp. 651-654.
Jhund et al., "Long-term trends in first hospitalization for heart failure and subsequent survival between 1986 and 2003: a population study of 5.1 million people", Circulation, Feb. 3, 2009, vol. 119, pp. 515-523.
Johnson et al., "SNAP: a web-based tool for identification and annotation of proxy SNPs using HapMap", Bioinformatics, Oct. 30, 2008, vol. 24, No. 24, pp. 2938-2939.
Kim et al., "Hoxa-5 in mouse developing lung: cell-specific expression and retinoic acid regulation", Am J Physiol Lung Cell Mol Physiol, 2000; vol. 279, pp. L863-L871.
Kimchi-Sarfaty et al., "A "Silent" Polymorphism in the MDR1 Gene Changes Substrate Specificity", Science, Jan. 26, 2007; vol. 315, No. 5811, pp. 525-528.
Kimura, "Evolutionary rate at the molecular level", Nature, vol. 217, Feb. 17, 1968, pp. 624-626.
Klein et al., "Estimation of the warfarin dose with clinical and pharmacogenetic data", New England Journal of Medicine, Feb. 19, 2009, vol. 360, No. 8, pp. 753-764.
Kong et al., "Fine-scale recombination rate differences between sexes, populations and individuals", Nature, vol. 467, Oct. 28, 2010, pp. 1099-1103.
Kong et al., "Parental origin of sequence variants associated with complex diseases", Nature, Dec. 17, 2009, vol. 462, No. 7275, pp. 868-874.
Kong et al., "Sequence variants in the RNF212 gene associate with genome-wide recombination rate", Science, Mar. 7, 2008, vol. 319, pp. 1398-1401.
Koster et al., "Venous thrombosis due to poor anticoagulant response to activated protein C: Leiden Thrombophilia Study", Lancet, Dec. 18/25, 1993, vol. 342, pp. 1503-1506.
Kruglyak et al., "Parametric and Nonparametric Linkage Analysis: A Unified Multipoint Approach", Am. J. Hum. Genet., 1996, vol. 58, pp. 1347-1363.
Kujovich, "Factor V Leiden thrombophilia", Genetics in Medicine, Jan. 2011, vol. 13, No. 1, pp. 1-16.
Kumar et al., "MEGA3: Integrated software for Molecular Evolutionary Genetics Analysis and sequence alignment", Briefings in Bioinformatics, Jun. 2004, vol. 5, No. 2, pp. 150-163.
Kumar et al., "Positional conservation and amino acids shape the correct diagnosis and population frequencies of benign and damaging personal amino acid mutations", Genome Research, 2009, vol. 19, pp. 1562-1569.
*Ameritox, Ltd.* v. *Millennium Health, LLC*, No. 13-cv-832-wmc (W.D. Wis. 2015).
*Cal. Inst. of Tech.* v. *Hughes Communs., Inc.*, 2014 U.S. Dist. Lexis 156763 (C.D. Cal. Nov. 3, 2014).
*Cybersource Corporation*, v. *Retail Decisions, Inc.*, 654 F.3d 1366 (Fed. Cir. 2011).
Cytoscape 2.6.2, Cytoscape Consortium, May 12, 2009, Retrieved from: https://web.archive.org/web/20090512221703/http://cytoscape.org/, 7 pgs.
*DDR Holdings, LLC* v. *Hotels.com, L.P*, 773 F.3d 1245, 1257 (Fed. Cir. 2014).
*Messaging Gateway Solutions, LLC* v. *Amdocs, Inc. and Amdocs Limited*, Civil Action No. 14-732-RGA (D. Del. 2015).
*Smartflash LLC* v. *Apple Inc.*, Case No. 6:13-CV-447-JRG-KNM (E.D. Tex. 2015).
*Smartgene, Inc.*, v. *Advanced Biological Laboratories, SA, and ABL Patent Licensing Technologies, SARL*, (Fed. Cir. 2014).
Dewey, et a;., "Supplementary materials and method for Phased Whole-Genome Genetic Risk in a Family Quartet Using a Major Allele Reference Sequence", PLOS Genetics, Published Sep. 15, 2011, Retrieved from: https://doi.org/10.1371/journal.pgen.1002280.s017, 27 pages.
*Ultramercial, Inc.* v. *Hulu, LLC,* No. 2010-1544 (Fed. Cir. Nov. 14, 2014).
"A Catalog of Published Genome-Wide Association Studies", Retrieved from: https://web.archive.org/web/20110727063625/http://www.genome.gov/gwastudies/, Jul. 27, 2011, Printed on Jun. 19, 2017, 3 pages.
"Genome-wide association study of 14,000 cases of seven common diseases and 3,000 shared controls", The Wellcome Trust Case Control Consortium, Nature, vol. 447, pp. 661-678, Jun. 7, 2007.
The International HapMap 3 Consortium, "Integrating common and rare genetic variation in diverse human populations", Nature, 467(7311), Sep. 2, 2010, pp. 52-58; doi:10.1038/nature09298.
Abi-Haidar et al., "Uncovering protein interaction in abstracts and text using a novel linear model and word proximity networks", Genome Biology 9 (Suppl 2):S11, Sep. 1, 2008, 19 pgs.
Agarwal et al., "Genetics of human hypertension", Trends Endocrinology & Metabolism, vol. 16, Issue No. 3, pp. 127-133, Apr. 2005.
Agichtein et al., "Snowball: Extracting Relations from Large Plain-Text Collections", In: ACM DL; Jan. 1, 2000, pp. 85-94.
Ahlers et al., "Extracting semantic predications from Medline citations for pharmacogenomics", In: Pacific Symposium on Biocomputing; Jan. 3-7, 2007, pp. 209-220.
Ahn et al., "Link Communities Reveal Multiscale Complexity in Networks", Nature, 466, Aug. 5, 2010, pp. 761-764+1.
Akashi et al., "Translational selection and molecular evolution", Current Opinion in Genetics & Development, Dec. 1998; vol. 8, Issue 6, 688-693.
Alex et al., "Automating curation using a natural language processing pipeline", Genome Biology 9 (Suppl 2):S10, Sep. 1, 2008, 14 pgs.
Altman et al., "Text mining for biology—the way forward: opinions from leading scientists", Genome Biology 9 (Suppl 2):S7, Sep. 1, 2008, 15 pgs.
Arvanitis et al., "The Ser96Ala variant in histidine-rich calcium-binding protein is associated with life-threatening ventricular arrhythmias in idiopathic dilated cardiomyopathy", European Heart Journal, Aug. 2008, vol. 29, pp. 2514-2525.
Ashley et al., "Clinical assessment incorporating a personal genome", Lancet, May 1, 2010, vol. 375, Issue 9725, pp. 1525-1535.
Aten et al., "Using genetic markers to orient the edged in quantitative trait network: The NEO software", BMV Systems Biology, Apr. 15, 2008, vol. 2, No. 34, 21 pgs.

(56) References Cited

OTHER PUBLICATIONS

Aussenac-Gilles et al., "Text analysis for ontology and terminology engineering", Applied Ontology, Jan. 2005; vol. 1, Issue 1, pp. 35-46.
Baader et al., "The description logic handbook", Cambridge University Press; 2003, 574 pgs.
Barreiro et al., "Natural selection has driven population differentiation in modern humans", Nature Genetics, 40(3), pp. 340-345, Mar. 2008.
Baumgartner Jr. et al., "Concept recognition for extracting protein interaction relations from biomedical text", Genome Biology 9(Suppl 2):S9, Sep. 1, 2008, 15 pgs.
Bell et al., "Carrier Testing for Severe Childhood Recessive Diseases by Next-Generation Sequencing", Science Translational Medicine, vol. 3: 65ra4, Jan. 12, 2011, 26 pgs.
Berrebi-Bertrand et al., "Biophysical interaction between phospholamban and protein phosphatase 1 regulatory subunit GM", FEBS Letters, Nov. 20, 1998, vol. 439, pp. 224-230.
Percha, Bethany, "Discovering New Drug-Drug Interactions by Text-Mining the Biomedical Literature", Department of Biomedical Informatics, Stanford University, Stanford, CA, Winter 2011, 7 pgs.
Blaschke et al., "Automatic extraction of biological information from scientific text: protein-protein interactions", In: ISMB; Feb. 1999, pp. 60-67.
Blekhman et al., "Natural selection on genes that underlie human disease susceptibility", Curr Biol, 18(2):883-889, Jun. 24, 2008.
Bloss et al., "Effect of Direct-to-Consumer Genomewide Profiling to Assess Disease Risk", The New England Journal of Medicine, vol. 364, Feb. 10, 2011, pp. 524-534.
Bodmer et al., "Common and rare variants in multifactorial susceptibility to common diseases", Nature Genetics, 40(6): 695-701, Jun. 2008; published online May 29, 2008.
Boyle et al., "Annotation of functional variation in personal genomes using RegulomeDB", Genome Research 22:1790-1797, Sep. 2012.
Brennan et al., "A mechanism for the HLA-A*01—associated risk for EBV Hodgkin lymphoma and infectious mononucleosis", Blood, vol. 112, No. 6, Sep. 15, 2008, pp. 2589-2590.
Buitelaar et al., "Ontology learning from text: methods, evaluation and applications", vol. 123 of Frontiers in Artificial Intelligence and Applications, IOS Press; Jul. 1, 2005, 4 pgs.
Cai et al., "Similarly strong purifying selection acts on human disease genes of all evolutionary ages", Genome Biol Evol., 1:131-44, May 27, 2009.
Chanock et al., "Replicating genotypephenotype associations", NCI-NHGRI Working Group on Replication in Association Studies, Nature, vol. 447, Jun. 7, 2007, 6 pgs.
Chatr-Aryamontri et al., "MINT and IntAct contribute to the Second BioCreative challenge: serving the text-mining community with high quality molecular interaction data", Genome Biology 9(Suppl 2):55, Sep. 1, 2008, 8 pgs.
Chen et al., "Non-synonymous and Synonymous Coding SNPs Show Similar Likelihood and Effect Size of Human Disease Association", PLoS One, vol. 5, Issue 10, Oct. 22, 2010, e13574-1-e13574-6.
Ciaramita et al., "Unsupervised learning of semantic relations between concepts of a molecular biology ontology", in: IJCAI; Jul. 30-Aug. 5, 2005, pp. 659-664.
Cilibrasi et al., "Automatic meaning discovery using Google", In: Kolmogorov complexity and applications; 2006, 31 pgs.
Cohen et al., "Empirical distributional semantics: methods and biomedical applications", Journal of Biomedical Informatics, Apr. 2009; vol. 42, No. 2, pp. 390-405; available online Feb. 14, 2009.
Coop et al., "High-resolution mapping of crossovers reveals extensive variation in fine-scale recombination patterns among humans", Science, vol. 319, 1395-1398, Mar. 7, 2008.
Cooper et al., "A genome-wide scan for common genetic variants with a large influence on warfarin maintenance dose", Blood, Aug. 15, 2008, vol. 112, No. 4, pp. 1022-1027.
Cooper et al., "Distribution and intensity of constraint in mammalian genomic sequence", Genome Research, vol. 15, No. 7, Jun. 2005, pp. 901-913.
Cooper et al., "Single-nucleotide evolutionary constraint scores highlight disease-causing mutations", Nature Methods, vol. 7, No. 4, Apr. 2010, pp. 250-251.
Cordero et al., "A Community Overlap Strategy Reveals Central Genes and Networks in Heart Failure", bioRxiv preprint first posted online Jan. 28, 2016; doi: http://dx.doi.org/10.1101/038174, 52 pgs.
Coulet et al., "Integration and publication of heterogeneous text-mined relationships on the Semantic Web", Bio-Ontologies 2010: Semantic Applications in Life Sciences Boston, MA, Jul. 2010, 16 pgs.
Coulet et al., "Suggested ontology for pharmacogenomics (SO-pharm): modular construction and preliminary testing", In: KSinBIT; 2006, LNCS 4277, pp. 648-657.
Li et al., "Building disease-specific drug-protein connectivity maps from molecular interaction networks and pubmed abstracts", PLoS Computational Biology, Jul. 31, 2009; 5(7):e1000450, 15 pgs.
Lo et al., "Developmental regulation and cellular distribution of human cytosolic malate dehydrogenase (MDH1)", Journal of Cellular Biochemistry, 2005, vol. 94, pp. 763-773, first published Nov. 24, 2004.
Lohmueller et al., "Proportionally more deleterious genetic variation in European than in African populations", Nature, Letters, Feb. 21, 2008, vol. 451, pp. 994-997.
Manolio et al., "Finding the missing heritability of complex diseases", Nature, vol. 461, No. 7265, Oct. 8, 2009, pp. 747-753.
McClellan et al., "Genetic heterogeneity in human disease", Cell, vol. 141, Issue No. 2, pp. 210-217, Apr. 16, 2010.
McKenna et al., "The Genome Analysis Toolkit: A MapReduce framework for analyzing next-generation DNA sequencing data", Genome Research, vol. 20, Jul. 12, 2010, pp. 1297-1303.
Morgan et al., "Overview of BioCreative II gene normalization", Genome Biology 9(Suppl 2):S3, Sep. 1, 2008, pp. S1-S1-19.
Ng et al., "Predicting Deleterious Amino Acid Substitutions", Genome Res., Mar. 13, 2001, vol. 11, No. 5, pp. 863-874.
Nicolaou et al., "Role of protein phosphatase-1 inhibitor-1 in cardiac physiology and pathophysiology", J. Mol. Cell Cardiol, Sep. 2009, vol. 47, No. 3, pp. 365-371.
Ounissi-Benkalha et al., "The molecular genetics of type 1 diabetes: new genes and emerging mechanisms", Trends, Molecular Medicine, 14, pp. 268-275, Jun. 2008.
Park et al., "Estimation of effect size distribution from genome-wide association studies and implications for future discoveries", Nature Genetics, 42, pp. 570-575, Jul. 2010.
Patel et al., "An Environment-Wide Association Study (EWAS) on Type 2 Diabetes Mellitus", PLoS One 5(5): e10746, May 20, 2010, 10 pgs.
Poulsen et al., "Heritability of type II (non-insulin-dependent) diabetes mellitus and abnormal glucose tolerance—a population-based twin study", Diabetologia, 42(2):139-145, Feb. 1999, published online Aug. 10, 2009.
Pushkarev et al., "Single-molecule sequencing of an individual human genome", Nature Biotech., Sep. 2009, vol. 27, No. 9, pp. 847-850, doi: 10.1038/nbt.1561.
Rasmussen et al., "Ancient human genome sequence of an extinct Palaeo-Eskimo", Nature, Feb. 11, 2010, vol. 463, pp. 757-762.
Ridker et al., "Interrelation of hyperhomocyst(e)inemia, factor V Leiden, and risk of future venous thromboembolism", Circulation 95, pp. 1777-1782, Apr. 1, 1997.
Rinaldi et al., "OntoGene in BioCreative II", Genome Biology 9(Suppl 2):S13, Sep. 1, 2008, pp. S2-S13.
Rindflesch et al., "Semantic relations asserting the etiology of genetic diseases", In: AMIA Annu. Symp. Proc. 2003; Feb. 2003, pp. 554-558.
Ripatti et al., "A multilocus genetic risk score for coronary heart disease: case-control and prospective cohort analyses", Lancet, vol. 376, No. 9750, Oct. 23, 2010, pp. 1393-1400.
Roberts, "Germlike gain-of-function mutations in SOS1 cause Noonan syndrome", Nature Genetics, 2007, vol. 39, pp. 70-74, published online Dec. 3, 2006.

(56) References Cited

OTHER PUBLICATIONS

Rogers et al., "Radial styloid impingement after triscaphe arthrodesis", J. Hand Surg., Mar. 1989, vol. 14A, No. 2, Part 1, pp. 297-301.
Rosario et al., "Classifying semantic relations in bioscience texts", In: ACL; Jan. 2004, pp. 430-437.
Samani et al., "The personal genome—the future of personalised medicine?", Lancet, vol. 375, May 1, 2010, pp. 1497-1498.
Saric et al., "Extraction of regulatory gene/protein networks from Medline", Bioinformatics, Mar. 15, 2006; 22(6), pp. 645-650.
Sawyer et al., "Population Genetics of Polymorphism and Divergence", Genetics, Dec. 1, 1992, vol. 132, pp. 1161-1176.
Schafer et al., "A Shrinkage Approach to Large-Scale Covariance Matrix Estimation and Implications for Functional Genomics", Statistical Application in Genetics and Molecular Biology, Feb. 2005, vol. 4, Issue, 1, Article 32, pp. 1175-1189.
Schafer et al., "An empirical Bayes approach to inferring large-scale gene association networks", Bioinformatics, Mar. 15, 2005, vol. 21, No. 6, pp. 754-764.
Schaffter et al., "GeneNetWeaver: in silico benchmark generation and performance profiling of network inference methods", Bioinformatics, Jun. 22, 2011, vol. 27, No. 16, pp. 2263-2270.
Scott et al., "Clinical Pharmacogenetics Implementation Consortium Guidelines for Cytochrome P450-2C19 (CYP2C19) Genotype and Clopidogrel Therapy", Clinical Pharmacology and Therapeutics, vol. 90, No. 2, Aug. 2011, pp. 328-332.
Shabalin, "Matrix eQTL: ultra fast eQTL analysis via large matrix operations", Bioinformatics, May 15, 2012, vol. 28, No. 10, pp. 1353-1358.
Shiina et al., "An update of the HLA genomic region, locus information and disease associations: 2004", Tissue Antigens, vol. 64, No. 6, Aug. 8, 2004, pp. 631-649.
Sing et al., "ROCR: visualizing classifier performance in R", Bioinformatics, 21:3940-3941, Aug. 11, 2005.
Singh et al., "Abnormal Calcium Cycling and cardiac Arrhythmias Associated with the Homan SER96Ala Genetic Variant of Histidine-Rich Calcium-Binding Protein", Journal of the American Heart Association, 2013, vol. 2, 18 pgs.
Smith et al., "Overview of BioCreative II gene mention recognition", Genome Biology, 9 (Suppl 2):S2, Sep. 1, 2008, 19 pgs.
Smith et al., "The causes of synonymous rate variation in the rodent genome: can substitution rates be used to estimate the sex bias in mutation rate?", Genetics, Feb. 16, 1999, vol. 152, pp. 661-673.
Smoller et al., "Family, twin, and adoption studies of bipolar disorder", American Journal of Medical Genetics, vol. 123C, Issue No. 1, pp. 48-58, Nov. 2003, First published Aug. 8, 2003.
Sofaer, "Crohn's disease: the genetic contribution", Gut, 34, pp. 869-871, Jul. 1993.
Tanaka et al., "Molecular cloning and mapping of a human cDNA for cytosolic malate dehydrogenase (MDHI)", Genomics, Feb. 15, 1996, vol. 32, pp. 128-130.
Tari et al., "Querying parse tree database of Medline text to synthesize user-specific biomolecular networks", In: Pacific Symposium on Biocomputing; 2009, pp. 87-98.
Thomas et al., "Coding single-nucleotide polymorphisms associated with complex vs. Mendelian disease: evolutionary evidence for differences in molecular effects", Proc Natl Acad Sci U S A, vol. 101, No. 43, pp. 15398-15403, Oct. 26, 2004.
Tjon et al., "Celiac disease: how complicated can it get?", Immunogenetics, vol. 62, No. 10, Jul. 27, 2010, pp. 641-651.
Trapnell et al., "Differential gene and transcript expression analysis of RNA-seq experiments with TopHat and Cufflinks", Nature Protocols, Mar. 1, 2012, vol. 7, No. 3, pp. 562-578.
Tsujii, NAACL HLT 2009, "BioNLP 2009, Companion Volume: Shared Task on Event Extraction", in: Proceedings of the BioNLP 2009 Workshop Companion Volume for Shared Task, Jun. 5, 2009, 154 pgs. (presented in two parts).
Tusher et al., "Significance analysis of microarrays applied to the ionizing radiation response", PNAS, Apr. 24, 2001, vol. 98, No. 9, pp. 5116-5121.
Van Belle et al., "Type 1 Diabetes: Etiology, Immunology, and Therapeutic Strategies", Physiological Reviews, vol. 91, No. 1, Jan. 1, 2011, pp. 79-118.
Van Vliet-Ostaptchouk et al., "HHEX gene polymorphisms are associated with type 2 diabetes in the Dutch Breda cohort", European Journal of Human Genetics, Jan. 30, 2008, vol. 16, pp. 652-656.
Wang et al., "The diploid Genome sequence of an Asian individual", Nature, Nov. 6, 2008, vol. 456, No. 7218, pp. 60-65.
Wei et al., "From Disease Association to Risk Assessment: An Optimistic View from Genome-Wide Association Studies on Type 1 Diabetes", PLoS Genetics, vol. 5, No. 10, e1000678, Oct. 9, 2009, 11 pgs.
Wermter et al., "You can't beat frequency (unless you use linguistic knowledge)—a qualitative evaluation of association measures for collocation and term extraction", in Proceedings of the 21st International Conference on Computational Linguistics and 44th Annual Meeting of the ACL, Jul. 2006, pp. 785-792.
Xu et al., "Unsupervised method for automatic construction of a disease dictionary from a large free text collection", In: AMIA Annu Symp Proc 2008; Feb. 2008, pp. 820-824.
Crowley, "Ontology Development Information Extraction (ODIE) project", May 11, 2009, retrieved from http:// www.bioontology.org/ODIE-project, [accessed Feb. 11, 2010], 2 pgs.
Danaher et al, "The joint graphical lasso for inverse covariance estimation across multiple classes", J. R. Stat. Soc. Ser. B (Statistical Methodol., 2014, vol. 76, pp. 373-397; arXiv:1111.0324, Jul. 11, 2012.
De Marneffe et al., "The Stanford typed dependencies representation", In: COLING workshop on cross-framework and cross-domain parser evaluation; Aug. 23, 2008, 8 pgs.
Degner et al., "Effect of read-mapping biases on detecting allele-specific expression from RNA-sequencing data", Bioinformatics, vol. 25, No. 24, Oct. 6, 2009, pp. 3207-3212.
Dewey et al., "Gene Coexpression Network Topology of Cardiac Development, Hypertrophy and Failure", Circulation: Cardiovascular Genetics, Feb. 15, 2011, 4(1), 16 pgs.
Dickson et al., "Rare Variants Create Synthetic Genome-Wide Associations", PLOS Biology, 8(1): e1000294, Jan. 26, 2010, 12 pgs.
Dobin et al., "STAR: ultrafast universal RNS-seq aligner", Bioinformatics, Jan. 1, 2013, vol. 29, No. 1, pp. 15-21.
Dobyns et al., "Management of thumb duplication", Clin Orthop., May 1985; vol. 195, pp. 26-44.
Dudley et al., "Evolutionary Meta-Analysis of Association Studies Reveals Ancient Constraints Affecting Disease Marker Discovery", Mol. Biol. Evol., 29(9): 2087-2094, Mar. 1, 2012.
Dumontier et al., "Towards pharmacogenomics knowledge discovery on the semantic web", Briefings Bioinformatics, Mar. 1, 2009; 10(2), pp. 153-163.
Eble et al., "Contractile activity is required for sarcomeric assembly in phenylephrine-induced cardia myocyte hypertrophy", Am. J. Physiol., May 1, 1998, vol. 274, pp. C1226-C1237.
Eichler et al., "Missing heritability and strategies for finding the underlying causes of complex disease", Nature Reviews Genet., Author manuscript; Final version published: Nature Reviews Genetics 11(6): 446-450, Jun. 2010.
Faust, "Centrality in affiliation networks", Social Networks, Apr. 1997, vol. 19, pp. 157-191.
Feero et al., "Genomewide association studies and assessment of the risk of disease", The New England Journal of Medicine, Jul. 6, 2010, vol. 363, pp. 166-176.
Frey et al., "Mechanisms of disease: hypertrophic cardiomyopathy", Nature Reviews Cardiology, Feb. 2012, vol. 9, pp. 91-100.
Friedman et al., "Genies: a natural-language processing system for the extraction of molecular pathways from journal articles", In: ISMB (supplement of Bioinformatics); Jun. 1, 2001, pp. S74-S82.
Friedman et al., "Sparse inverse covariance estimation with the graphical lasso", Biostatistics, Dec. 12, 2007, vol. 9, pp. 432-441.
Fundel et al., "RelEx-relation extraction using dependency parse trees", Bioinformatics, Feb. 1, 2007; 23(3), pp. 365-371.

(56) References Cited

OTHER PUBLICATIONS

Garten et al., "Pharmspresso: a text mining tool for extraction of pharmacogenomic concepts and relationships from full text", BMC Bioinformatics, Feb. 2009; 10 (S-2), 9 pgs.
Goldstein, "Common Genetic Variation and Human Traits", The New England Journal of Medicine, Apr. 23, 2009, vol. 360, pp. 1696-1698.
Grantham, "Amino acid difference formula to help explain protein evolution", Science, Sep. 6, 1974, vol. 185, pp. 862-864.
Green et al., "Charting a course for genomic medicine from base pairs to bedside", Nature, vol. 470, Feb. 10, 2011, pp. 204-213.
Green et al., "Disclosure of APOE Genotype for Risk of Alzheimer's Disease", The New England Journal of Medicine, vol. 361, No. 3, Jul. 16, 2009, pp. 245-254.
Gupta et al., "Using ontologies and the web to learn lexical semantics", In: IJCAI; Jan. 2007, pp. 1618-1623.
Hakenberg et al., "Gene mention normalization and interaction extraction with context models and sentence motifs", Genome Biology 9(Suppl 2):S14, Sep. 1, 2008, 16 pgs.
Han et al., "A long noncoding RNA protects the heart from pathological hypertrophy", Nature, Oct. 2, 2014, vol. 514, No. 7520, pp. 102-106.
Hansen et al., "Generating Genome-Scale Candidate Gene Lists for Pharmacogenomics", Clin. Pharmacol. Ther., Aug. 2009, vol. 86, No. 2, pp. 183-189, first published Apr. 15, 2009.
Harney et al., "Fine mapping of the MHC Class III region demonstrates association of AIF1 and rheumatoid arthritis", Rheumatology 2008, 47:1761-1767, Advance publication Oct. 3, 2008, 7 pgs.
Hedges et al., "TimeTree: a public knowledge-base of divergence times among organisms", Bioinformatics, Applications Note, Oct. 4, 2006, vol. 22, No. 23, pp. 2971-2972.
Hernandez et al., "Classic Selective Sweeps Were Rare in Recent Human Evolution", Science, Apr. 8, 2011, vol. 331, pp. 920-924.
Hindorff et al., "Potential etiologic and functional implications of genome-wide association loci for human diseases and traits", Proc Natl Acad Sci USA, Jun. 9, 2009. 106(23): pp. 9362-9367. PMCID: 2687147.
Hirschman et al., "The biocreative II—critical assessment for information extraction in biology challenge", Genome Biology, vol. 9, Suppl 2 S8, Sep. 1, 2008, 8 pgs.
Huang et al., "Mining physical protein-protein interactions from the literature", Genome Biology 9(Suppl 2):512, Sep. 1, 2008, 13 pgs.
Huber, "Robust Estimation of a Location Parameter", Ann. Math. Stat., Mar. 1, 1964, vol. 35, No. 1, pp. 73-101.
Hunter et al., "OpenDMAP: an open-source, ontology-driven concept analysis engine, with applications to capturing knowledge regarding protein transport, protein interactions and cell-type-specific gene expression", BMC Bioinformatics, Jan. 31, 2008, 9(78), 22 pgs.
Johnson et al., "An Open Access Database of Genome-wide Association Results BMC", Medical Genetics, Jan. 22, 2009, vol. 10, No. 6, 17 pgs., doi: 10.1186/1471-2350-10-6.
Joy et al., "High-Betweenness Proteins in the Yeast Protein Interaction Network", Journal of Biomedicine and Biotechnology, 2005, vol. 2, pp. 96-103.
Kent et al., "The human genome browser at UCSC", Genome Research, vol. 12, 2002, pp. 996-1006.
Kimura, "The neutral theory of molecular evolution", Cambridge University Press, Scientific American, 1979, 135 pgs.
Klein et al., "Accurate unlexicalized parsing", In: ACL; 2003, pp. 423-430.
Klein et al., "Integrating genotype and phenotype information: an overview of the PharmGKB project", Pharmacogenomics Journal, Feb. 2001;1(3), pp. 167-170.
Knublauch et al., "The Protege OWL plugin: an open development environment for semantic web applications", In: ISWC; 2004, pp. 229-243.
Kohane et al., "The incidentalome: a threat to genomic medicine", The Journal of the American Medical Association, vol. 296, No. 2, Jul. 11, 2006, pp. 212-215.
Kong et al., "A high-resolution recombination map of the human genome", Nature Genetics, vol. 31, pp. 241-247, published online Jun. 10, 2002.
Krallinger et al., "Evaluation of text-mining systems for biology: overview of the Second BioCreative community challenge", Genome Biology, Sep. 1, 2008, 9 (Suppl2), pp. S1-S1.9.
Krallinger et al., "Overview of the protein-protein interaction annotation extraction task of BioCreative II", Genome Biology, Sep. 1, 2008, 9 (Suppl. 2), pp. S4-S4.19.
Krallinger et al., "Linking genes to literature: text mining, information extraction, and retrieval applications for biology", Genome Biology, 9 (Suppl 2): pp. S8-S8.14, Sep. 1, 2008.
Kumar et al., "Phylomedicine: an evolutionary telescope to explore and diagnose the universe of disease mutations", Trends Genet., 27(9), pp. 377-386, Sep. 2011, Epub Jul. 20, 2011.
Lee et al., "A nucleocytoplasmic malate dehydrogenase regulates p53 transcriptional activity in response to metabolic stress", Cell Death and Differentiation, Mar. 2009, vol. 16, pp. 738-748.
Leitner et al., "Introducing meta-services for biomedical information extraction", Genome Biology 9(Suppl 2):S6-S6.11, Sep. 1, 2008.
Levy et al., "The Diploid Genome Sequence of an Individual Human", PLoS Biology, Oct. 2007, vol. 5, Issue 10, pp. 2113-2144.

* cited by examiner

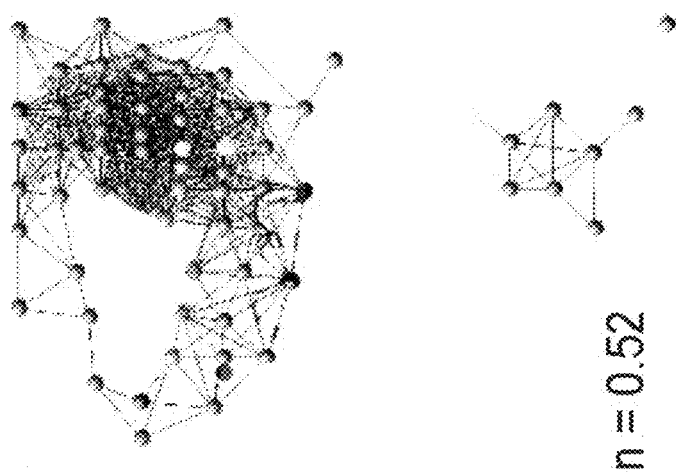

Raw data
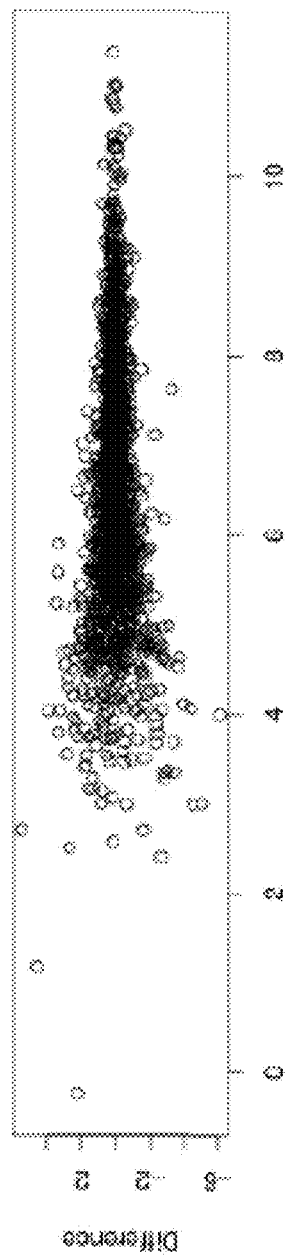
Fig. 7A.1
Within set experiments
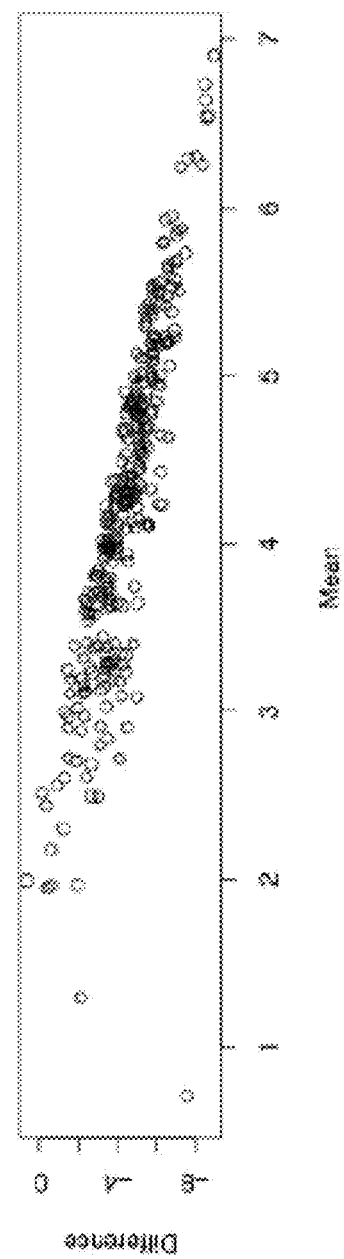
Fig. 7A.2
Between set experiments

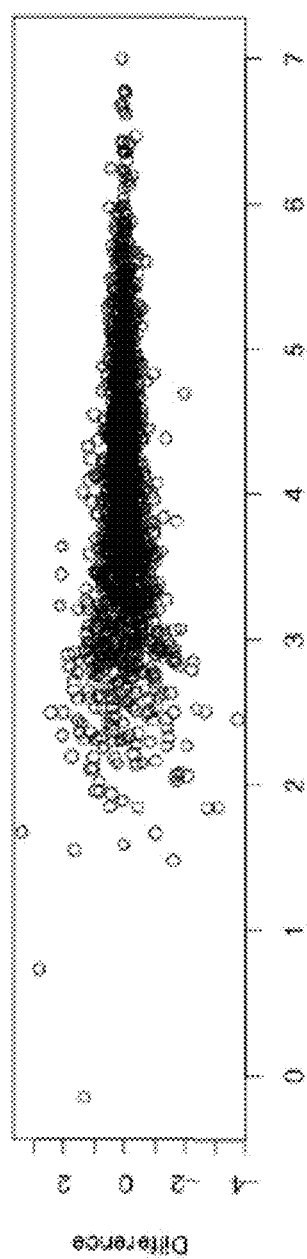
Fig. 7B.1
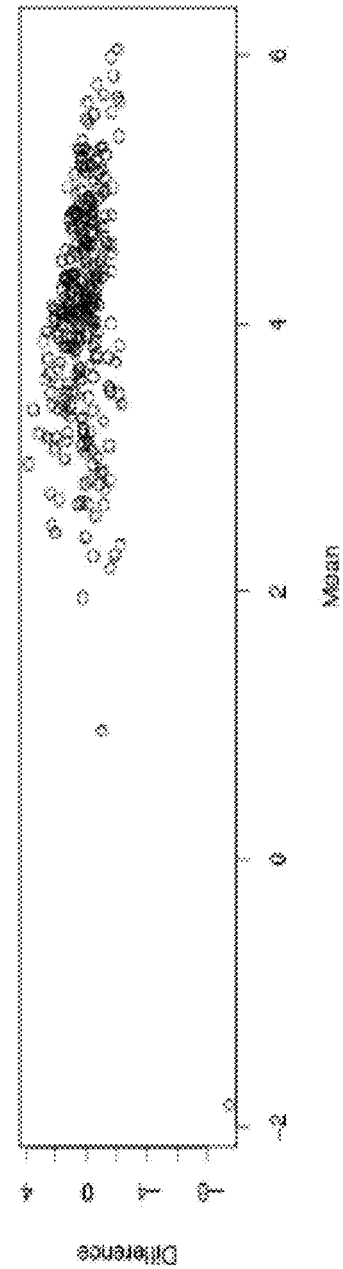
Fig. 7B.2

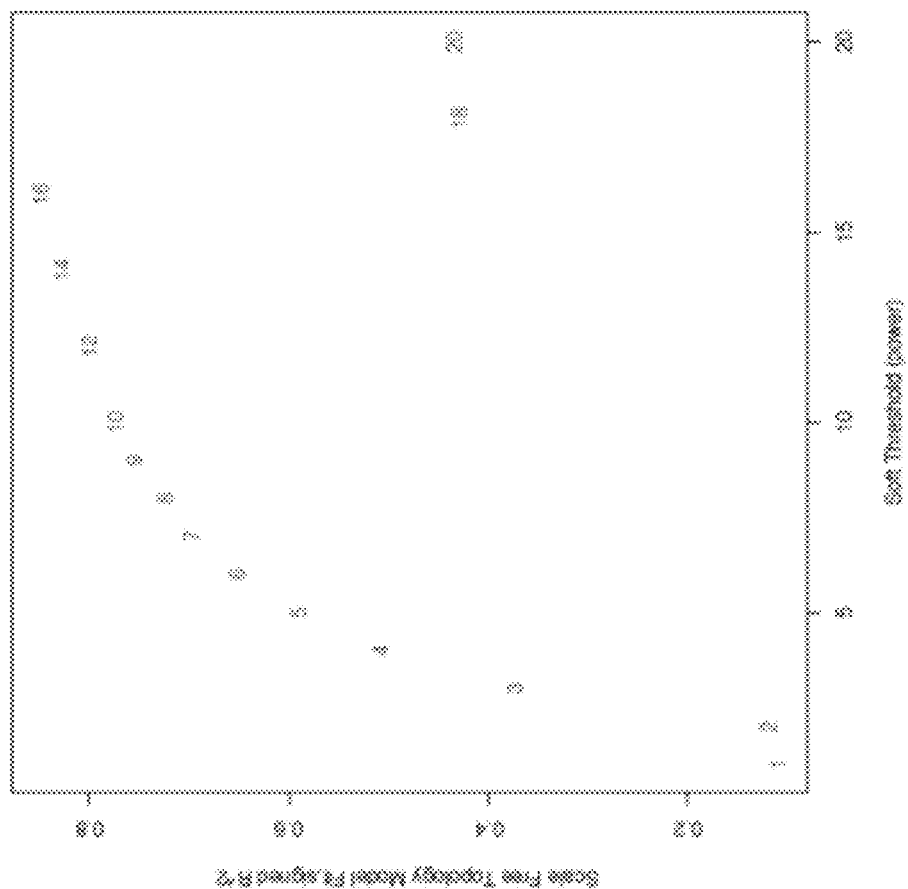
Fig. 9A.1

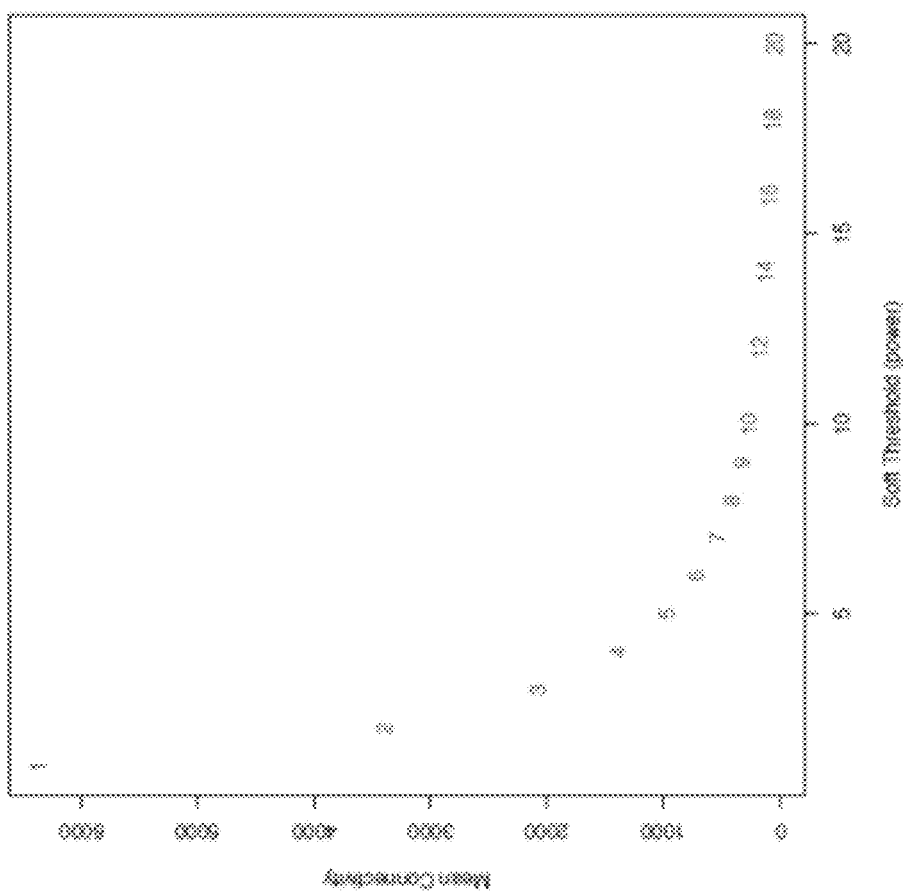
Fig. 9A.2

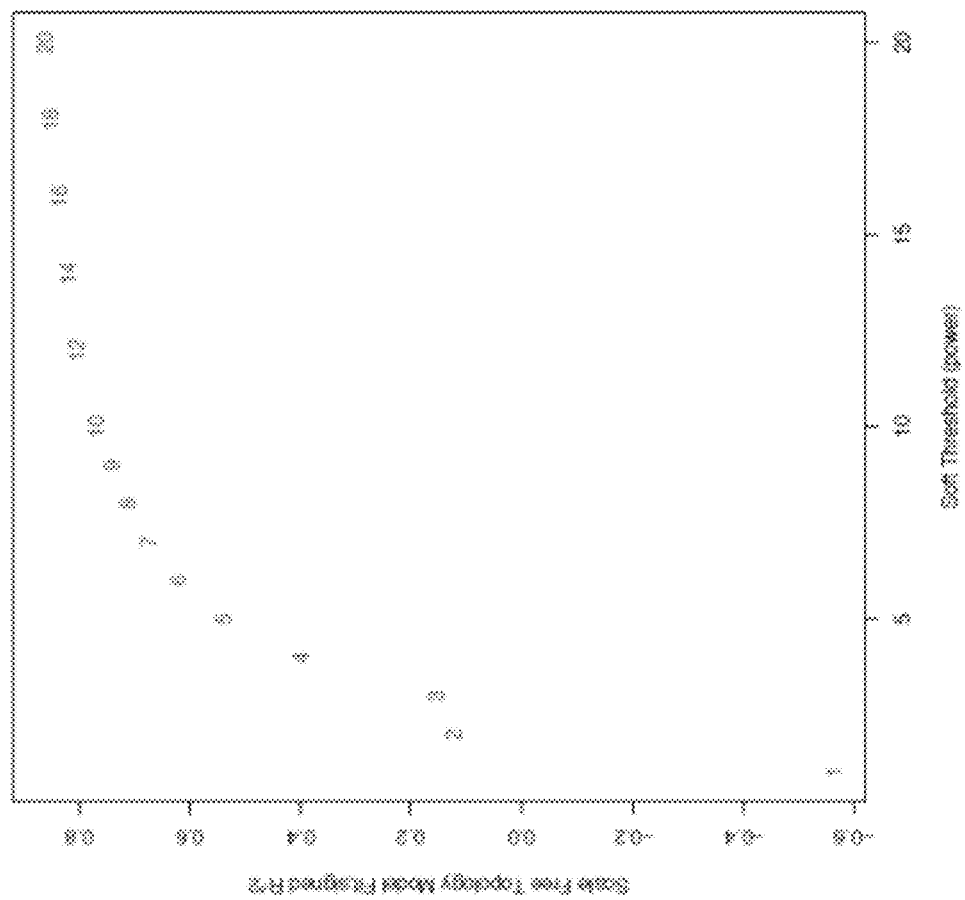
Fig. 9B.1

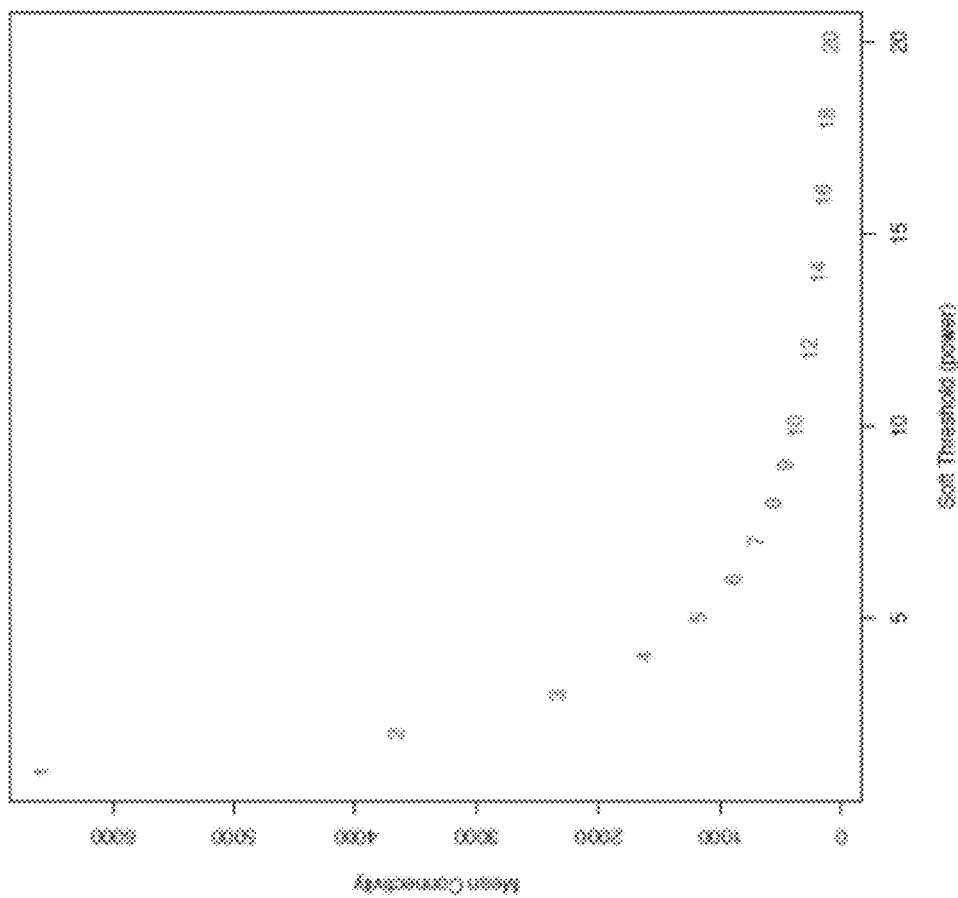
Fig. 9B.2

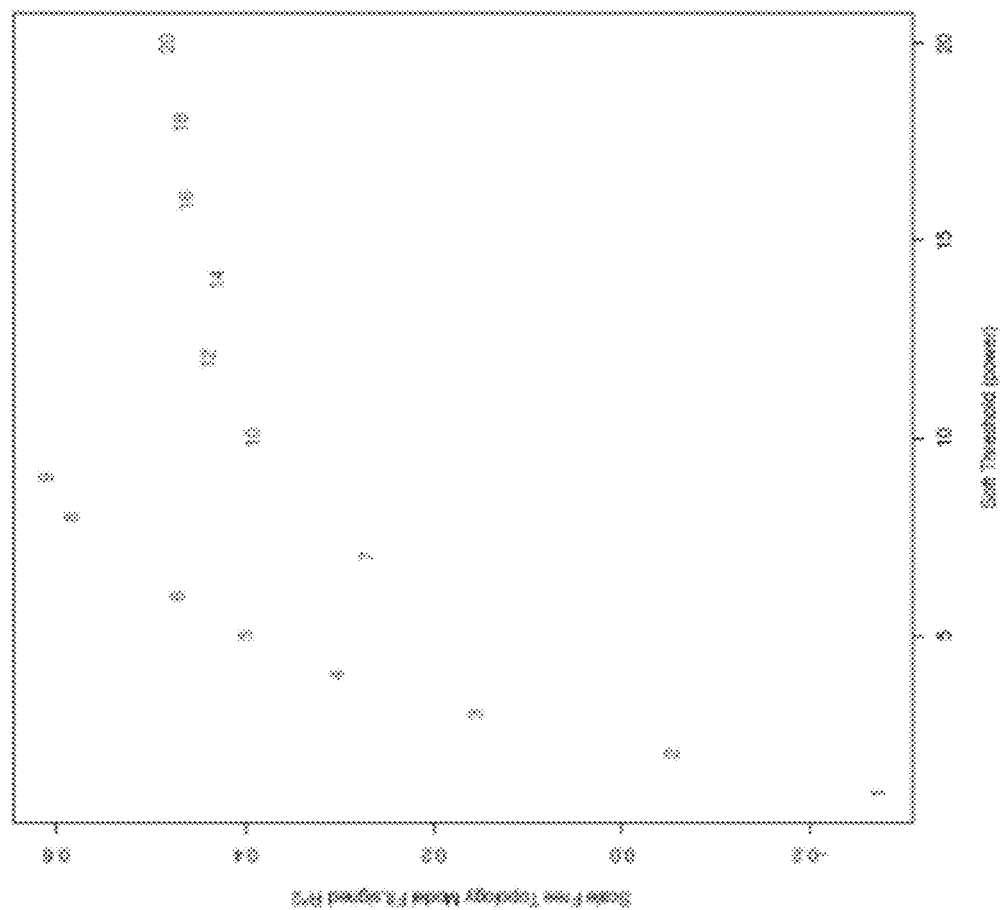
Fig. 10A.1

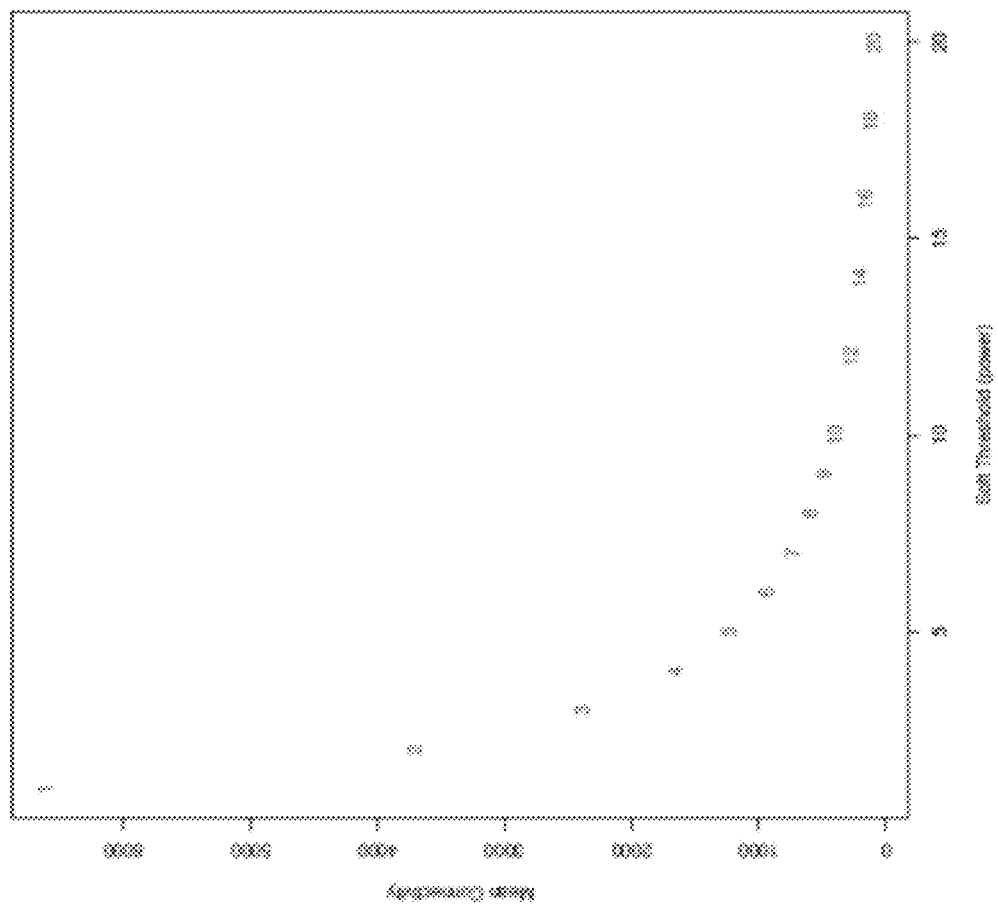
Fig. 10A.2

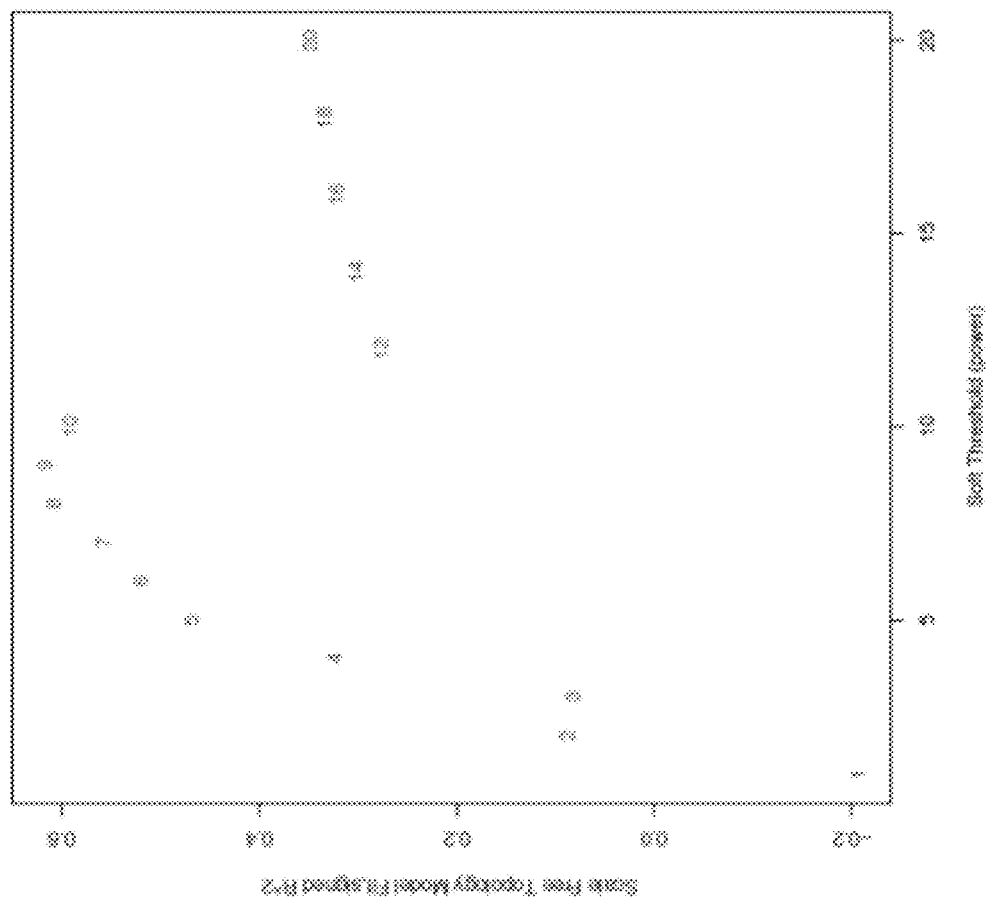
Fig. 10B.1

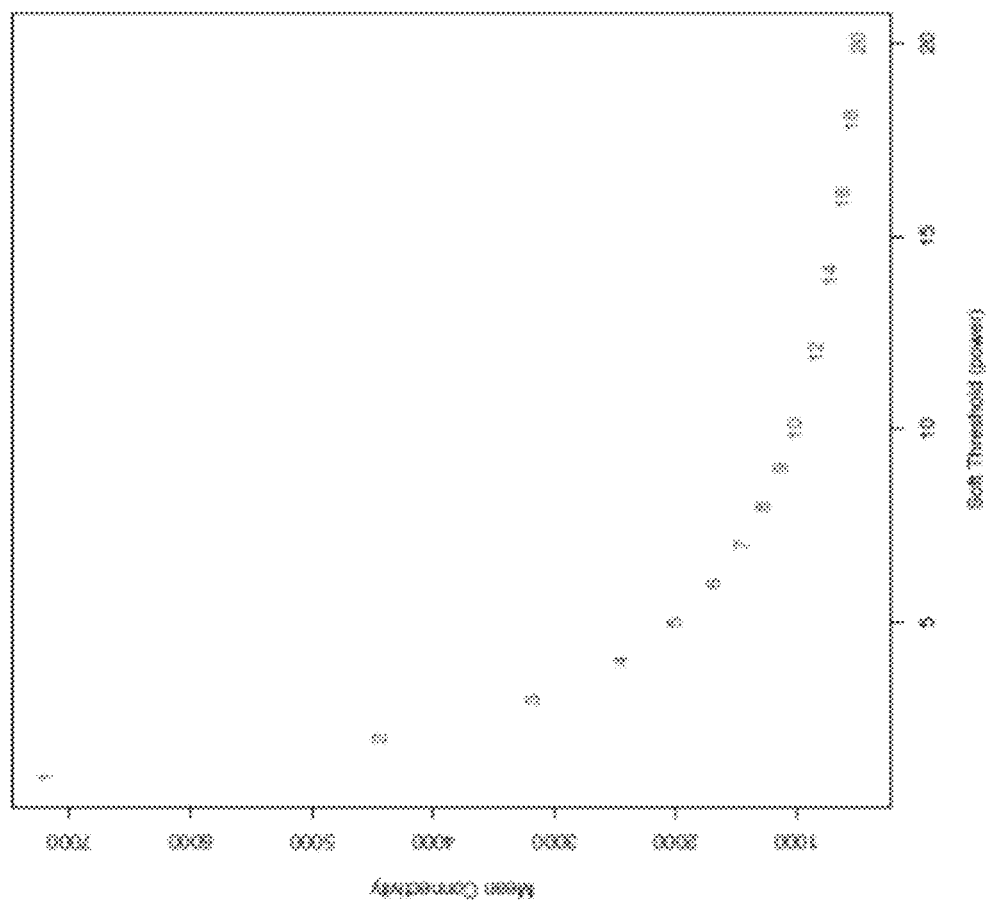
Fig. 10B.2

Table 1

| Term | Count | % | P value | Benjamini corrected P value |
|---|---|---|---|---|
| GO:0010498~proteasomal protein catabolic process | 9 | 3.703703704 | 5.88E-05 | 0.085176908 |
| GO:0043161~proteasomal ubiquitin-dependent protein catabolic process | 9 | 3.703703704 | 5.88E-05 | 0.085176908 |
| GO:0031397~negative regulation of protein ubiquitination | 7 | 2.880658436 | 4.21E-04 | 0.273255325 |
| GO:0031400~negative regulation of protein modification process | 8 | 3.29218107 | 9.86E-04 | 0.392455826 |
| GO:0031145~anaphase-promoting complex-dependent proteasomal ubiquitin-dependent protein catabolic process | 6 | 2.469135802 | 0.001627358 | 0.460365964 |
| GO:0051436~negative regulation of ubiquitin-protein ligase activity during mitotic cell cycle | 6 | 2.469135802 | 0.001627358 | 0.460365964 |
| GO:0051352~negative regulation of ligase activity | 6 | 2.469135802 | 0.001863042 | 0.431655869 |
| GO:0051444~negative regulation of ubiquitin-protein ligase activity | 6 | 2.469135802 | 0.001863042 | 0.431655869 |
| GO:0051437~positive regulation of ubiquitin-protein ligase activity during mitotic cell cycle | 6 | 2.469135802 | 0.001989821 | 0.395244156 |
| GO:0031396~regulation of protein ubiquitination | 7 | 2.880658436 | 0.002047355 | 0.358252472 |
| GO:0051443~positive regulation of ubiquitin-protein ligase activity | 6 | 2.469135802 | 0.002262134 | 0.34875992 |
| GO:0051439~regulation of ubiquitin-protein ligase activity during mitotic cell cycle | 6 | 2.469135802 | 0.00240802 | 0.333582434 |
| GO:0051351~positive regulation of ligase activity | 6 | 2.469135802 | 0.002720135 | 0.338114005 |

Fig. 14

| | | | |
|---|---|---|---|
| GO:0051438~regulation of ubiquitin-protein ligase activity | 6 | 2.469135802 | 0.003627379 | 0.393770917 |
| GO:0051340~regulation of ligase activity | 6 | 2.469135802 | 0.004265877 | 0.417087961 |
| GO:0010604~positive regulation of macromolecule metabolic process | 22 | 9.053497942 | 0.004336655 | 0.397390617 |
| GO:0006511~ubiquitin-dependent protein catabolic process | 10 | 4.115226337 | 0.004759814 | 0.403281364 |
| GO:0031398~positive regulation of protein ubiquitination | 6 | 2.469135802 | 0.004980809 | 0.396083111 |
| GO:0032269~negative regulation of cellular protein metabolic process | 8 | 3.29218107 | 0.009749754 | 0.604541584 |
| GO:0032268~regulation of cellular protein metabolic process | 14 | 5.761316872 | 0.009937347 | 0.589353536 |
| GO:0051248~negative regulation of protein metabolic process | 8 | 3.29218107 | 0.011889021 | 0.634560761 |
| GO:0031401~positive regulation of protein modification process | 8 | 3.29218107 | 0.011889021 | 0.634560761 |
| GO:0032270~positive regulation of cellular protein metabolic process | 9 | 3.703703704 | 0.012008682 | 0.618380086 |
| GO:0006412~translation | 11 | 4.526748971 | 0.012280118 | 0.607797787 |
| GO:0051247~positive regulation of protein metabolic process | 9 | 3.703703704 | 0.01527673 | 0.670642671 |
| GO:0006888~ER to Golgi vesicle-mediated transport | 4 | 1.646090535 | 0.017660853 | 0.706846291 |
| GO:0006029~proteoglycan metabolic process | 4 | 1.646090535 | 0.018805668 | 0.713643232 |
| GO:0043069~negative regulation of programmed cell death | 11 | 4.526748971 | 0.020485907 | 0.729261669 |
| GO:0060548~negative regulation of cell death | 11 | 4.526748971 | 0.020083881 | 0.72089733 |
| GO:0000278~mitotic cell cycle | 11 | 4.526748971 | 0.024616387 | 0.765975085 |
| GO:0048193~Golgi vesicle transport | 6 | 2.469135802 | 0.029445483 | 0.813072091 |
| GO:0043086~negative regulation of catalytic activity | 9 | 3.703703704 | 0.030252983 | 0.810273943 |
| GO:0006024~glycosaminoglycan | 3 | 1.234567901 | 0.030687983 | 0.803736453 |

Fig. 14 (cont.)

| | | | | |
|---|---|---|---|---|
| biosynthetic process | | | | |
| GO:0034660~ncRNA metabolic process | 8 | 3.29218107 | 0.032680051 | 0.813236374 |
| GO:0006023~aminoglycan biosynthetic process | 3 | 1.234567901 | 0.036346186 | 0.836240734 |
| GO:0031328~positive regulation of cellular biosynthetic process | 16 | 6.58436214 | 0.036729029 | 0.829944083 |
| GO:0014012~axon regeneration in the peripheral nervous system | 2 | 0.823045267 | 0.038959414 | 0.838679905 |
| GO:0030433~ER-associated protein catabolic process | 3 | 1.234567901 | 0.039314088 | 0.832564073 |
| GO:0043632~modification-dependent macromolecule catabolic process | 14 | 5.761316872 | 0.039969037 | 0.828918141 |
| GO:0019941~modification-dependent protein catabolic process | 14 | 5.761316872 | 0.039969037 | 0.828918141 |
| GO:0009891~positive regulation of biosynthetic process | 16 | 6.58436214 | 0.040863477 | 0.827230111 |
| GO:0031399~regulation of protein modification process | 9 | 3.703703704 | 0.041479826 | 0.82354007 |
| GO:0006414~translational elongation | 5 | 2.057613169 | 0.044248539 | 0.835416986 |
| GO:0043066~negative regulation of apoptosis | 10 | 4.115226337 | 0.044604504 | 0.830100099 |
| GO:0030166~proteoglycan biosynthetic process | 3 | 1.234567901 | 0.045513102 | 0.82868805 |
| GO:0009636~response to toxin | 4 | 1.646090535 | 0.046263702 | 0.826279515 |
| GO:0050808~synapse organization | 4 | 1.646090535 | 0.046263702 | 0.826279515 |
| GO:0050905~neuromuscular process | 4 | 1.646090535 | 0.048161831 | 0.831445257 |
| GO:0007049~cell cycle | 17 | 6.995884774 | 0.049910924 | 0.835342973 |
| GO:0010557~positive regulation of macromolecule biosynthetic process | 15 | 6.172839506 | 0.050024007 | 0.829153796 |
| GO:0007017~microtubule-based process | 8 | 3.29218107 | 0.050026262 | 0.822326016 |
| GO:0009100~glycoprotein metabolic process | 7 | 2.880658436 | 0.050865854 | 0.820820072 |
| GO:0051603~proteolysis involved in cellular protein catabolic process | 14 | 5.761316872 | 0.053451602 | 0.829789323 |

Fig. 14 (cont.)

| | | | |
|---|---|---|---|
| GO:0044257~cellular protein catabolic process | 14 | 5.7613316872 | 0.05518637 | 0.83332792 |
| GO:0006916~anti-apoptosis | 7 | 2.8806858436 | 0.0557493773 | 0.8302774497 |
| GO:0031099~regeneration | 4 | 1.6460090535 | 0.0624893331 | 0.8584599922 |
| GO:0060135~maternal process involved in female pregnancy | 2 | 0.8230045267 | 0.0640090029 | 0.8602073848 |
| GO:0043062~extracellular structure organization | 6 | 2.4691358802 | 0.06415533 | 0.8551118823 |
| GO:0001503~ossification | 5 | 2.0576133169 | 0.0652242165 | 0.8546422667 |
| GO:0006790~sulfur metabolic process | 5 | 2.0576133169 | 0.0652242165 | 0.8546422667 |
| GO:0007416~synaptogenesis | 3 | 1.2345677901 | 0.06602007 | 0.8528335415 |
| GO:0060021~palate development | 3 | 1.2345677901 | 0.06602007 | 0.8528335415 |
| GO:0030163~protein catabolic process | 14 | 5.7613316872 | 0.0670702556 | 0.85226774 |
| GO:0022402~cell cycle process | 13 | 5.3497942339 | 0.0698831997 | 0.8589173890 |
| GO:0016567~protein ubiquitination | 5 | 2.0576133169 | 0.0720468863 | 0.8629508819 |
| GO:0044092~negative regulation of molecular function | 9 | 3.7037037704 | 0.0743314683 | 0.8669544868 |
| GO:0015031~protein transport | 16 | 6.58436214 | 0.0774352688 | 0.8737761955 |
| GO:0060348~bone development | 5 | 2.0576133169 | 0.0791996679 | 0.8754975455 |
| GO:0001776~leukocyte homeostasis | 3 | 1.2345677901 | 0.0810799755 | 0.8775481002 |
| GO:0010628~positive regulation of gene expression | 13 | 5.3497942339 | 0.0820242567 | 0.8764728555 |
| GO:0045184~establishment of protein localization | 16 | 6.58436214 | 0.0822078472 | 0.8729162331 |
| GO:0043085~positive regulation of catalytic activity | 12 | 4.9382716053 | 0.0832249699 | 0.8688111616 |
| GO:0051173~positive regulation of nitrogen compound metabolic process | 14 | 5.7613316872 | 0.0828203613 | 0.8666078921 |
| GO:0009611~response to wounding | 12 | 4.9382716053 | 0.0910114565 | 0.8881265233 |
| GO:0042102~positive regulation of T cell proliferation | 3 | 1.2345677901 | 0.09299667 | 0.8899843227 |
| GO:0046907~intracellular transport | 14 | 5.7613316872 | 0.0931544283 | 0.8867944493 |
| GO:0032446~protein modification by small protein conjugation | 5 | 2.0576133169 | 0.0965255524 | 0.8923371340 |

Fig. 14 (cont.)

| | | | |
|---|---|---|---|
| GO:0044265~cellular macromolecule catabolic process | 15 | 6.172839506 | 0.096913165 | 0.889881539 |
| GO:0007267~cell-cell signaling | 13 | 5.349794239 | 0.098157055 | 0.889698317 |
| GO:0016055~Wnt receptor signaling pathway | 5 | 2.057613169 | 0.098552671 | 0.887313991 |
| GO:0007268~synaptic transmission | 8 | 3.29218107 | 0.098819646 | 0.88460464 |
| GO:0006508~proteolysis | 20 | 8.230452675 | 0.0998021 | 0.883811535 |

Fig. 14 (cont.)

Table 2

| Entrez ID | Gene Name |
|---|---|
| 79139 | Der1-like domain family, member 1 |
| 26270 | F-box protein 6 |
| 51035 | UBX domain protein 1 |
| 51529 | anaphase promoting complex subunit 11 |
| | cell division cycle 26 homolog (S. cerevisiae); cell division cycle 26 homolog (S. cerevisiae) |
| 246184 | pseudogene |
| 5705 | proteasome (prosome, macropain) 26S subunit, ATPase, 5 |
| 5682 | proteasome (prosome, macropain) subunit, alpha type, 1 |
| 7314 | ubiquitin B |
| 7324 | ubiquitin-conjugating enzyme E2E 1 |

Fig. 15

METHOD AND SYSTEM FOR NETWORK MODELING TO ENLARGE THE SEARCH SPACE OF CANDIDATE GENES FOR DISEASES

CROSS-REFERENCE TO RELATED APPLICATIONS

This application claims priority to U.S. Provisional Application No. 61/497,542 filed Jun. 16, 2011, which is hereby incorporated by reference in its entirety for all purposes.

This application is related to U.S. Non-provisional application Ser. Nos. 13/445,923 filed Apr. 13, 2012; 13/445,925 filed Apr. 13, 2012, and 13/445,926 filed Apr. 13, 2012, herein incorporated by reference in their entirety for all purposes.

STATEMENT OF GOVERNMENT SPONSORED SUPPORT

This invention was made with Government support under contracts HL083914 and OD004613 awarded by the National Institutes of Health. The Government has certain rights in this invention.

FIELD OF THE INVENTION

The present invention generally relates to the field of genomics. More particularly, the present invention relates to the field of whole genome sequencing.

BACKGROUND OF THE INVENTION

Despite advances in diagnosis and management, the clinical syndrome of heart failure remains a leading cause of hospitalization and death in developed countries with a worse five year prognosis than most cancers (Jhund P S, Macintyre K, Simpson C R, Lewsey J D, Stewart S, Redpath A, Chalmers J W, Capewell S, McMurray J J. Long-term trends in first hospitalization for heart failure and subsequent survival between 1986 and 2003: a population study of 5.1 million people. Circulation. 2009; 119:515-523; these and all other references cited herein are incorporated by reference for all purposes). Disparate mechanisms of cardiac stress invoke a common pathway of adaptive myocyte hypertrophy which progresses to impaired systolic function and dilated, thinned myocardium. Expression of several genes is known to differ reproducibly between normal adult myocardium and failing and hypertrophied myocardium. Some of these differentially expressed genes, such as cardiac muscle alpha-myosin heavy chain 6 (MYH6) and cardiac muscle beta-myosin heavy chain 7 (MYH7), comprise the contractile apparatus of the sarcomere. Others, such as sarcoplasmic reticulum calcium ATPase 2 (ATP2A2), phospholamban (PLN), and solute carrier family 2, facilitated glucose transporter member 4 (SLC2A4), are principally involved in myocardial calcium cycling and energetics (Feldman A M, Weinberg E O, Ray P E, Lorell B H. Selective changes in cardiac gene expression during compensated hypertrophy and the transition to cardiac decompensation in rats with chronic aortic banding. Circ Res. 1993; 73:184-192; Lyn D, Liu X, Bennett N A, Emmett N L. Gene expression profile in mouse myocardium after ischemia. Physiol Genomics. 2000; 2:93-100; Yue P, Long C S, Austin R, Chang K C, Simpson P C, Massie B M. Post-infarction heart failure in the rat is associated with distinct alterations in cardiac myocyte molecular phenotype. J Mol Cell Cardiol. 1998; 30:1615-1630; Rajabi M, Kassiotis C, Razeghi P, Taegtmeyer H. Return to the fetal gene program protects the stressed heart: a strong hypothesis. Heart Fail Rev. 2007; 12:331-343; Chien K R. Stress pathways and heart failure. Cell. 1999; 98:555-558; Hoshijima M, Chien K R. Mixed signals in heart failure: cancer rules. J Clin Invest. 2002; 109:849-855).

It has thus been proposed that myocardial adaptation involves myosin switch and a switch from fatty acid oxidation to glycolysis as the main metabolic pathway of the cardio myocyte. Similar differential gene expression has been observed in fetal myocardium, leading to a hypothesis that there is a coordinated gene program that overlaps between fetal and failing and hypertrophied myocardium 5. It is, however, unclear whether such changes represent a truly coordinated biological response mediated by common regulators.

The incomplete understanding of these shared genomic response pathways is largely due to statistical and computational limitations inherent to traditional differential expression experiments, in which the expression of a pre-defined set of genes is compared between two different phenotypes. These limitations have been compounded by small sample sizes in previous microarray experiments and have precluded prior unbiased genome-wide evaluation of this hypothesis.

Network based approaches can be used to identify patterns of shared gene expression, regulation, or protein interaction while limiting the number of statistical comparisons and thus the false discovery rate (Jeong H, Mason S P, Barabasi A L, Oltvai Z N. Lethality and centrality in protein networks. Nature. 2001; 411:41-42; Jeong H, Tombor B, Albert R, Oltvai Z N, Barabasi A L. The large-scale organization of metabolic networks. Nature. 2000; 407:651-654). Literature derived networks have been used to reveal potential targets for abrogation of restenotic atherosclerotic coronary artery disease and in doing so recapitulated targets of known therapeutic agents. Other investigators have used gene coexpression analysis to uncover pathways regulated by disease susceptibility genes (Chen Y, Zhu J, Lum P Y, Yang X, Pinto S, MacNeil D J, Zhang C, Lamb J, Edwards S, Sieberts S K, Leonardson A, Castellini L W, Wang S, Champy M F, Zhang B, Emilsson V, Doss S, Ghazalpour A, Horvath S, Drake T A, Lusis A J, Schadt E E. Variations in DNA elucidate molecular networks that cause disease. Nature. 2008; 452:429-435). Candidate causal gene relationships have subsequently been validated with high fidelity in transgenic and gene knock-down experiments (Yang X, Deignan J L, Qi H, Zhu J, Qian S, Zhong J, Torosyan G, Majid S, Falkard B, Kleinhanz R R, Karlsson J, Castellani L W, Mumick S, Wang K, Xie T, Coon M, Zhang C, Estrada-Smith D, Farber C R, Wang S S, van Nas A, Ghazalpour A, Zhang B, Macneil D J, Lamb J R, Dipple K M, Reitman M L, Mehrabian M, Lum P Y, Schadt E E, Lusis A J, Drake T A. Validation of candidate causal genes for obesity that affect shared metabolic pathways and networks. Nat Genet. 2009; 41:415-423; Schadt E E. Molecular networks as sensors and drivers of common human diseases. Nature. 2009; 461:218-223).

SUMMARY OF THE INVENTION

With the advent of low cost, high-throughput whole genome sequencing ("next generation sequencing"), the tools to assay human genetic variation contributing to inherited disease syndromes are now available. Traditional approaches to identifying causative genes and genetic variants in diseased individuals have leveraged inheritance information and the segregation of known genetic markers with disease to pinpoint areas of the genome implicated in disease. Whole genome sequencing allows for assaying genetic variation at every position in the human genome and has the potential to revolutionize the study of inherited diseases. One of the main barriers to the realization of this goal in genome interpretation pipelines is the difficulty in prioritizing the millions of genetic variants in known genes. This is currently addressed in many research settings by identifying variants in genes known previously to be associated with human disease syndromes, an approach which limits the scope of this biological technology. In an embodiment of the present invention, however, a method is described for prioritization of genetic variants, and identification of disease genes, using network modeling of gene associations.

Gene coexpression data, protein interaction, and genetic variation data are rich data-sources for inferring relationships between genes. A method according to an embodiment of the present invention uses these data to create Bayesian networks of causal interactions between genes, with genetic variation as a perturbation from which causality is inferred, and then identifies modular sub-networks from hierarchical clustering of links between genes.

Using known interactions in a curated compendium of disease-gene interactions, a method according to an embodiment of the present invention is disclosed to prioritize genome-wide genetic variants or gene products relevant to Mendelian disease according to their impact and actionability as a scaffold. In a method of the present invention, the subnetworks are searched for genes less than or equal to two steps away from known disease genes.

In an embodiment, this expanded set of putative disease genes is used in annotation of whole genome sequences to restrict the search space for variants with causal implications in inherited disease syndromes as follows: 1) variants in known coding (exons) regions are annotated according to predicted pathogenicity to prioritize genome-wide genetic variants or gene products relevant to Mendelian disease according to their impact and actionability and 2) variants in important non-coding regions (splice sites, 5' and 3' untranslated regions, microRNA targets and miRNA sequences targeting the gene, enhancers, promoters, and repressors) are identified.

The present invention has application in at least the following areas: mapping causal gene loci in inherited disease syndromes using whole genome sequence data; creating disease and carrier state predictions from whole genome sequencing of healthy individuals as part of a genome sequence interpretation pipeline; identifying targets for research on the pathophysiology of inherited disease syndromes; and prioritization of genes for designing capture-based sequencing platforms and hybridization-based genotyping technologies for rapid molecular diagnosis of inherited disease syndromes.

Among other things, network analysis techniques allow a more accurate reflection of underlying systems biology to be realized than traditional unidimensional molecular biology approaches. In yet another embodiment of the present invention, using gene coexpression network analysis, the gene expression network topology of cardiac hypertrophy and failure is defined as well as the extent of recapitulation of fetal gene expression programs in failing and hypertrophied adult myocardium. Also, the development of network analysis techniques for this embodiment of the present invention, provides examples for network analysis techniques in other embodiments of the present invention.

In an embodiment of the present invention, unbiased marginal module analysis of gene coexpression networks from all murine myocardial transcript abundance data available in the published literature is used to formally evaluate the hypotheses that there are gene programs unique to fetal myocardium and these gene programs are re-capitulated in myocardial adaptation.

In an embodiment, all myocardial transcript data in the Gene Expression Omnibus (n=1617) was assembled. Since hierarchical analysis revealed species had primacy over disease clustering, this analysis focused on the most complete (murine) dataset (n=478). Using gene expression markers of myocardial, adaptation were members of upregulated modules but not hub genes genes. In an embodiment, ZIC2 was identified as a novel transcription factor associated with coexpression modules common to developing and failing myocardium. Of 50 fetal gene co-expression modules, three (6%) were reproduced in hypertrophied myocardium and seven (14%) were reproduced in failing myocardium. One fetal module was common to both failing and hypertrophied myocardium.

Among other things, network modeling allows systems analysis of cardiovascular development and disease. An embodiment of the present invention revealed specific gene expression modules active during both development and disease and specific candidates for their regulation.

These and other embodiments can be more fully appreciated upon an understanding of the detailed description of the invention as disclosed below in conjunction with the attached figures.

BRIEF DESCRIPTION OF THE DRAWINGS

The following drawings will be used to more fully describe embodiments of the present invention.

Shown in FIGS. 3A-3E are charts and graphs demonstrating the reproducibility of developmental gene modules in heart failure and cardiac hypertrophy according to an embodiment of the present invention.

Figure 4:
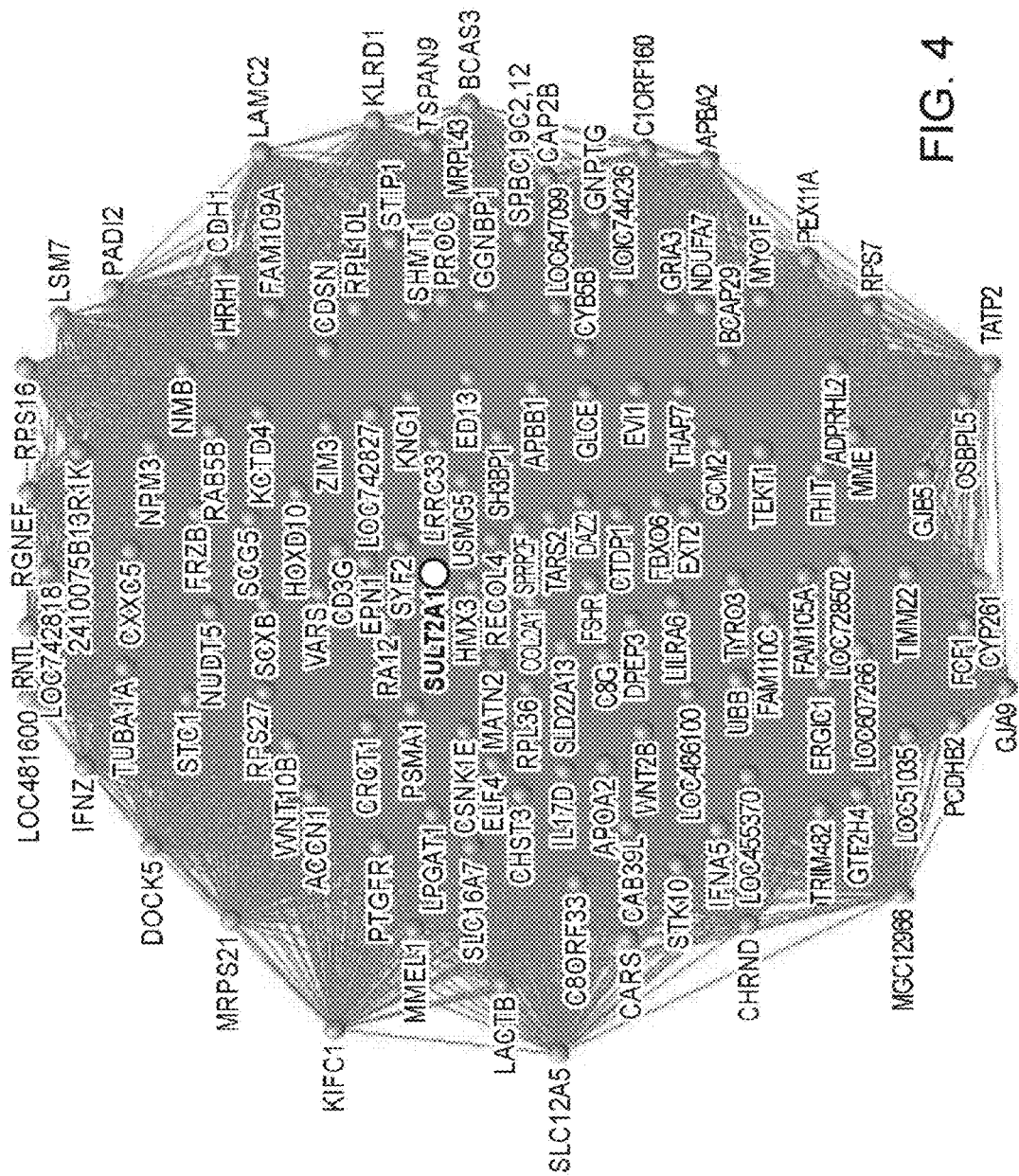
Figure 5A:
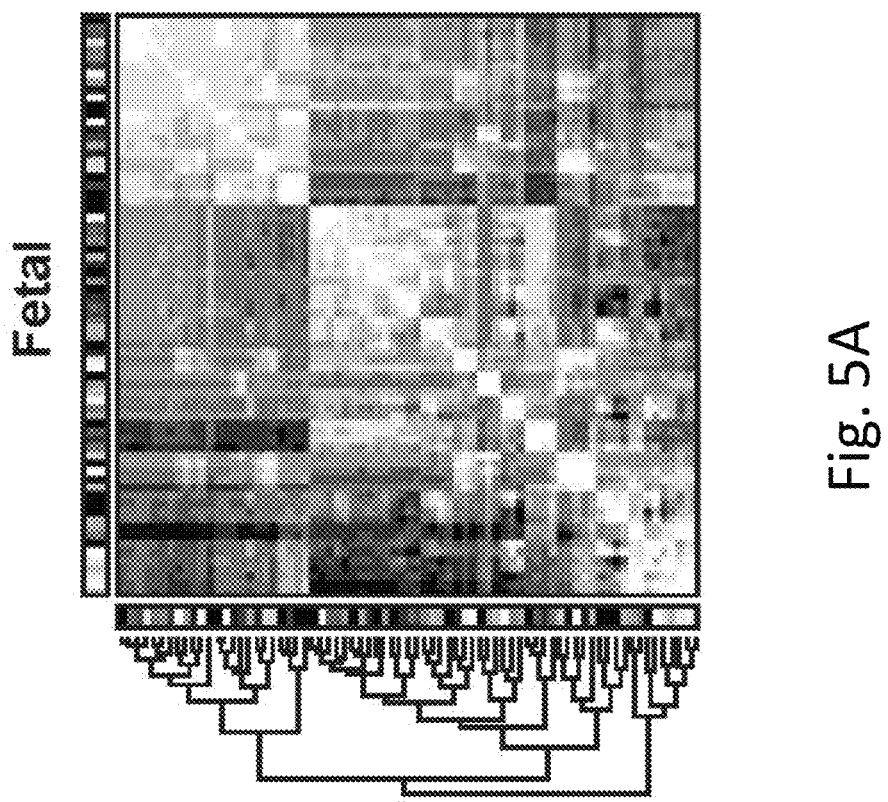
Figure 5B:
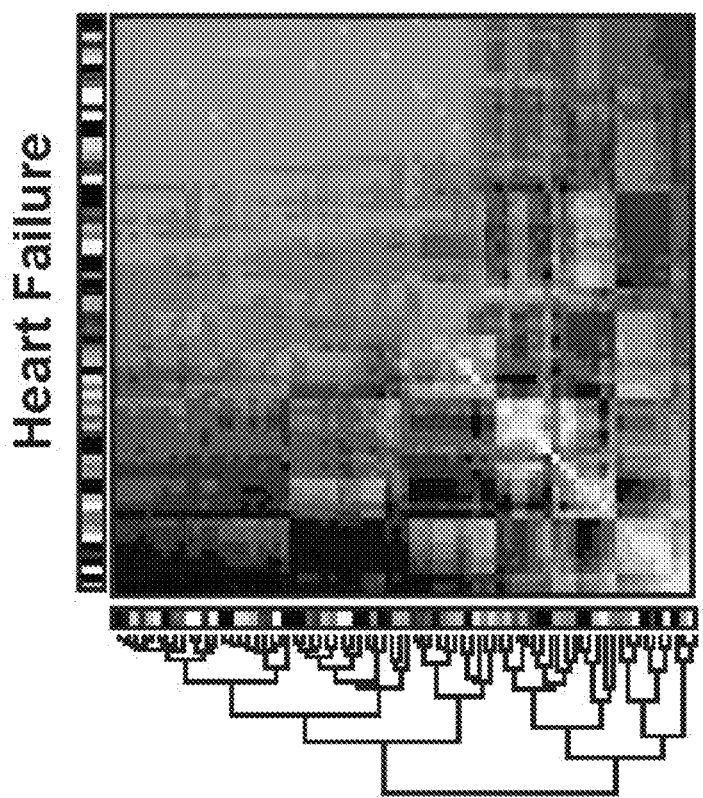
Figure 5C:
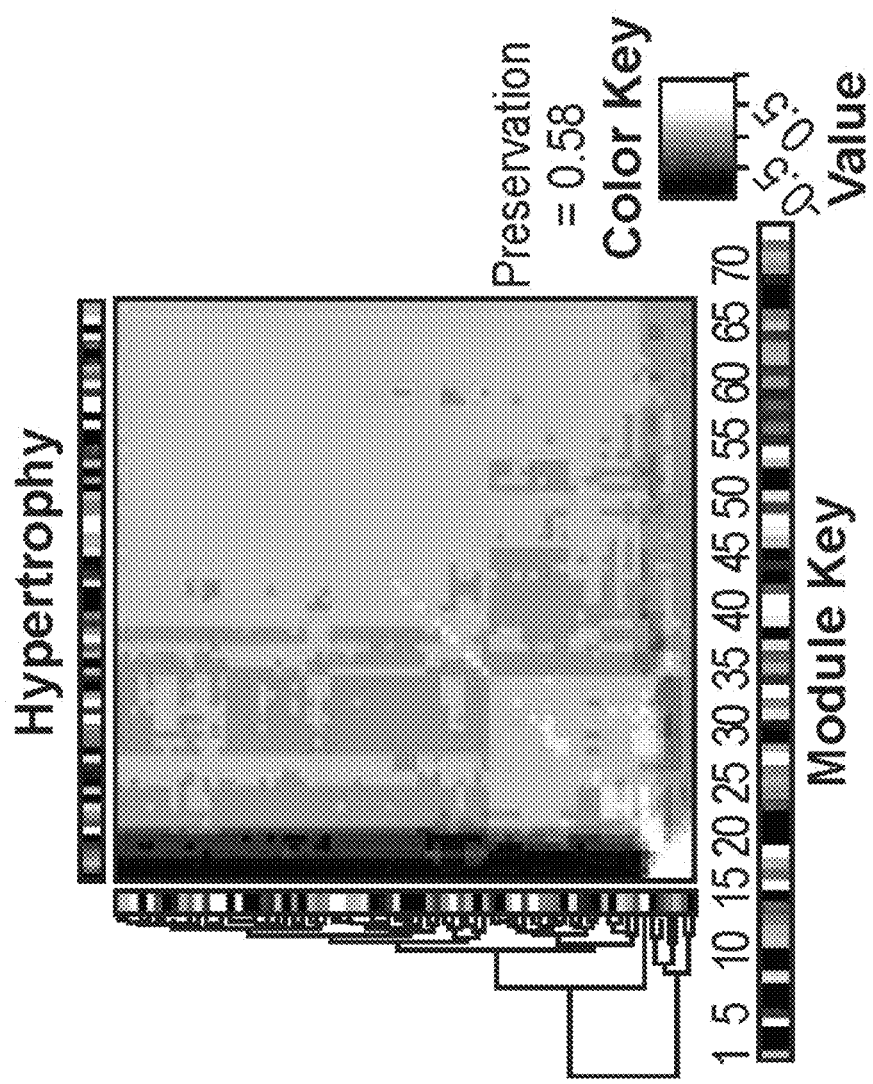
Figure 5D:
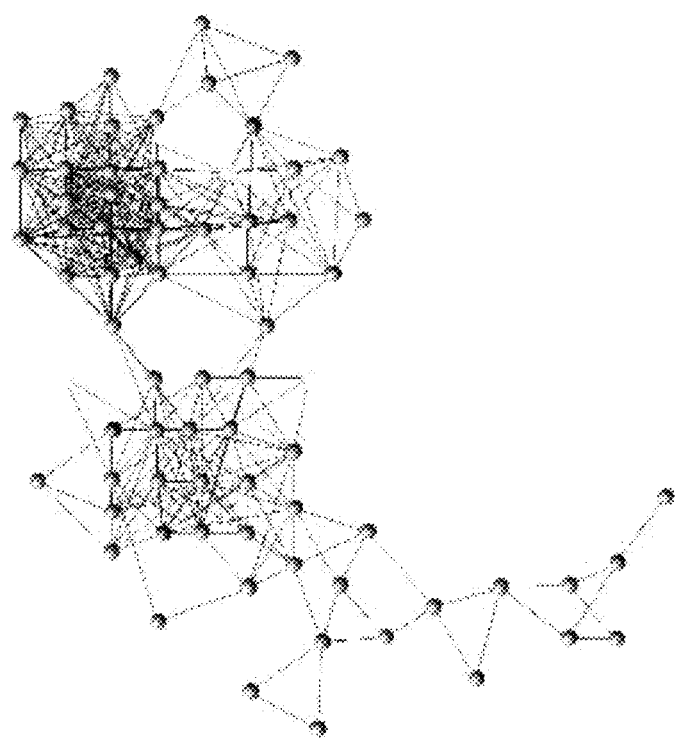
Figure 5F:
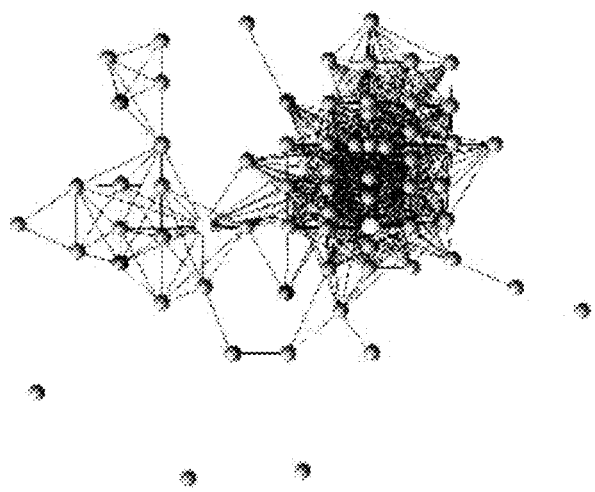

Shown in FIG. 4 is the topology of gene coexpression module common to developing myocardium and hypertrophied and failing myocardium according to an embodiment of the present invention Shown in FIG. 5 are representations of the reproducibility of higher-order network topology between fetal myocardium and myocardium in murine heart failure and cardiac hypertrophy according to an embodiment of the present invention.

Figure 6:
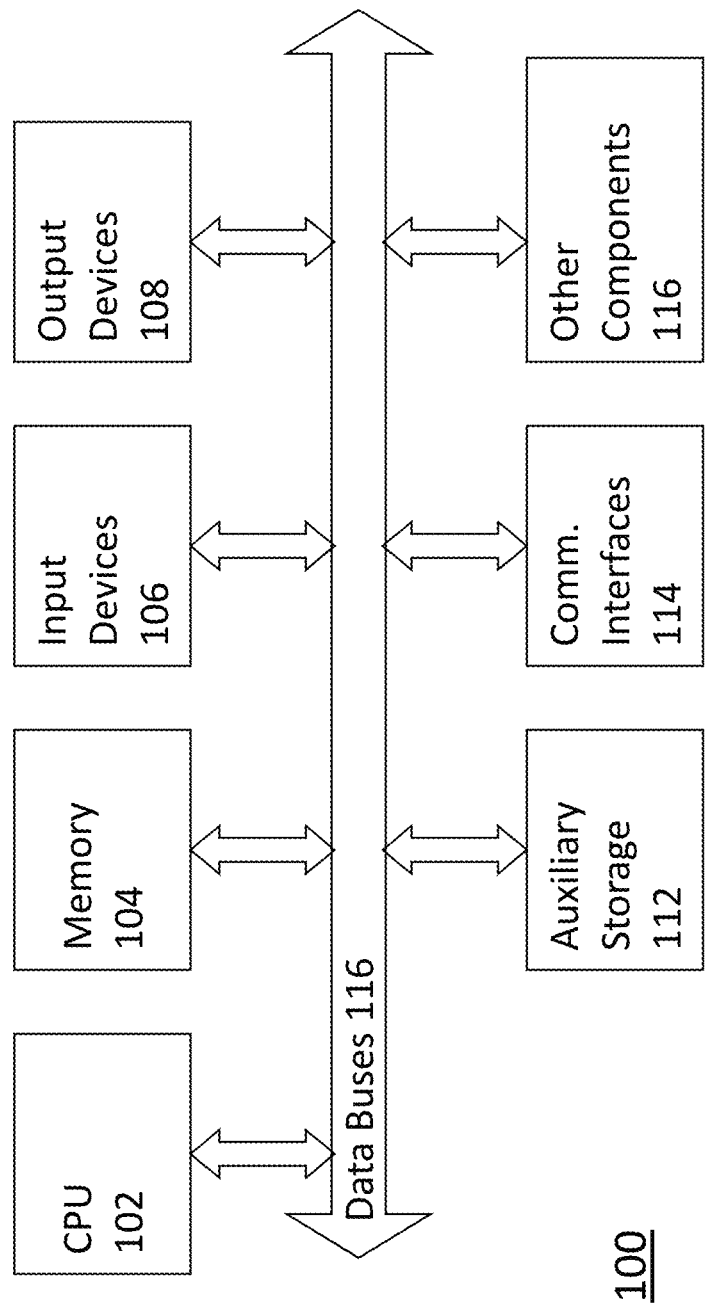
Figure 8A:
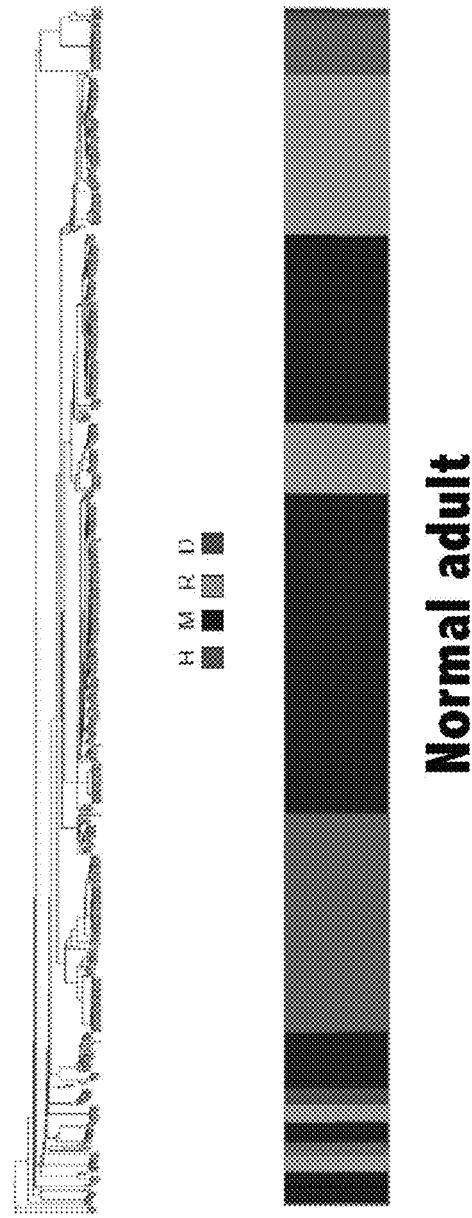
Figure 8B:
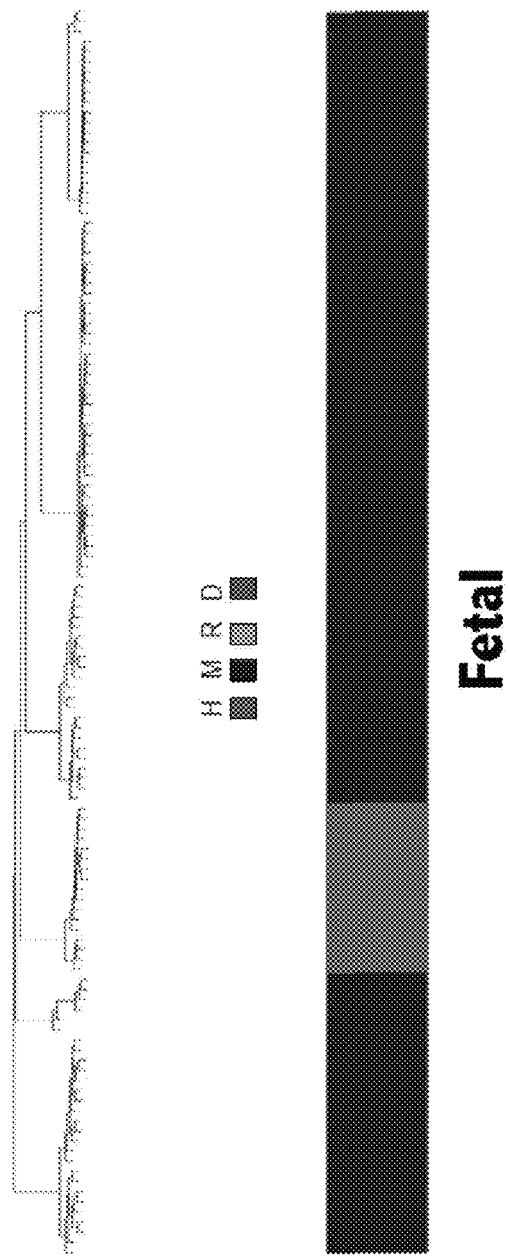
Figure 8C:
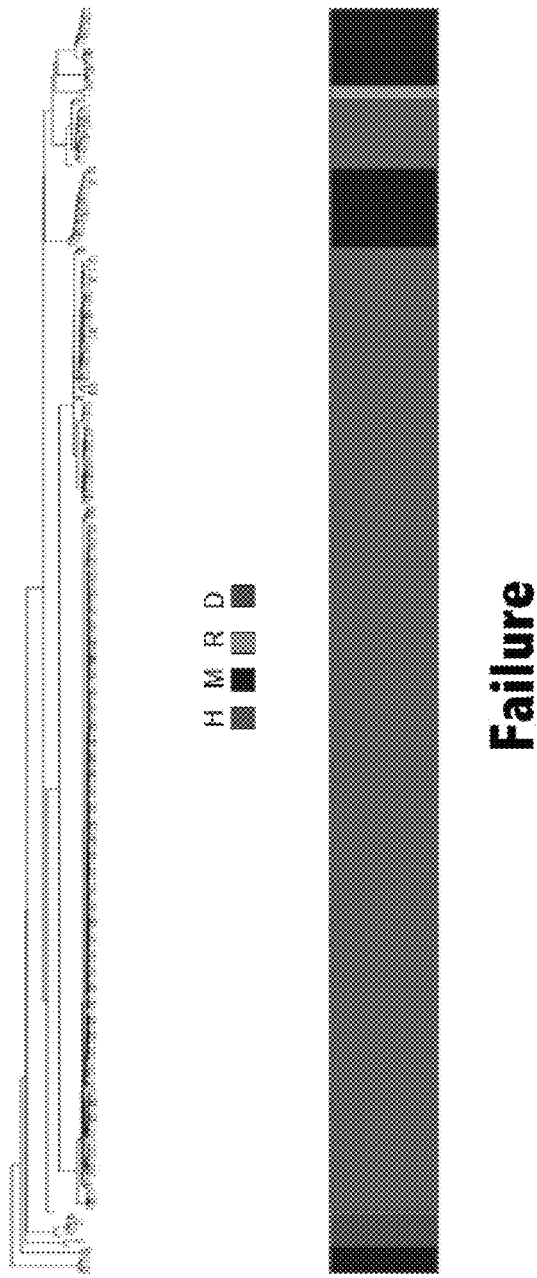
Figure 8D:
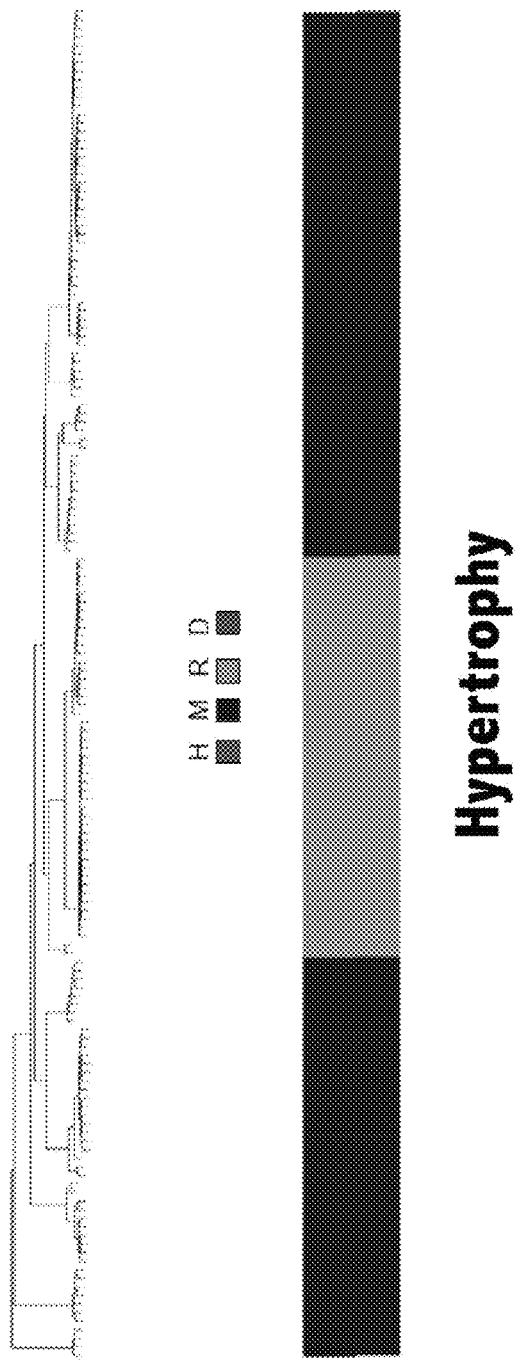

FIG. 6 is a block diagram of a computer system on which the present invention can be implemented.

Shown in FIGS. 7A and 7B are charts demonstrating the normalization of gene expression data using mean absolute deviation method reduces intensity-dependent differences for experiments from different experimental conditions according to an embodiment of the present invention.

Shown in FIGS. 8A-8D are charts that assist in understanding gene expression profiles from different experimental conditions clustered by species according to an embodiment of the present invention.

Shown in FIGS. 9A and 9B are gene coexpression network adjacency soft thresholds for different conditions according to an embodiment of the present invention.

Shown in FIG. 10 are gene coexpression network adjacency soft threshold for different conditions according to an embodiment of the present invention.

Figure 11:
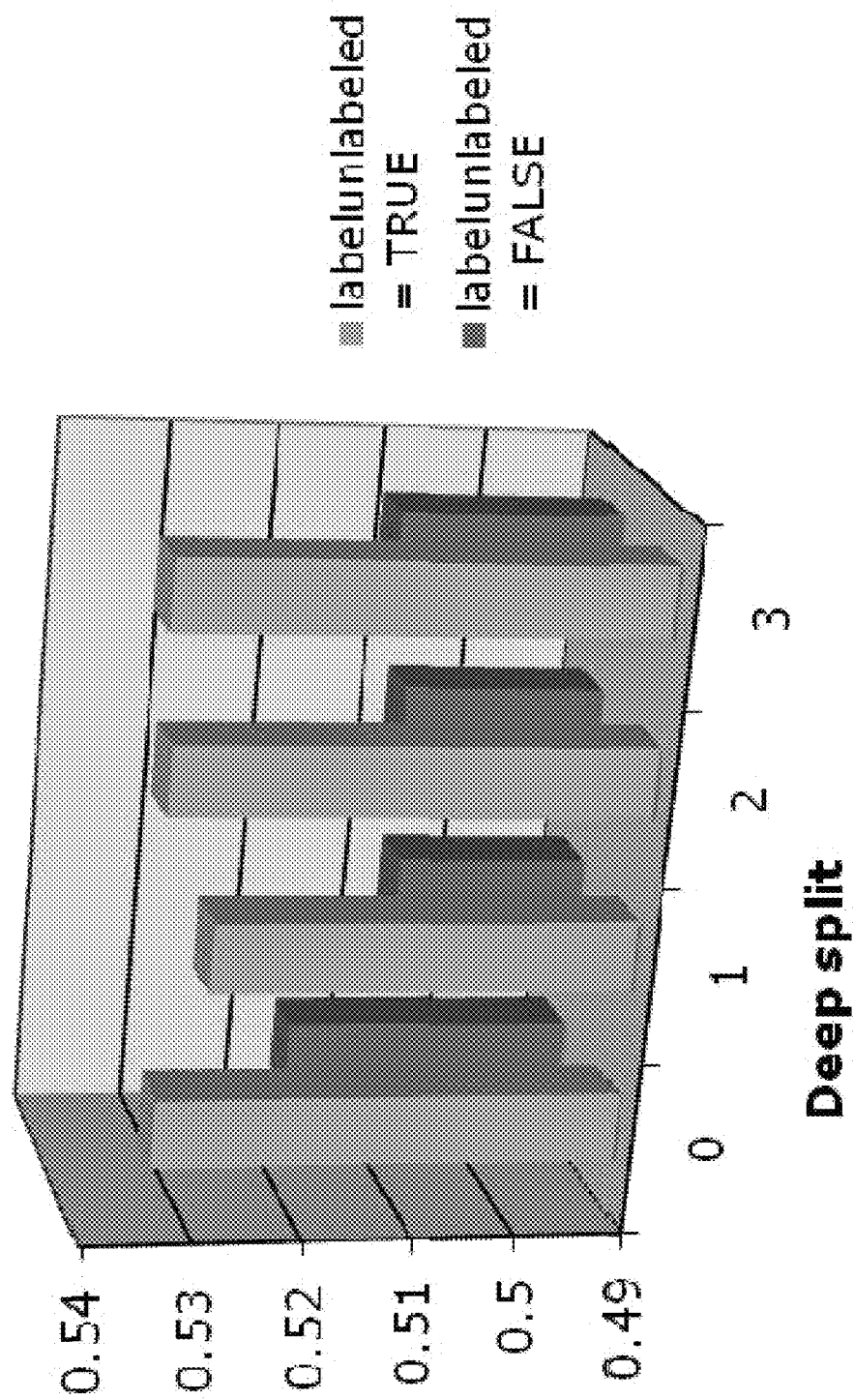

Shown in FIG. 11 is a sensitivity analysis for parameters used in the dynamic tree cut algorithm according to an embodiment of the present invention.

Figure 12A:
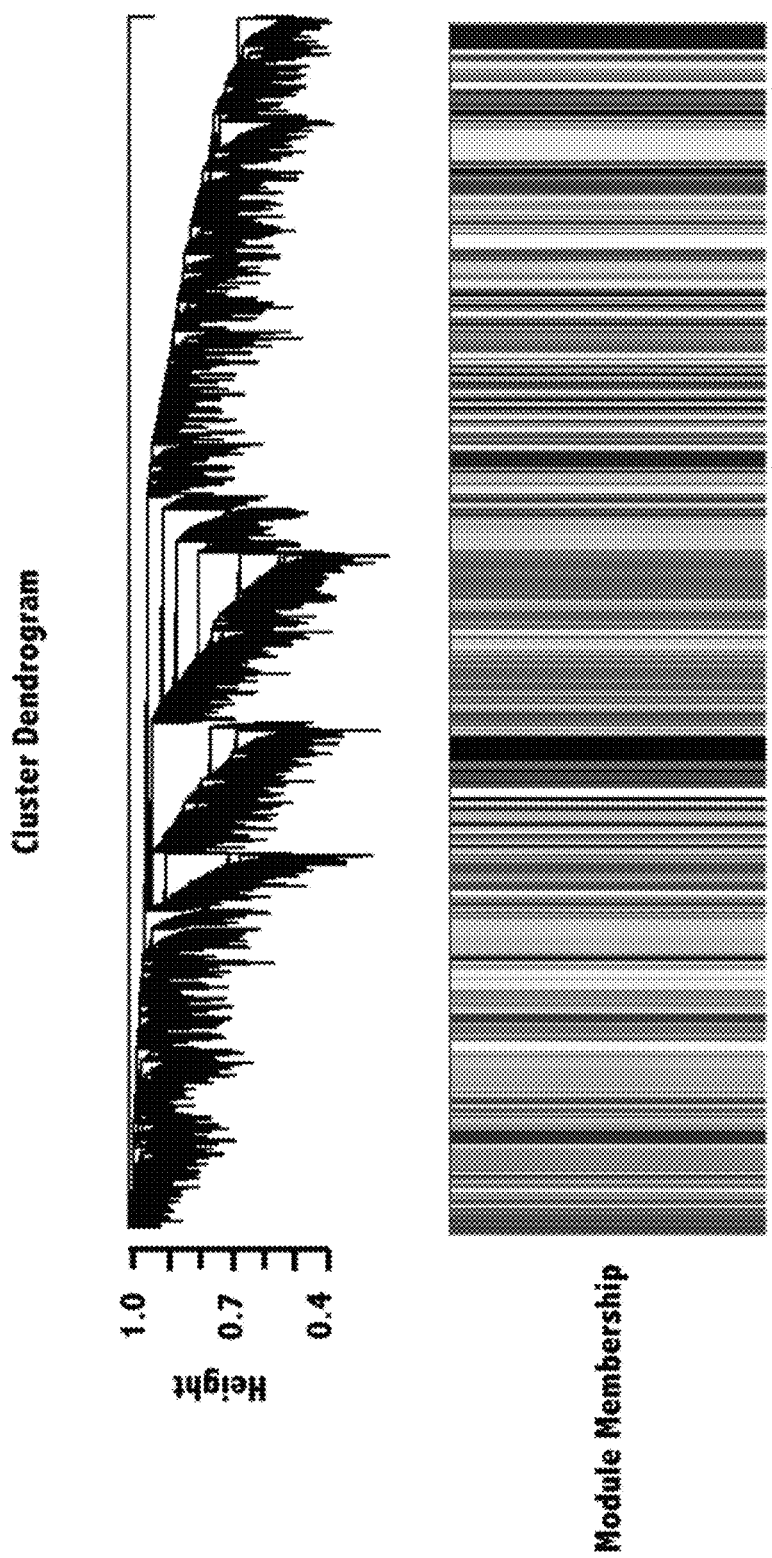
Figure 12B:
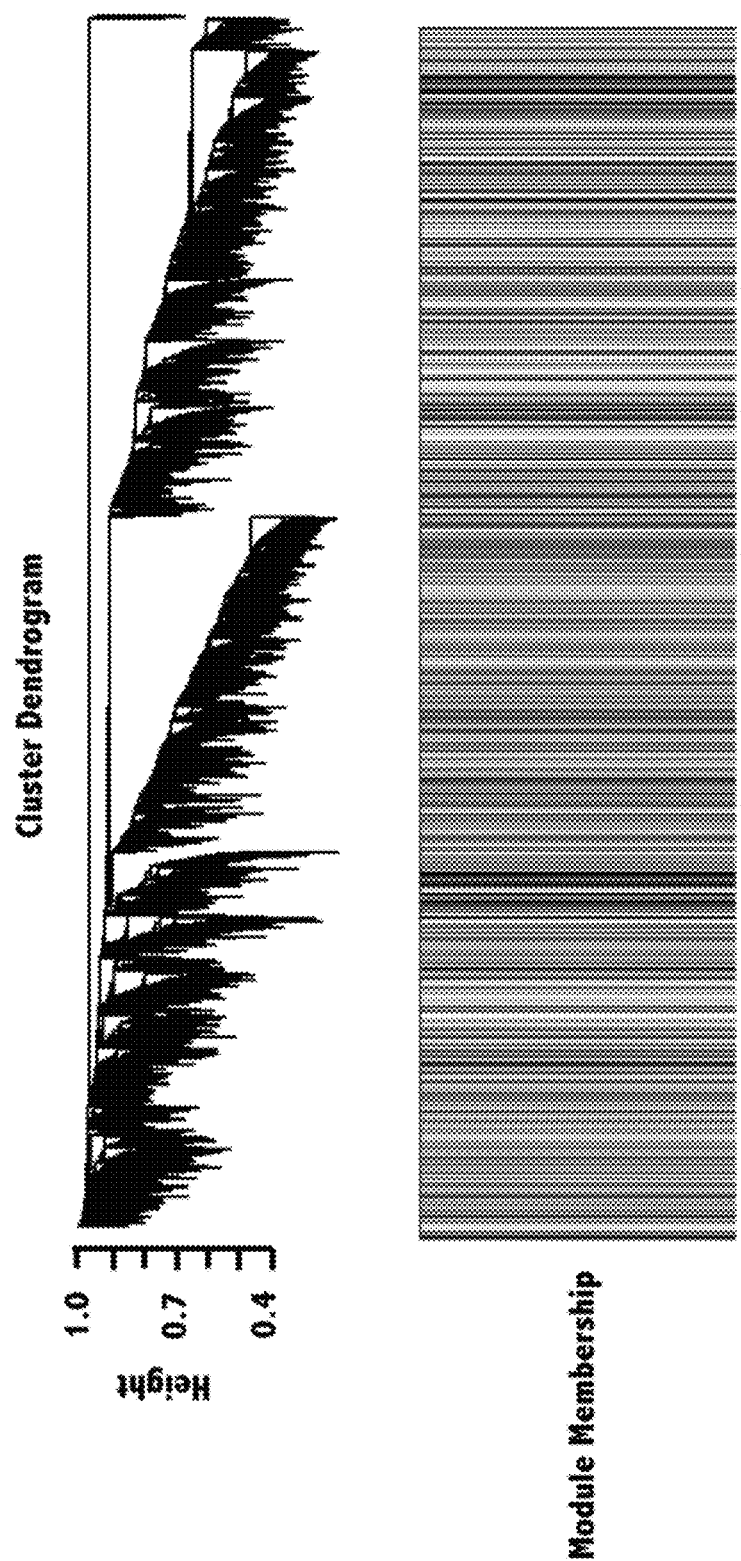
Figure 12C:
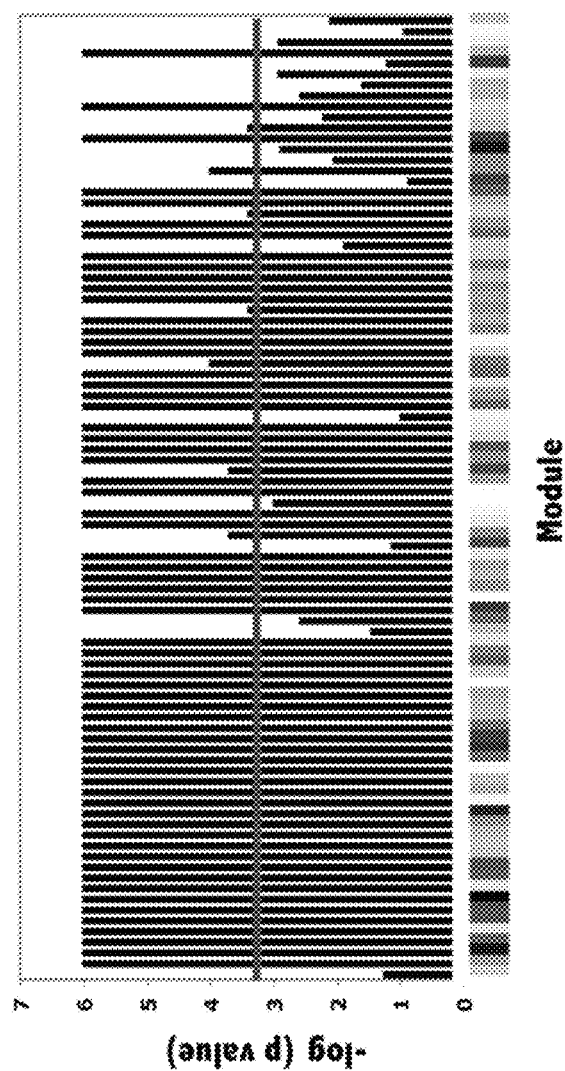

Shown in FIGS. 12A-12C are charts and graphs demonstrating the identification and validation of fetal gene modules according to an embodiment of the present invention.

Figure 13A:
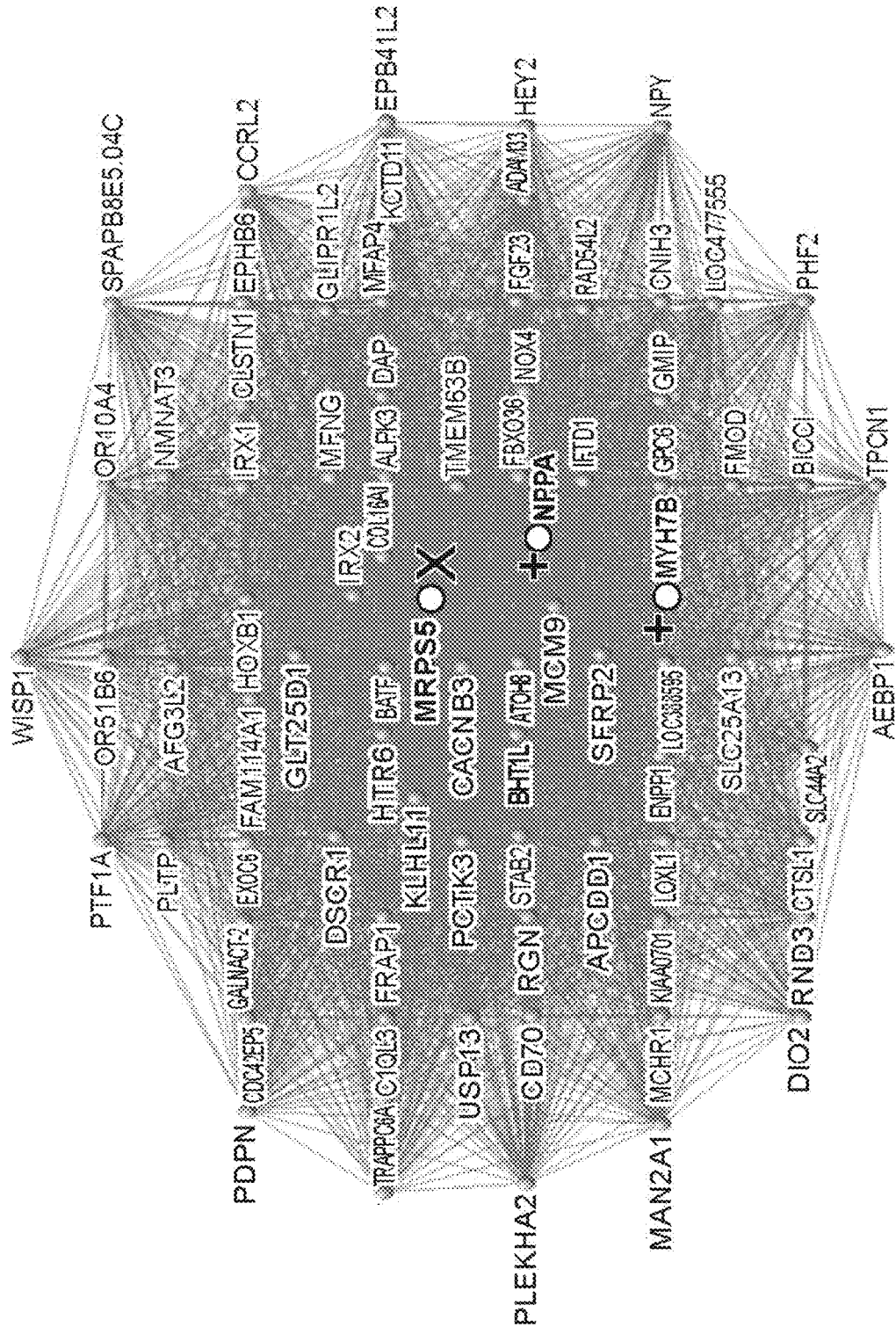
Figure 13B:
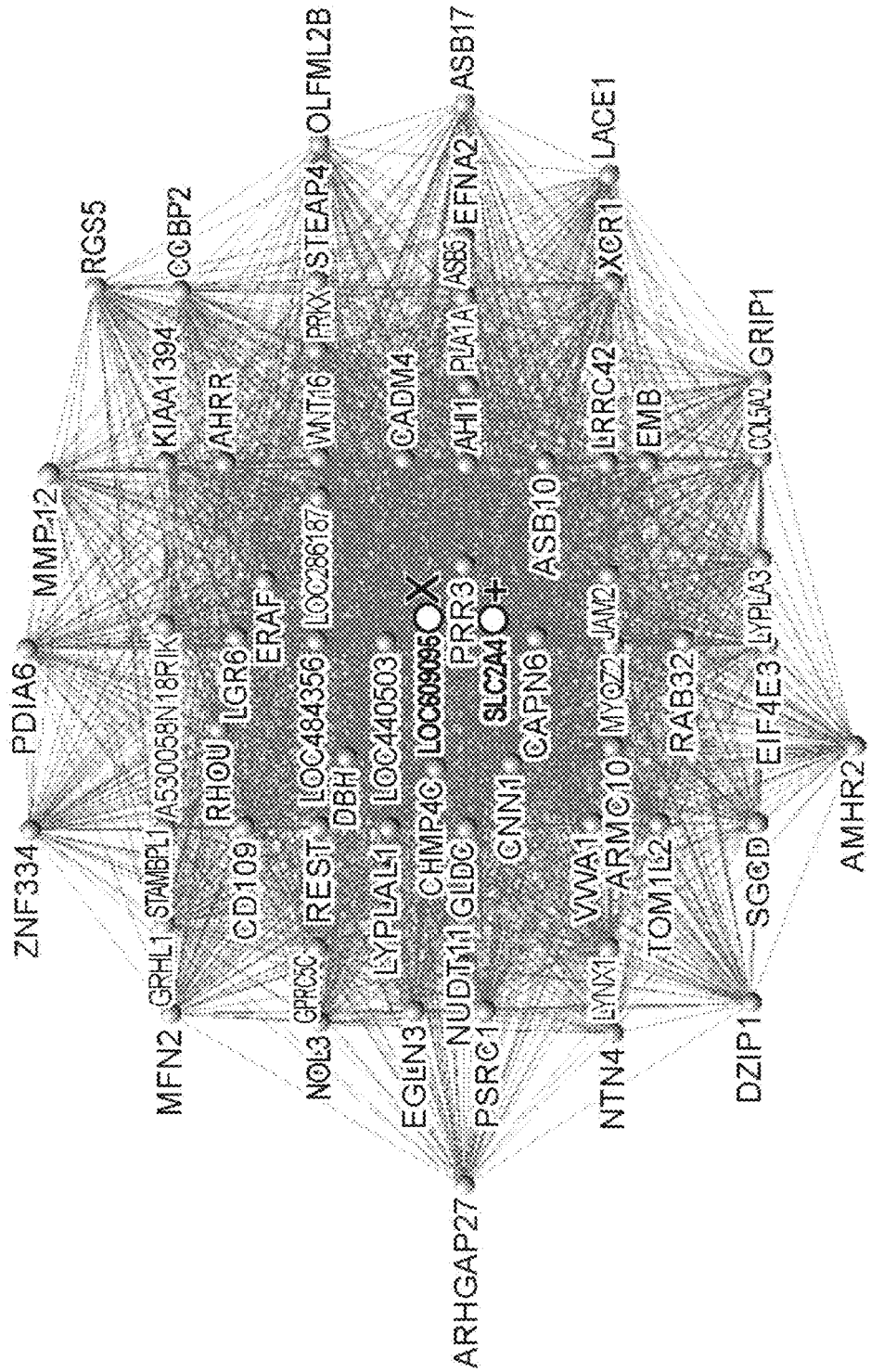

Shown in FIGS. 13A and 13B is a topology of developmental gene coexpression modules containing key marker genes.

FIG. 14 (Table 1) is tabular data regarding over-represented biological processes according to gene ontology (GO) in the fetal module recapitulated in heart failure and hypertrophy according to an embodiment of the present invention.

FIG. 15 (Table 2) is tabular data summarizing genes involved in protein catabolism biological process from fetal module recapitulated in heart failure and hypertrophy according to an embodiment of the present invention.

Figure 16:
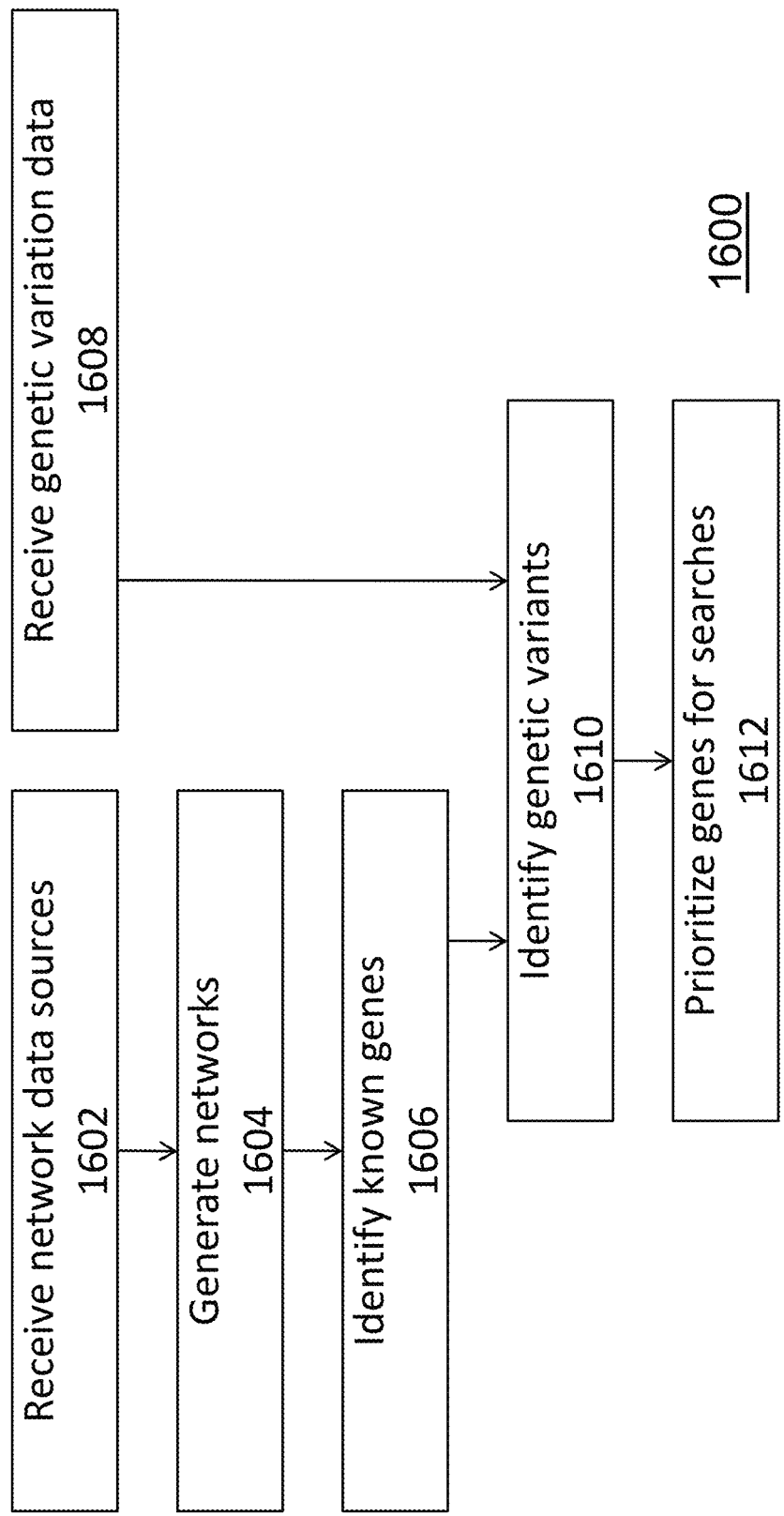

FIG. 16 is a flowchart depicting a method according to an embodiment of the present invention.

Figure 17:
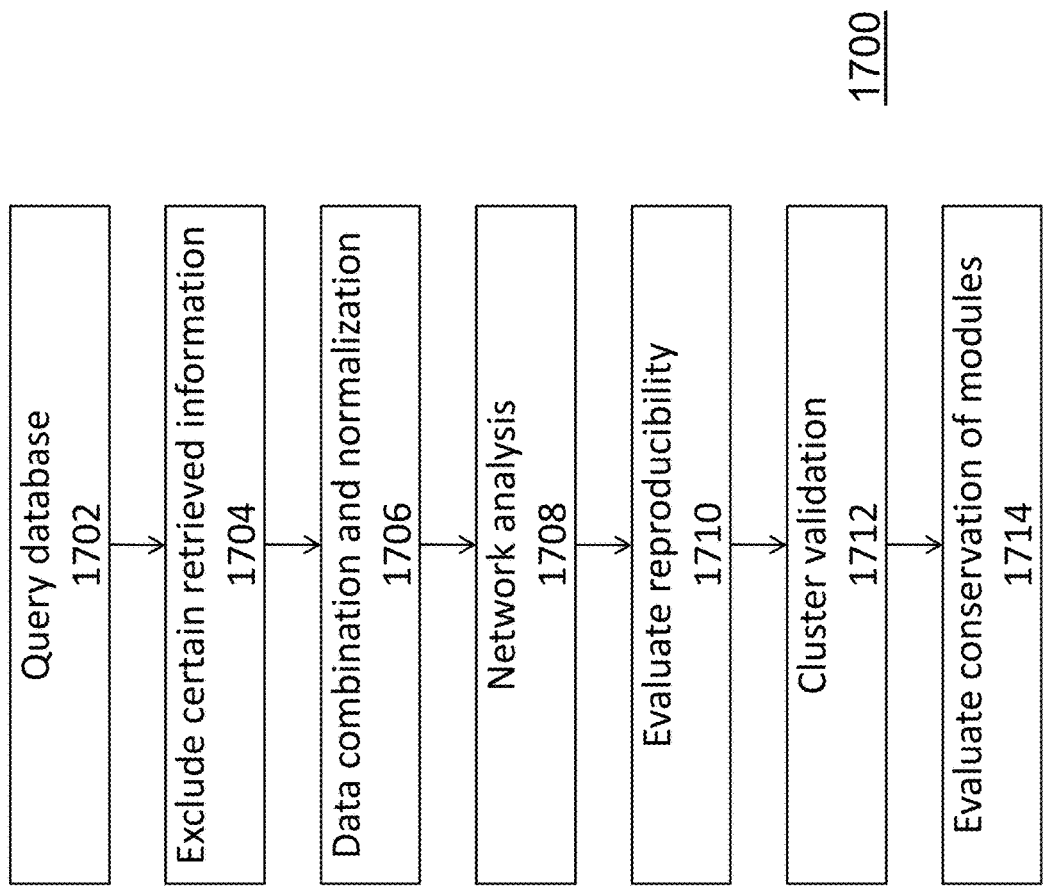

FIG. 17 is a flowchart depicting a method according to an embodiment of the present invention.

DETAILED DESCRIPTION OF THE INVENTION

Among other things, the present invention relates to methods, techniques, and algorithms that are intended to be implemented in a digital computer system 100 such as generally shown in FIG. 6. Such a digital computer or embedded device is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 116 that are intended to allow for communication of the various components of computer system 100. Data buses 116 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the at would be familiar with such details.

Methods

Among other things the present invention includes embodiments for incorporating network modeling to enlarge a search space of candidate genes for known diseases as will be described further below.

Interaction Network Generation Methods

In an embodiment of the present invention, a method is disclosed for generating an interaction network. In an embodiment of the present invention, such an interaction network includes an undirected, weighted graph, G, comprising edges, E, representing connections between vertexes, V, which in turn represent genes or protein products.

Among other things, embodiments of the present invention use data sources for developing interaction networks such as the weighted graph G. A source for such data includes gene expression microarray data from normal and diseased human and mammalian model system tissues. Another source includes targeted genome wide genotyping or sequencing of DNA. Still another source includes sequencing-based mRNA quantification such as RNA-seq. Still other sources include: protein-protein interaction data from yeast two-hybrid experiments, protein co-immunoprecipitation, mass spectrometry; curated gene and protein interaction pathways; semantic text mining of the published literature; and curated miRNA binding site and sequence collections; targeted and comprehensive gene-knockout and knock-down experiments. Many other data sources for interaction networks are possible as would be understood by one of ordinary skill in the art upon understanding the teachings of the present disclosure. Indeed, it can be expected that many other data sources will be developed that can be used in accordance with the teachings of the present invention.

Where quantitative data is available, such as in gene coexpression microarray data or sequence-based mRNA quantification data, pairwise covariance is used in an embodiment to define edges, $E_{ij}$, for all genes or proteins ij in the dataset of interest.

Where qualitative interaction data is available, such as in protein-protein interaction data and curated and semantic text mining data, derived pathway data, e.g., Eij ={0,1}, is conditional on whether a described interaction exists.

In an embodiment of the present invention, communities of links are chosen according to the method of Ahn, et al (Ahn Y, Bagrow J, Lehmann S. Link communities reveal multiscale complexity in networks. Nature. 2010; 466:761-764, herein incorporated by reference for all purposes). This method creates hierarchical, overlapping communities of links using a single link, hierarchical clustering of edges of an unweighted, undirected graph describing the topological overlap between all nodes sharing a common neighbor. In an embodiment, edges can be directed using genotype-gene expression information as a Bayesian prior to inform causality.

Methods For Prioritizing Genes Using Interaction Networks

With a network in hand, such as one described above, a method of the present invention queries such network for known trait-associated genes. For example, in an embodiment of the present invention, genes that are within a predetermined path length from known disease are retained for prioritizing genetic variants. For example, in an embodiment of the present invention genes that have path length≤2 from known disease genes are retained for prioritizing genetic variants discovered using the methods described above for the network.

In an embodiment, genes that co-reside with known disease genes in sub-networks or communities discovered via link clustering are prioritized for searching genetic variants discovered using the network methods described above. Among other things, embodiments of the present invention use data sources for disease gene discovery. A source for such data includes targeted and comprehensive DNA re-sequencing (targeted, whole exome, or whole genome sequencing) in subjects with known or unknown trait phenotypes. Another source includes genotyping arrays. Still other sources includes targeted and comprehensive sequencing based RNA quantification (RNA-seq) and Epigenetic data sources such as chromatin immunoprecipitation and sequencing or genotyping, bisulfite sequencing. Many other data sources for disease gene discovery are possible as would be understood by one of ordinary skill in the art upon understanding the teachings of the present disclosure. Indeed, it can be expected that many other data sources will be developed that can be used in accordance with the teachings of the present invention.

In another embodiment, prior probabilities or expectations of pathogenicity of discovered variants are updated according to co-residence in shared sub-networks with disease genes ("guilt by association"). In yet another embodiment, these prior probabilities/expectations are used to update existing prior probabilities based on amino acid change, evolutionary conservation, co-segregation with trait phenotype or enrichment. Among other things, in an embodiment of the present invention, these prior expectations can be used for discrete filtering. Also, in another embodiment, prior probabilities in a Bayesian model of likely pathogenicity for each variant discover in a sequencing project can be generated.

Shown in FIG. 16 is an embodiment of a method according to the present invention. As shown, at step 1602, network data sources are received. In an embodiment of the present invention this includes gene expression microarray data from normal and diseased human and mammalian model system tissues. Another source includes targeted genome wide genotyping or sequencing of DNA. Still another source includes sequencing-based mRNA quantification such as RNA-seq. Still other sources include: protein-protein interaction data from yeast two-hybrid experiments, protein co-immunoprecipitation, mass spectrometry; curated gene and protein interaction pathways; semantic text mining of the published literature; and curated miRNA binding site and sequence collections; targeted and comprehensive gene-knockout and knock-down experiments. Many other data sources for interaction networks are possible as would be understood by one of ordinary skill in the art upon understanding the teachings of the present disclosure. Indeed, it can be expected that many other data sources will be developed that can be used in accordance with the teachings of the present invention.

From the network data sources, networks of interest are generated at step 1604. Such networks can be generated as generally described above, as described more fully further below, or according to compatible methods known to those of ordinary skill in the art.

From the generated network, at step 1606, known genes are identified. Among other things, in an embodiment of the present invention, known disease genes are also identified. Sources for known disease genes include curated sets of genes associated with Mendelian disorders. Another source of known disease data includes sets of genes discovered in complex trait, common phenotype associations (e.g., genome-wide association studies, candidate gene studies, and targeted re-sequencing discovery using exome and whole genome sequencing data). Many other data sources for known disease genese are possible as would be understood by one of ordinary skill in the art upon understanding the teachings of the present disclosure. Indeed, it can be expected that many other data sources will be developed that can be used in accordance with the teachings of the present invention.

At step 1608, genetic variation data is received. It should be noted, however, that the method 1600 of FIG. 16 as well as other methods described in the present disclosure are not necessarily intended to be performed in the order presented. Indeed, those of ordinary skill in the art would understand that certain steps can be performed before or after certain other steps. Moreover, those of ordinary skill in the art will understand that certain steps of the methods described herein can be performed in a pipelined or parallel fashion. Indeed, certain of the steps of the present invention can be performed using computational techniques where there order can be a combination of serial and parallel processing.

Using the genetic variation data as well as the identification of known diseases, genetic variants are identified at step 1610 that are in close proximity to known trait genes. In an embodiment of the present invention, genes that have a path length within a predetermined range are identified. In an embodiment, the predetermined range is a path length≤2 from known disease genes.

At step 1612, in an embodiment of the present invention, identified genes are prioritized for searching genetic variants. For example, in an embodiment of the present invention, genes that co-reside with known disease genes in sub-networks or communities discovered via link clustering are prioritized for searching genetic variants discovered using methods for disease gene discovery, for example.

Using known interactions in a curated compendium of disease-gene interactions, a method according to an embodiment prioritizes genome-wide genetic variants or gene products relevant to Mendelian disease according to their impact and actionability as a scaffold.

In an embodiment, the expanded set of putative disease genes is used in annotation of whole genome sequences to restrict the search space for variants with causal implications in inherited disease syndromes. For example, in an embodiment, variants in known coding (exons) regions are annotated according to predicted pathogenicity to prioritize genome-wide genetic variants or gene products relevant to Mendelian disease according to their impact and actionability and variants in important non-coding regions (splice sites, 5' and 3' un-translated regions, microRNA targets and miRNA sequences targeting the gene, enhancers, promoters, and repressors) are identified.

Applications

Population wide sequencing is a near-term reality, and the ability to interpret genome sequences from individuals will determine the commercial viability of this technology for advancing personalized health care. Embodiments of the present invention provide solutions for identifying candidate disease genes in individuals with inherited disease syndromes, and also for identification of risk alleles and carrier states in disease genes in healthy individuals.

Among other things, the present invention can be used for mapping causal gene loci in inherited disease syndromes using whole genome sequence data. The present invention can also be used for creating disease and carrier state predictions from whole genome sequencing of healthy individuals as part of a genome sequence interpretation pipeline. Also, embodiments of the present invention can be used for identifying targets for research on the pathophysiology of inherited disease syndromes. The teachings of the present invention can also be used for prioritization of genes for designing capture-based sequencing platforms and hybridization-based genotyping technologies for rapid molecular diagnosis of inherited disease syndromes. Many other applications are possible as would be understood by those of ordinary skill in the art.

Alternative Embodiments

Variations for the methods of the present invention are many. For example, hierarchical link clustering as implemented in embodiments of the present invention can be computationally intensive. To address this issue, hierarchical clustering of genes based on topological overlap can be implemented where topological overlap is a similarity measure that captures the degree of shared network neighbors. Also, based on results of "leave-one-out" cross-validation approach, the threshold for step length (degree of separation between network neighbors) in identification of genes related to known disease genes can be modified. Also, clustering clinical phenotypes based on shared genetic and clinical features can be implemented so as to enlarge the starting scaffold set of disease genes.

Network Methods

Embodiments of the present invention use network analysis techniques to allow for more accurate reflection of underlying systems biology to be realized than traditional unidimensional molecular biology approaches. So as to provide an example of network analysis and its development for use in other embodiments of the present invention, a concrete example will be provided further below where, using gene coexpression network analysis, a gene expression network topology of cardiac hypertrophy is developed.

Shown in FIG. 17 is a flowchart depicting a method 1700 for network analysis according to an embodiment of the present invention. As shown, at step 1702, a database was queried using terms of interest. In an embodiment of the present invention, the database contains all microarray data that are presented in the published literature. In other embodiments, different databases can be used. In an embodiment of the present invention to be described further below, the terms heart, myocardium, and cardiovascular to obtain all datasets describing microarray experiments involving myocardial tissue. In other embodiments, the search terms would vary according to the specific application. At step 1704, certain retrieved information may be excluded according to the qualities of the information that is retrieved.

At step 1706, data combination and normalization is performed. In an embodiment, this step allows for the comparison of gene expression data between different platforms and experimental conditions. Next, at step 1708, weighted gene coexpression network analysis is performed. In an embodiment, this is done to identify groups of genes with similar patterns of expression across experimental samples. These groups of genes are also called modules.

At step 1710, the reproducibility of modules is then evaluated. In an embodiment, this is done by calculating the extent of intramodular connectivity preservation. Afterwards, at step 1712, cluster validation is performed.

In an embodiment of the present invention addressing cardiac issues, at step 1714, conservation of fetal modules was evaluated. In an embodiment, random permutation are used to assess the reproducibility of fetal modules in normal adult datasets.

A transcription factor analysis is performed at step 1616. In an embodiment, gene coexpression modules were analyzed for over-representation of known transcription factor targets. At step 1618, scaled gene expression profile modules are summarized. In an embodiment, a first singular vector (called an eigengene) is used for this step. The eigengene has been found to be equivalent to the first principal component and explains the largest proportion of variance of the module genes.

Details of method 1600 will be described in the further description below in conjunction with the figures. The network analysis techniques described below will, however, also be applicable to the methods and embodiments described further above.

Data Acquisition and Normalization

The Gene Expression Omnibus (GEO) is a publicly available repository of all microarray data that are presented in the published literature. This database was queried using the terms heart, myocardium, and cardiovascular to obtain all datasets describing microarray experiments involving myocardial tissue (n=2546). Because absolute expression data is required for weighted gene coexpression network analysis, log transformed dual dye datasets were excluded (n=43). Of these datasets, 1617 contained information regarding experimental conditions, species and a phenotype identifiable as developmental (fetal or post natal days 0 to 10 without experimental manipulation of myocardium), normal adult (adult tissue with no experimental manipulation of myocardium), hypertrophy (histologically or anatomically identifiable cardiac hypertrophy), or heart failure (clinical syndrome of heart failure and impaired cardiac systolic and/or diastolic dysfunction).

Data combination and normalization was performed to allow comparison of gene expression data between different platforms and experimental conditions. So as not to distract from the present teachings, further details of an embodiment for data combination and normalization are included in a Supplementary Methods section below.

Summary statistics showing minimization of bias with this method of normalization are provided in FIG. 7. As shown in FIG. 8, gene array experiments clustered by species, suggesting a species dependency for gene coexpression. Therefore, the present analysis focuses on the species with the most complete dataset, choosing the 757 arrays performed in mouse myocardium. An additional 255 experiments involved transgenic deletion, insertion, or mutation of genes important to myocardial function and/or myocardial gene expression and were thus excluded. As physiological hypertrophy is a state distinct from pathological hypertrophy that does not progress to heart failure, 24 datasets describing hysiological hypertrophy induced by chronic exercise were excluded (see FIG. 1). The final dataset contained 12,620 genes represented in 478 samples.

Figure 1:
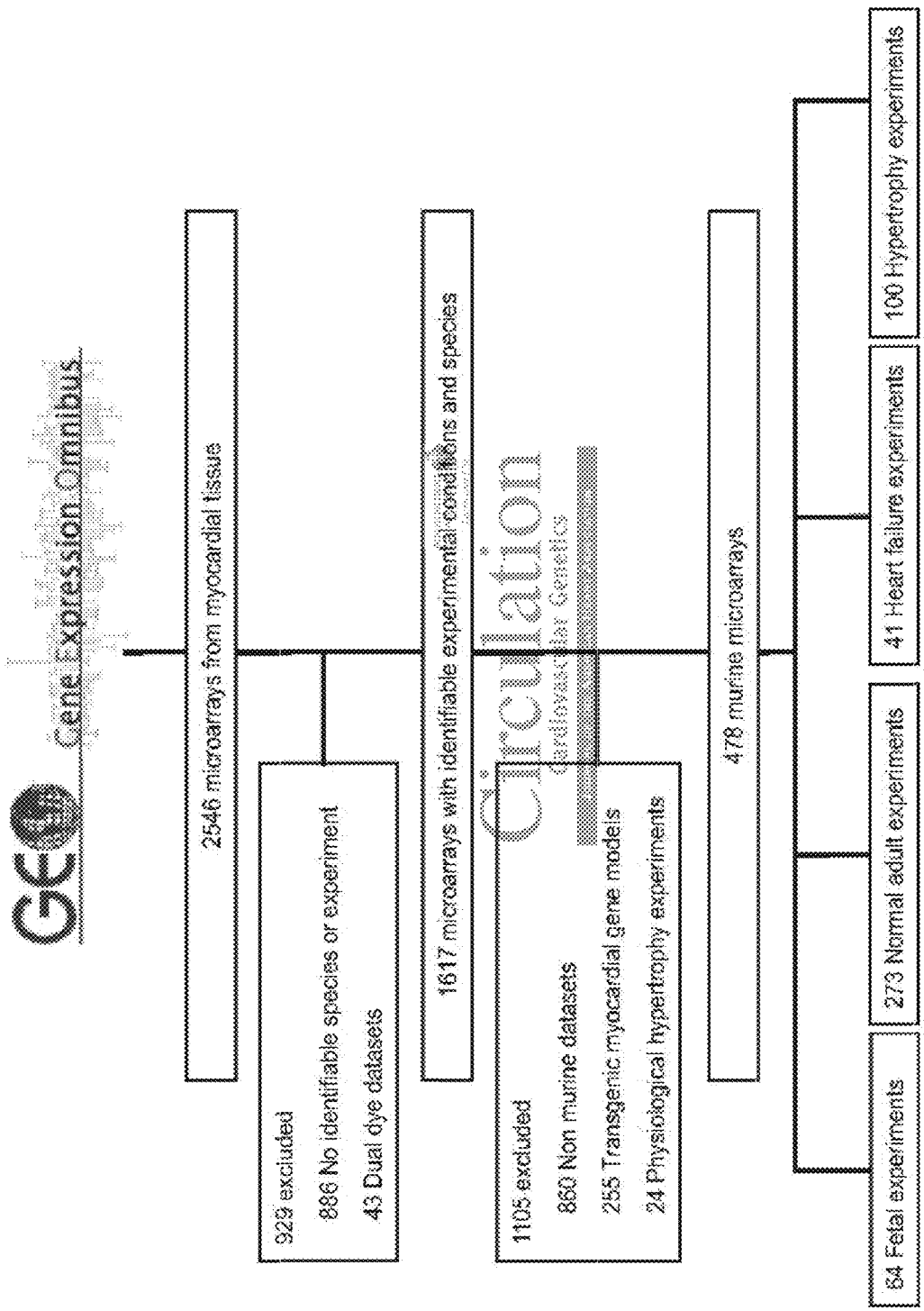
FIG. 1 is a chart showing myocardial gene microarray expression data used in an embodiment of the present invention.

FIG. 1 shows myocardial gene microarray expression data used in an embodiment of the present invention. As shown, all murine microarray data from the Gene Expression Omnibus (GEO) database were queried with the search terms heart, myocardium, and cardiovascular.

Weighted Gene Coexpression Network Analysis

Weighted gene coexpression network analysis was performed to identify gene coexpression modules, that is, groups of genes with similar patterns of expression across experimental samples (Zhang B, Horvath S. A general framework for weighted gene co-expression network analysis. Stat Appl Genet Mol Biol. 2005; 4:Article17). Gene coexpression networks are defined in this work as a weighted graph in which genes are represented as vertices and connections strengths, or adjacencies, are represented as edges between vertices. These gene modules were first identified in fetal myocardial tissue, and their reproducibility was evaluated in normal adult, hypertrophied, and failing myocardial tissue samples. Gene modules were derived in a training set of 43 randomly chosen fetal samples (67% of all fetal samples). The remaining 21 fetal samples used for module validation were not used for this initial module identification. To carry out module detection, agglomerative hierarchical clustering of adjacencies given by the topological overlap measure was used. The topological overlap measure is a network adjacency based on shared network neighbors, which is in turn based on weighted Pearson correlation between gene expression profiles. This network adjacency is robust to noise and amplifies connectivity patterns in sparse networks (Yip A M, Horvath S. Gene network interconnectedness and the generalized topological overlap measure. BMC Bioinformatics. 2007; 8:22). Separate adjacencies were constructed for each phenotype considered. To cut branches of the tree into gene modules, the dynamic tree cut algorithm was used which iteratively searches for stable branch size and chooses clusters based on the shape of each tree branch (Langfelder P, Zhang B, Horvath S. Defining clusters from a hierarchical cluster tree: the Dynamic Tree Cut package for R. Bioinformatics. 2008; 24:719-720). This algorithm allows manipulation of several parameters controlling resultant cluster size and cohesiveness; sensitivity analysis was performed for each of these parameters. The modules from the fetal network were then carried forward for all subsequent analysis. Intramodular connectivity kin was defined for each gene as the sum of adjacencies with all other genes in the module to which it was assigned. A hub gene was then identified for each module as the gene with the single greatest kin. Module composition was further assessed according to defined gene ontologies (GO) using the DAVID analysis tool (Huang da W, Sherman B T, Lempicki R A. Systematic and integrative analysis of large gene lists using DAVID bioinformatics resources. Nat Protoc. 2009; 4:44-57; Dennis G, Jr., Sherman B T, Hosack D A, Yang J, Gao W, Lane H C, Lempicki R A. DAVID: Database for Annotation, Visualization, and Integrated Discovery. Genome Biol. 2003; 4:P3). All p values reported for GO analysis were corrected for multiple comparisons using the Benjamini correction and both corrected and uncorrected p values are reported. Networks were visualized using the visANT network visualization tool (Hu Z, Hung J H, Wang Y, Chang Y C, Huang C L, Huyck M, Delisi C. VisANT 3.5: multiscale network visualization, analysis and inference based on the gene ontology. Nucleic Acids Res. 2009; 37:W 115-21).

Evaluating Reproducibility of Gene Modules

To evaluate reproducibility of modules between networks, the extent of intramodular connectivity preservation was calculated. To this end, for each module, the correlation $M_{pres}=cor(k^l,k^m)$ between intramodular connectivity vectors $k^l$ and $k^m$ was calculated. These vectors described intramodular connectivities kin for genes within each module across two networks $N_l$ and $N_m$. The closer $M_{pres}$ is to 1, the better preserved is the module structure across networks $N_l$ and $N_m$. An iterative significance test was used to assign a p value to this measure of module reproducibility between networks $N_l$ and $N_m$. The null hypothesis for this significance test was that derived modules were preserved between networks $N_l$ and $N_m$ no better than modules derived from random clustering. To evaluate this hypothesis, gene module identifiers were randomly permuted such that gene modules of the same size but random gene composition were generated. Ten thousand such permutations were performed and $M_{rand}$, the module preservation of each random module assignment, was calculated for each permutation. The probability of the null hypothesis p was then calculated as the proportion of permutations in which the preservation of random modules between networks $N_l$ and $N_m$ was greater than that of derived modules ($M_{rand}>M_{pres}$). This significance test was used for module internal validation and evaluation of fetal module reproducibility in adult normal, failing, and hypertrophied myocardial tissue.

Cluster Validation

Clusters were first internally validated in 21 samples not used for module derivation. To prevent spurious inference of association from repeated sampling across the set of gene modules, the Bonferroni correction was employed in each comparison to determine significance of p values derived via permutation derived significance testing described above. Thus, module internal validity was inferred from a p value of less than $5.5 \times 10^{-4}$ for 90 comparisons.

Conservation of Fetal Modules in Normal Adults, Heart Failure, and Hypertrophy

Random permutation was again used to assess the reproducibility of fetal modules in normal adult datasets. Modules with $p>6.9 \times 10^{-4}$ (corrected for 72 comparisons) were defined as specific to fetal tissue. To identify additional modules with conserved topology but significant differential expression between fetal and normal adult myocardium, significance analysis of microarrays was used to evaluate gene-wise differential expression between fetal and normal adult myocardium (Storey J D, Tibshirani R. Statistical methods for identifying differentially expressed genes in DNA microarrays. Methods Mol Biol. 2003; 224:149-157). A d-score was assigned to each gene that quantified the significance of its differential expression between phenotypes. For each module, an average d score was calculated by dividing this aggregate d score by the number of genes in the module. A p value was assigned to this average d score via a permutation-derived significance test. The p value for each average modular d score was given by the proportion of ten thousand permutations in which random gene modules of the same size were associated with a greater average d score than derived clusters. Significant modular differential expression was inferred from p<0.002 (corrected for 26 comparisons). This set of modules together with the set of modules with topology specific to fetal tissue was thus defined as the "fetal gene program" and evaluated further for reproducibility in hypertrophied and failing myocardial tissue using the iterative module reproducibility algorithm described above. Fetal module reproducibility in heart failure and hypertrophy was inferred from a p value of 0.001 for 50 comparisons.

Transcription Factor Analysis

Gene coexpression modules were next analyzed for overrepresentation of known transcription factor targets. Each gene g was linked to a transcription factor if it was identified as a target of that transcription factor. For each transcription factor t in each co-expression module, the hypothesis that transcription factor t was over-represented in the list of genes comprising the module when compared to what was expected by chance alone was tested. This association was measured using the hypergeometric distribution as the probability of observing k or more genes targeted by t transcription factors in the set of n genes, when there are K genes targeted by transcription factor t in the whole set of N genes. Given that 56 total transcription factors were analyzed in the module shared between fetal and hypertrophied and failing myocardium, significance of association was inferred from a p value less than $9 \times 10^{-4}$.

Module Membership of Key Genes and Higher Order Topology of Fetal Gene Transcriptome To summarize the scaled gene expression profiles modules, the first singular vector (referred to as the module eigengene) that resulted from singular value decomposition was used. The module eigengene is equivalent to the first principal component and explains the largest proportion of the variance of the module genes. Based on the correlations between the module eigengenes of different modules, an eigengene network was constructed that can be used to assess higher order topology of gene coexpression (Langfelder P, Horvath S. Eigengene networks for studying the relationships between co-expression modules. BMC Syst Biol. 2007; 1:54). In this way the gene coexpression network was reduced from thousands of genes to several representative eigengenes that in turn form nodes in a meta-network describing higher-order topology of the transcriptome. Similar eigengenes were calculated for modules in hypertrophied and failing myocardium. To evaluate higher-order reproducibility of fetal gene modules in myocardial adaptation, an adjacency matrix was calculated for eigengene networks in each phenotype considered via the Pearson correlation between eigengenes across all microarrays representing each phenotype. Preservation of inter-modular connections was then assessed via the preservation density, which was calculated as follows:

$$D(\text{preserve}^{1,2}) = 1 - \frac{\sum_i \sum_{j \neq i} |a_{ij}^1 - a_{ij}^2|}{n(n-1)} \quad (3)$$

Where D is the preservation density, $a_{ij}^1$ and $a_{ij}^2$ are adjacencies for each phenotype, and n is the total number of genes. The closer the preservation density is to 1, the stronger the evidence that the connectivity pattern is preserved between the two networks.

A measure of module membership $kME_i = \text{cor}(x_i, ME)$ can be defined as the correlation between expression profile of gene i and the module eigengene. The closer the absolute value of $kME_i$ is to 1, the stronger the evidence that the gene belongs to the module represented by the module eigengene (Horvath S, Dong J. Geometric interpretation of gene coexpression network analysis. PLoS Comput Biol. 2008; 4:e1000117). Therefore, marker genes not assigned to fetal modules (MYH6, PLN) were re-assigned to the module with highest kME. Module membership of other marker genes (NPPA, MYH7, SLC2A4) was simply the module assignment of each respective gene as given by the algorithm described previously.

Supplementary Methods

Data Combination and Normalization

Prior to data analysis, all 1617 arrays had to be appropriately combined such that probeset identifiers matched to homologous genes. Probeset annotation files for each array platform were used to identify the gene symbol associated with each probeset and this gene symbol was mapped to a unique identifier for homologous gene groups provided by the homologene database. Data were then combined from all experiments by matching homologene identifiers. To allow for comparison of absolute gene expression data between phenotypes across different experimental data sets, normalization of raw expression data was performed prior to all analyses. Median absolute deviation normalization of log transformed expression values was chosen for its performance advantages in sparse datasets (Barbacioru C C, Wang Y, Canales R D, Sun Y A, Keys D N, Chan F, Poulter K A, Samaha R R. Effect of various normalization methods on Applied Biosystems expression array system data. BMC Bioinformatics. 2006; 7:533). Via this method, intensity-dependent differences in expression level were minimized for between-sample comparisons, as evidenced by M-A plot (See FIG. 7). Of note, the Pearson correlation is invariant under data transformation of location and scale and thus this normalization step does not affect gene expression network analysis.

Shown in FIGS. 7A and B are charts demonstrating the normalization of gene expression data using mean absolute deviation method reduces intensity-dependent differences for experiments from different experimental conditions according to an embodiment of the present invention. FIGS. 7A.1 and 7A.2 depict the relationship between mean and difference between experimental arrays for all experiments with the same experimental set (e.g., FIG. 7A.1 with similar laboratory conditions) and for experiments not within the same experimental set (e.g., FIG. 7A.2 with different laboratory conditions) before performing normalization. Horizontal scatter envelopes centered at 0 indicate minimal intensity-dependent differences in expression level. Shown in FIGS. 7B.1 and 7B.2 are the same relationships after performing normalization. FIGS. 7B.1 and 7B.2 indicate minimization of intensity-dependent differences in expression among disparate experimental conditions.

Species Specificity

Species specificity of gene coexpression was analyzed to assess for primacy of species over phenotype. Experiments were clustered according to shared expression profiles using agglomerative hierarchical clustering. As shown in FIG. 8, array experiments were tightly coordinated by species, indicating a significant species dependency for gene coexpression. As such, datasets from species with the most complete data set with regard to phenotype, mouse, were chosen for further analysis.

Shown in FIGS. 8A-8D are charts that assist in understanding gene expression profiles from different experimental conditions clustered by species according to an embodiment of the present invention. Hierarchical clustering of experimental conditions was performed to evaluate for species-specific patterns of gene coexpression. The top half of each figure depicts the hierarchical clustering of experiments within each experimental phenotype and the bottom half contains a color-keyed representation of species identifiers for each experiment. In normal adult (FIG. 8A), fetal (FIG. 8B), failing (FIG. 8C), and hypertrophied (FIG. 8D) cardiac tissue experiments clustered tightly by species, indicating strong species dependency of gene coexpression. Abbreviations are: H=human, M=mouse, R=rat, D=dog.

Forming Networks

To perform network modeling, weighted gene coexpression analysis was used as described in Zhang et al (Zhang B, Horvath S. A general framework for weighted gene co-expression network analysis. Stat Appl Genet Mol Biol. 2005; 4:Article17). The vertices of a weighted gene co-expression graph represent genes and the connection strengths (adjacency) between them comprise edges that connect vertices. The connectivity $k_i$ of the i-th vertex (gene) is defined as the sum of its adjacencies with the other nodes in the network. The frequency distribution of the connectivity often (but not always) follows a power law, which is referred to as scale free topology. Many (but not all) biologic networks have been found to satisfy scale free topology (Barabasi A L, Albert R. Emergence of scaling in random networks. Science. 1999; 286:509-512; Jeong H, Tombor B, Albert R, Oltvai Z N, Barabasi A L. The large-scale organization of metabolic networks. Nature. 2000; 407:651-654). The connection strength or adjacency was determined by the Pearson correlation of the corresponding expression profiles.

Specifically, the connection strength (adjacency)

$$A_{ij}=|cor(x_i,x_j)|^b$$

between expression profiles i and j is a power of the absolute value of their Pearson correlation. Forming the power of a correlation amounts to a soft-thresholding approach that emphasizes large correlations at the expense of low correlations and obviates the need for arbitrary thresholds for adjacency, thus preserving the continuous nature of the co-expression information. The extent to which a network satisfies scale free topology can be measured using a model fitting index $R^2$. FIGS. 9 and 10 show how the scale free topology model fitting index $R^2$ (y-axis) depends on the soft threshold b (x-axis).

Shown in FIGS. 9A and 9B are gene coexpression network adjacency soft thresholds for different conditions according to an embodiment of the present invention. FIG. 9. Shown in FIG. 9A is a gene coexpression network adjacency soft threshold for normal adult was chosen to approximate scale-free topology. Shown in FIG. 9A is a gene coexpression network adjacency soft threshold for fetal cardiac tissue was chosen to approximate scale-free topology. FIGS. 9A.1 and 9B.1 depict the relationship between soft-thresholding coefficient (x axis, numbered in red) and the r value for the linear regression (y axis, slope constrained to −1) between the logarithm of the connectivity and the logarithm of the proportion of genes with that connectivity. FIGS. 9B.1 and 9B.2 depict the relationship between the soft-thresholding coefficient and mean connectivity.

Shown in FIG. 10 are gene coexpression network adjacency soft threshold for different conditions according to an embodiment of the present invention. Failing (FIGS. 10A.1 and 10A.2) and hypertrophied cardiac tissue (FIGS. 10B.1 and 10B.2) were chosen to approximate scale-free topology. FIGS. 10A.1 and 10B.1 depict the relationship between soft-thresholding coefficient (x axis, numbered in red) and the r value for the linear regression (y axis, slope constrained to −1) between the logarithm of the connectivity and the logarithm of the proportion of genes with that connectivity. FIGS. 10B.1 and 10B.2 depict the relationship between the soft-thresholding coefficient and mean connectivity.

The factor b was chosen according to the scale free topology criterion, which amounts to choosing the smallest b that leads to approximate scale free topology. To facilitate comparisons, b=9 was chosen for all networks. A major advantage of weighted co-expression networks is that they are statistically highly robust with regard to the chosen threshold b. The final adjacency was further defined using the topological overlap (Yip A M, Horvath S. Gene network interconnectedness and the generalized topological overlap measure. BMC Bioinformatics. 2007; 8:22). This network adjacency describes the commonality of network neighbors for genes i and j and is given by:

$$t_{ij} = \begin{cases} \dfrac{l_{ij} + a_{ij}}{\min\{k_i, k_j\} + 1 - a_{ij}} & \text{if } i \neq j \\ 1 & \text{if } i = j \end{cases} \quad (1)$$

where $$l_{ij} = \sum_{u \neq i,j} a_{iu} a_{uj}, \; k_i = \sum_{u \neq i} a_{iu}, \text{ and } k_j = \sum_{u \neq j} a_{uj}$$

for $a_{iu}$ and $a_{uj}$ given by soft-thresholded Pearson correlation as described above. For all $t_{ij}$ a distance $d_{ij}=1-t_{ij}$ was defined, giving a symmetrical distance matrix of 12620 rows and 12620 columns. This distance matrix was used as the input for agglomerative hierarchical clustering in the training set of 43 fetal samples and subsequently in a validation set of 21 fetal samples and in other phenotypes. Separate distance matrices were constructed for each phenotype and for training and validation fetal datasets. The dynamic tree cut algorithm was used to define gene modules from the resultant hierarchical clustering. For this algorithm, minimum cluster size was set at 25, the "hybrid" tree cut algorithm was chosen, deep split was set to one, and no minimum or maximum absolute core scatter were defined; sensitivity analysis for the parameters chosen for this function is described in FIG. 11.

Shown in FIG. 11 is a sensitivity analysis for parameters used in the dynamic tree cut algorithm according to an embodiment of the present invention. The z-axis describes module reproducibility average over all derived modules, which is in turn given by the Pearson correlation between vectors describing intra-modular connectivity for each gene. In an embodiment, the chosen parameters for the dynamic tree cut algorithm (deepsplit=1, labelunlabeled=TRUE) gave the highest average reproducibility of modules in the fetal dataset.

The 90 resulting networks were subsequently internally validated using an iterative approach as described above in the validation set (see FIG. 12). The degree to which topology of these validated modules was shared between phenotypes was then evaluated using the same iterative approach. To illustrate topology of key marker genes previously identified to be associated with cardiac development and disease, gene coepxression topology of networks containing these genes is displayed in FIG. 13.

Shown in FIGS. 12A-12C are charts and graphs demonstrating the identification and validation of fetal gene modules according to an embodiment of the present invention. In an embodiment, genes were clustered first by topological overlap in the training dataset (n=43 samples) and then evaluated for significant reproducibility in the validation dataset (n=21 samples). Shown in FIG. 12A is a cluster dendrogram and barplot describing module membership for each of the 12,620 genes. Shown in FIG. 12B is a cluster dendrogram and barplot describing module membership for each of the 12,620 genes (as defined in the training set) in the validation dataset. Shown in FIG. 12C is a significance (−log p value) of module reproducibility in the validation set. The cutoff for statistical significance (p<5.5×10-4 or −log(p value)>3.26) is shown. Seventy-two modules met this criterion.

Shown in FIGS. 13A and 13B is a topology of developmental gene coexpression modules containing key marker genes. The hub genes for modules containing NPPA and MYH7 (FIG. 13A) and SLC2A4 (FIG. 13B) are depicted by an "X", while marker genes are depicted by a "+." Only edges with adjacency weight>0.7 are shown for clarity. The proximity of each gene to the center of the figure indicates its connectivity, or sum of connection weights.

Transcription Factor Target Identification

Transcription factor target identification was performed to assess for common transcription factor modulation of gene coexpression modules. The phylogenetic footprinting approach was applied to determine putative gene targets for a large set of vertebrate transcription factors in the mouse genome (Levy S, Hannenhalli S. Identification of transcription factor binding sites in the human genome sequence. Mamm Genome. 2002; 13:510-514). All eukaryotic transcription factor motifs were first clustered from TRANSFAC v10.2 into 235 representative motifs as described (Wingender E, Dietze P, Karas H, Knuppel R. TRANSFAC: a database on transcription factors and their DNA binding sites. Nucleic Acids Res. 1996; 24:238-241; Hannenhalli S, Putt M E, Gilmore J M, Wang J, Parmacek M S, Epstein J A, Morrisey E E, Margulies K B, Cappola T P. Transcriptional genomics associates FOX transcription factors with human heart failure. Circulation. 2006; 114:1269-1276). For each of the 235 motifs provided in the TRANSFAC database, the mouse 1 kb promoter regions were scanned to first identify match with a p-value≤0.0002. These matches were further filtered to only include the binding sites that are either 80% conserved between human and mouse genomes based on the genome alignment provided in UCSC database or the match p-value≤0.00002. In a cross validation with experimentally verified binding sites, these criteria yielded a false positive rate of 1 in 50 kB of genomic data searched, or a false discovery rate of 1 transcription factor for every 50 genes searched in the algorithm according to an embodiment of the present invention.

Results

Network Topology can be Defined for Large Datasets of Myocardial Gene Expression Data Fetal gene programs were first defined as modules of gene co-expression specific to fetal myocardial tissue. To this end, weighted gene co-expression networks were constructed for fetal myocardial tissue using every murine transcript abundance dataset available in the Gene Expression Omnibus (GEO) database. A data search strategy and summary of experimental conditions according to an embodiment of the present invention is presented in FIG. 1. Modules were internally validated using a data-splitting technique in which 43 (67%) samples were used as a training set and 21 (33%) samples were used to validate the derived modules. In the training set, hierarchical clustering of the topological overlap matrix identified 90 modules composed of between 25 and 1309 genes. A summary of analyzed genes and modules is presented further below. The preservation of all gene-gene connections between training and validation datasets as defined by the preservation density was 94%. Of the 90 original modules, 72 had network topology that was significantly preserved in the validation set (p<5.5×10$^{-4}$ for reproducibility) and were carried forward for all subsequent analysis.

Gene Expression in the Developing Heart Involves Modules not Conserved in Normal Adults Because there are modules of gene expression that represent constitutive genetic programs of cardiac tissue, the subset of these validated modules was next identified that were not reproduced in normal adult myocardium (n=273 samples). Of the 72 valid modules identified in fetal myocardium, 26 were also found in normal myocardium (p<6.9×10-4 for reproducibility between fetal and normal datasets, FIG. 2). Four of these 26 modules were reproduced in adult myocardium but also exhibited significant differential expression (p value for averagedifferential expression<0.002) as a module. Thus, 50 modules of between 25 and 914 genes were found to comprise the gene expression program of the developing heart.

Figure 2:
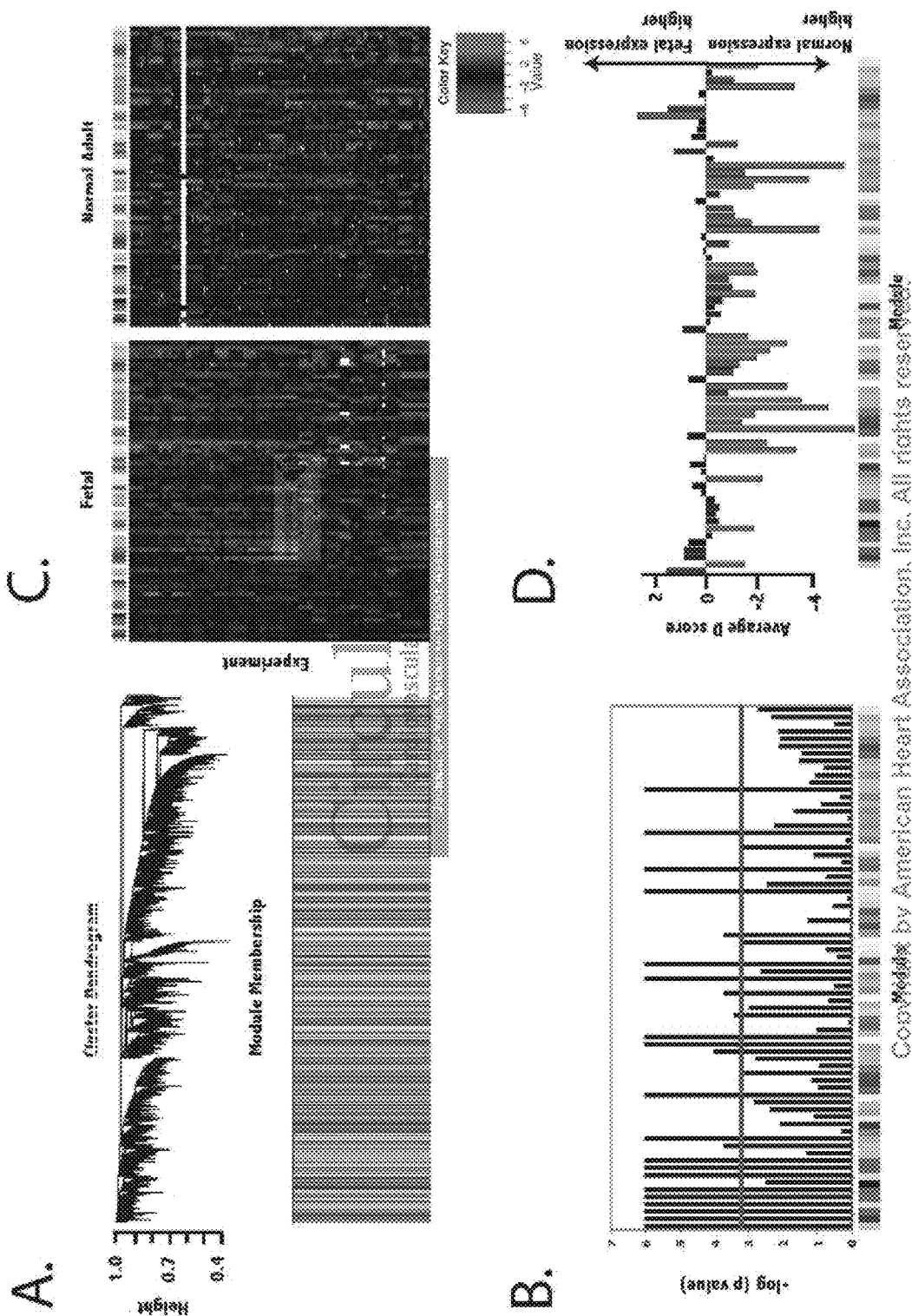
FIGS. 2A-2D are charts and graphs that assist the identification of gene coexpression modules specific to fetal tissue according to an embodiment of the present invention.

Shown in FIG. 2 is the identification of gene coexpression modules specific to fetal tissue. Gene-gene adjacencies were first defined by the topological overlap, which quantifies the degree of shared network neighbors given by gene-wise Pearson correlation. Hierarchical clustering of adjacencies was first performed in the training dataset of 43 fetal samples and resulting coexpression modules were evaluated for significant reproducibility in the validation dataset of 21 fetal samples. The seventy-two valid fetal modules were evaluated for reproducibility in normal adult myocardium as well as differential expression. Shown in FIG. 2A is a cluster dendrogram and barplot describing module membership (according to clusters derived in the training fetal dataset) for normal adult myocardium. Shown in FIG. 2B is a representation of the reproducibility of valid fetal modules in normal adult myocardium. The horizontal line indicates cutoff for statistical significance (p<6.9×10−4 or −log(p value)>3.16). Modules below this cutoff were defined as having topology specific to fetal myocardium and defined as fetal modules. Shown in FIG. 2C is a heatmap of average expression of each module in fetal and normal adult myocardium. Shown in FIG. 2D is the average significance level of differential expression (average Significance Analysis of Microarrays d score) for each module according to an embodiment of the present invention. Negative values correspond to lower expression levels in normal than fetal myocardium.

Known Marker Genes for Heart Failure are Members but not Hubs of Conserved Modules The composition of these conserved modules was next examined using annotated gene ontologies. Topology of gene modules containing key marker genes is described in FIG. 13. Matching expected results, MYH7 and NPPA were members of a module up-regulated in fetal tissue compared to normal tissue (156 members, average d score 4.66). SLC2A4 was a member of a module down-regulated in fetal compared to normal tissue (64 members, average d score −4.95). Though not contained in modules specific to fetal cardiac tissue, MYH6 and PLN expression most closely aligned with members of a module down-regulated in fetal compared to normal tissue (90 members, average d score −1.6).

Limited Recapitulation of Fetal Modules in Failing Myocardium

The hypothesis that fetal gene modules are re-capitulated in failing (n=41 samples) and pathologically hypertrophied myocardial tissue (n=100 samples) was evaluated. These data are summarized in FIG. 3 and in Tables 1 and 2 (FIGS. 14 and 15, respectively). FIG. 14 (Table 1) is tabular data regarding over-represented biological processes according to gene ontology (GO) in the fetal module recapitulated in heart failure and hypertrophy according to an embodiment of the present invention. FIG. 15 (Table 2) is tabular data summarizing genes involved in protein catabolism biological process from fetal module recapitulated in heart failure and hypertrophy.

Figure 3A:
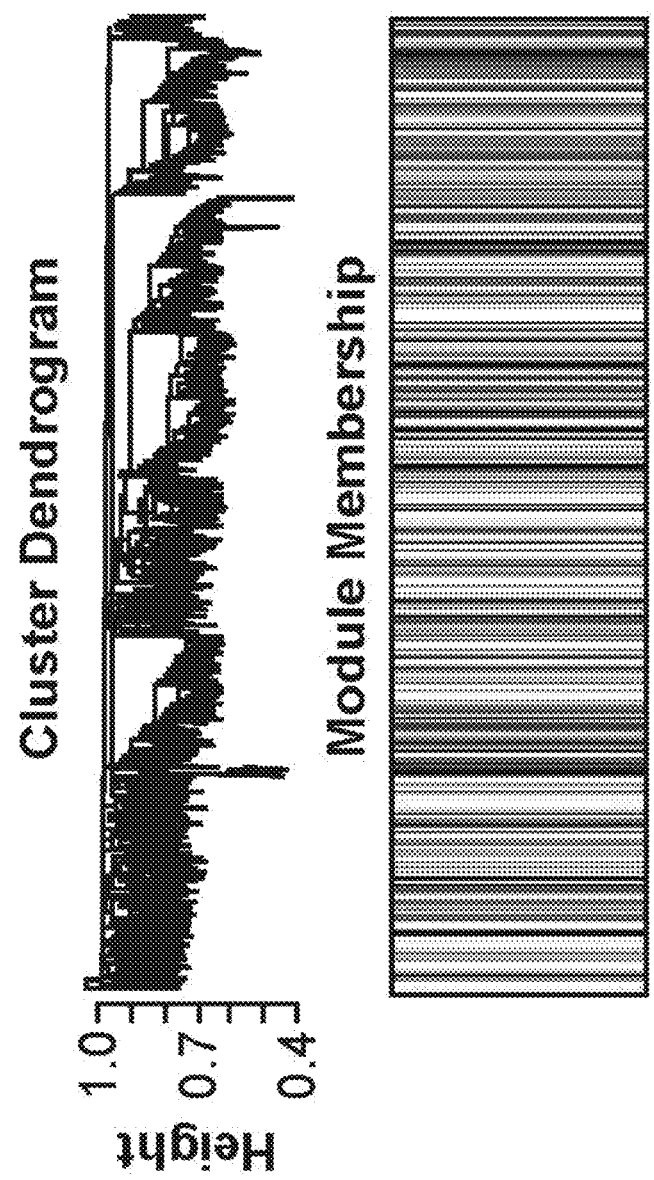
Figure 3B:
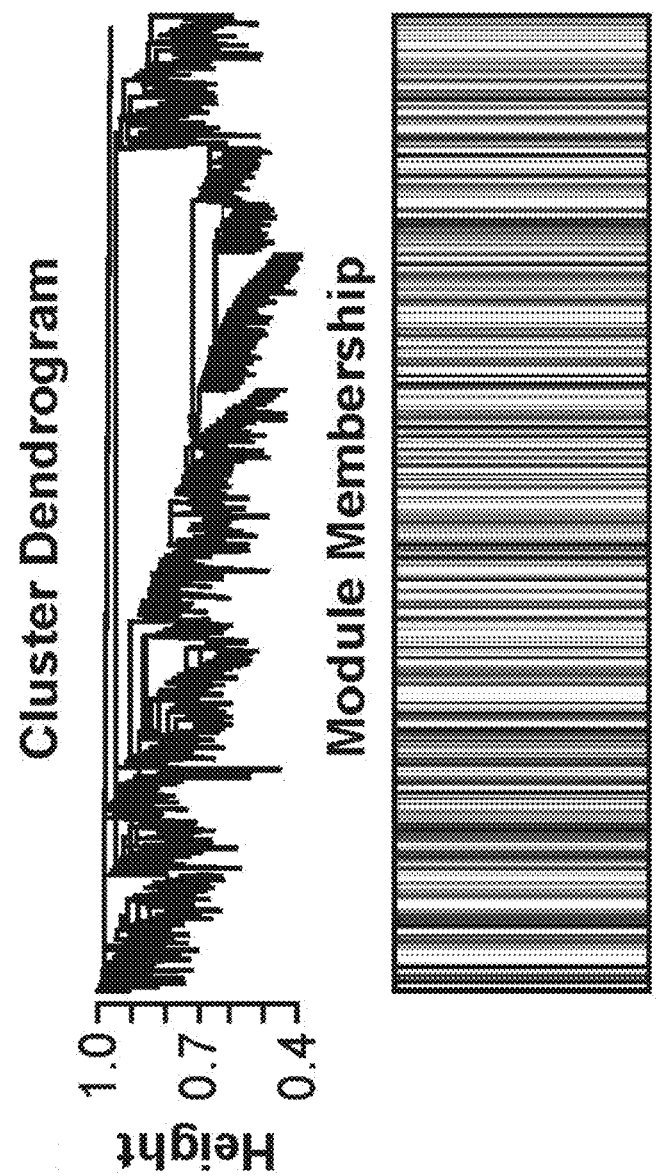
Figure 3C:
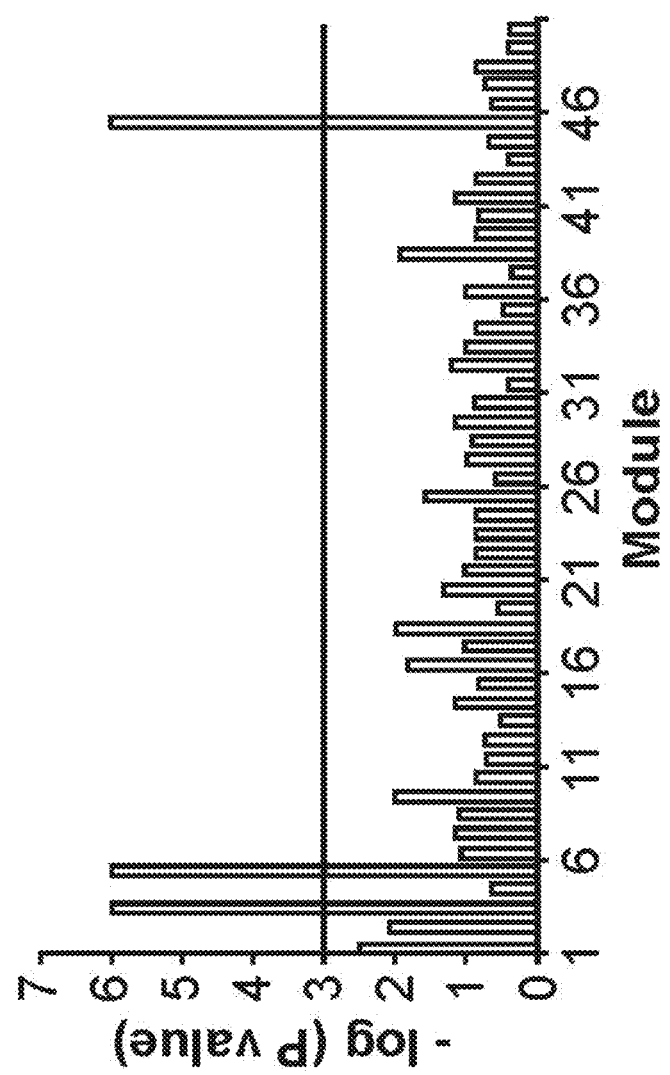
Figure 3D:
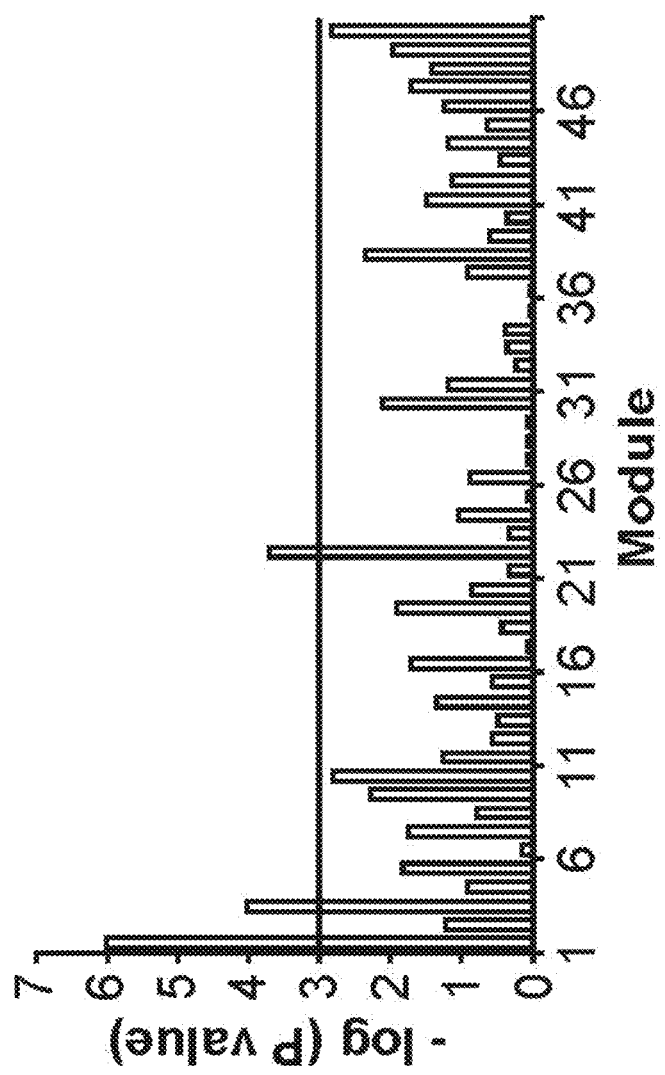
Figure 3E:
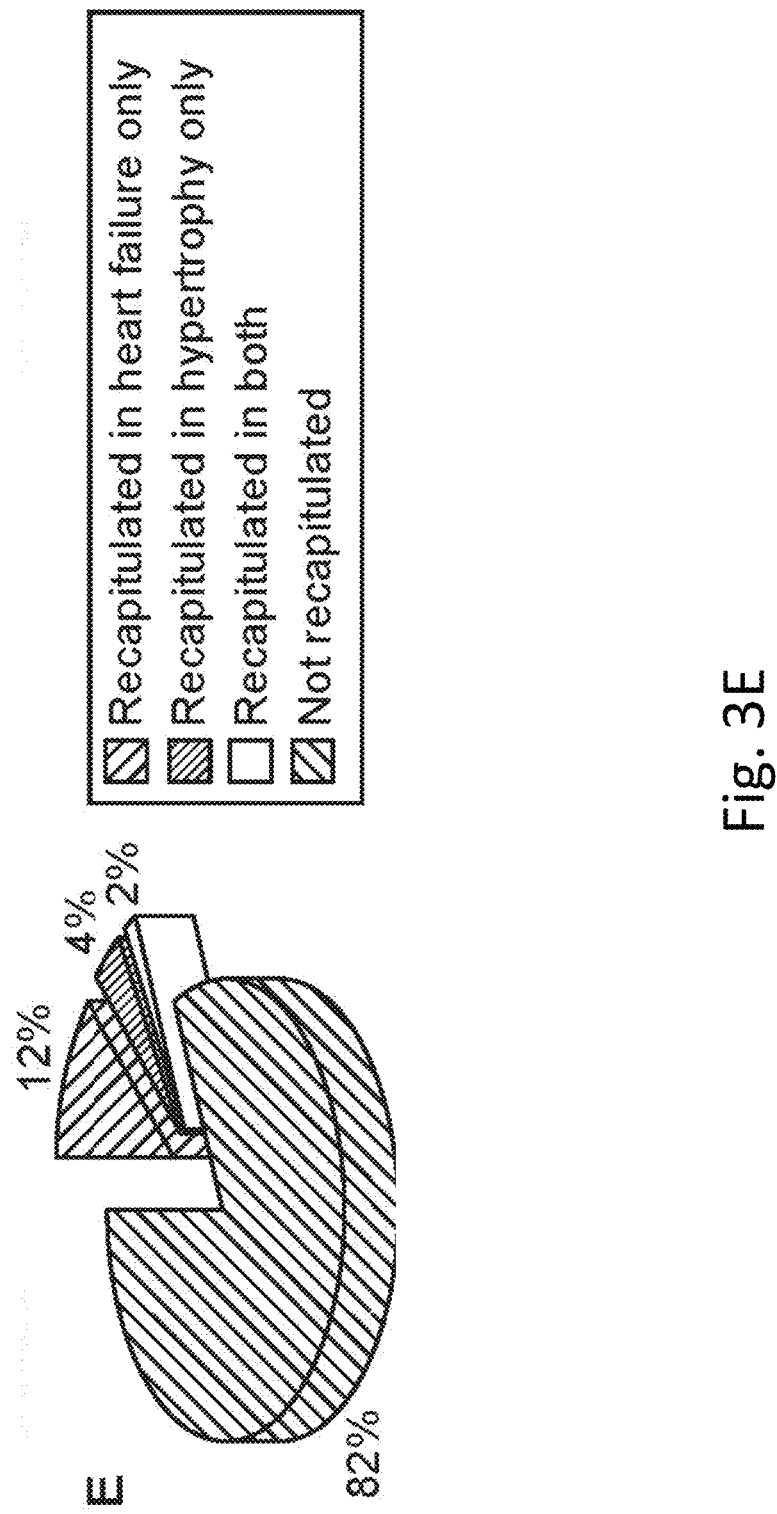

Shown in FIGS. 3A-E are charts and graphs demonstrating the reproducibility of developmental gene modules in heart failure and cardiac hypertrophy according to an embodiment of the present invention. The modules unique to fetal myocardium were evaluated for reproducibility in heart failure and cardiac hypertrophy. Cluster dendrograms and barplots describe module membership (according to clusters derived in the training fetal dataset). Shown in FIG. 3A is myocardium in murine heart failure. Shown in FIG. 3B is myocardium in murine cardiac hypertrophy. Bargraphs describe significance of module reproducibility in FIGS. 3C (heart failure) and 3D (cardiac hypertrophy). A horizontal line indicates cutoff for statistical significance ($p<0.001$ or $-\log(p\ value)>3$). E.) Proportion of fetal gene modules recapitulated in heart failure only, cardiac hypertrophy only, both, or neither.

Seven (14%) of 50 fetal gene modules were reproduced in failing myocardium with $p<0.001$. Three (6%) of 50 fetal gene modules were significantly reproduced in pathological hypertrophy. One module (FIG. 4) composed of 246 genes was reproduced in both failing and hypertrophied myocardium. The hub gene for this module, dihydroepiandrosterone sulfotransferase (SULT2A1) encodes an enzyme with high levels of expression in heart, adrenal glands, and liver and catalyzes the conjugation of steroids and bile acids (Nakamura Y, Xing Y, Sasano H, Rainey W E. The mediator complex subunit 1 enhances transcription of genes needed for adrenal androgen production. Endocrinology. 2009; 150: 4145-4153; Nowell S, Falany C N. Pharmacogenetics of human cytosolic sulfotransferases. Oncogene. 2006; 25:1673-1678).

Shown in FIG. 4 is the topology of gene coexpression module common to developing myocardium and hypertrophied and failing myocardium according to an embodiment of the present invention. Edges with adjacency weight>0.7 are shown for clarity. The proximity of each gene to the center of the figure indicates its connectivity, or sum of connection weights. Genes with connectivity<50 are omitted for clarity.

Transcription Factors are Significantly Over-represented in Discovered Modules

Over-representation of transcription factor targets in each module were then analyzed. Targets of the transcription factor zinc finger protein 2 (ZIC2, product of gene ZIC2) were significantly over-represented in the fetal module common to both failing and hypertrophied myocardium ($p=3\times10^{-4}$) after correcting for multiple comparisons. Fetal modules reproduced in heart failure were enriched in targets of transcription factor HOXA5 ($p=3\times10^{-5}$) and fetal modules reproduced in hypertrophy were enriched in targets of the transcription factor FOXN1 ($p=4\times10^{-4}$).

Ontology Analysis Reveals Key Role of Metabolic Processes in Fetal and Failing Myocardium Common biological process pathways were found among fetal and failing myocardium. In the fetal module reproduced in heart failure and cardiac hypertrophy, proteasomal protein catabolic processes ($p=5.9\times10^{-5}$, corrected $p=0.085$) and protein catabolic processes ($p=4.2\times10^{-4}$, corrected $p=0.085$) were overrepresented. Other biological processes overrepresented in gene modules common to developing and failing myocardium (n=7) were cytoskeleton organization and biogenesis (corrected $p=8.5\times10^{-3}$) and fatty acid oxidation (corrected $p=9.2\times10^{-3}$). Fetal modules recapitulated in hypertrophy (n=3) were enriched in genes involved in membrane lipid metabolic processes (corrected $p=0.02$). Other fetal modules with significant enrichment for biological processes were involved in stress response, nervous system development, biopolymer metabolism, and innate and humoral immunity (corrected $p<0.05$).

Higher Order Topological Overlap is Poorly Preserved Between Fetal and Failing Myocardium Eigengene networks reveal connectivity patterns between modules, e.g., they allow one to study higher order topology of the transcriptome and relationships between biological pathways represented in each gene module. Derived eigengenes explained between 32% and 67% of the variance in gene expression for each module. Preservation of higher order topology of the module network is presented in FIG. 5 in both graphical form and as cluster dendrograms. The preservation of fetal inter-modular connections in failing and hypertrophied myocardial tissue was low (52% and 58%, respectively).

Shown in FIG. 5 are representations of the reproducibility of higher-order network topology between fetal myocardium and myocardium in murine heart failure and cardiac hypertrophy according to an embodiment of the present invention. Singular value decomposition was used to generate a representative eigengene for each fetal module that described most of the variance in modular gene expression. Hierarchical clustering of eigengenes was then used to identify inter-modular connections. Heatmaps describe the correlation between eigengenes and the dendrograms represent clustering of module eigengenes in FIGS. 5A (fetal myocardium), 5B (myocardium in murine heart failure), and 5C (myocardium in cardiac hypertrophy). The line of identity has correlation=1 for all modules. Graphical representation of eigengene networks is represented for fetal myocardium in FIG. 5D, heart failure in FIG. 5E, and cardiac hypertrophy in FIG. 5F. Values given for preservation refer to preservation of fetal inter-modular connections in heart failure and cardiac hypertrophy.

Discussion

In this study, network analysis tools were applied to the largest dataset of myocardial transcriptomic data assembled to date. Modular sets of genes with a high degree of coexpression in developing myocardial tissue were identified an evaluated. Their conservation was tested across different pathological states. Specially, the question of whether a coordinated fetal gene expression program is recapitulated in heart failure and hypertrophy was addressed.

In traditional differential gene expression analysis, investigators have applied statistical tools that were developed for evaluation of associations between a small number of predictors (e.g., clinical characteristics or medical interventions) and a large number of outcomes (e.g., mortality).

However, these analytical approaches are often inadequate to describe the associations between the large number of gene expression signatures and relatively small number of phenotype experiments in genome-wide expression studies. Identification of a relatively small number of modules and subsequent module-wise, rather than gene-wise, analysis yields a lower false discovery rate than would be expected with more traditional analyses. Modular gene expression analysis also facilitated evaluation of higher-order topology of the transcriptome and associated transcriptional regulators in heart failure and developing myocardium.

Using these analytical tools, a significant proportion of modular gene programs were found to be either unique to fetal cardiac tissue or to be present but differentially expressed in normal adult myocardium. Analysis of the composition of these fetal gene modules corroborated prior evidence of differences in myocardial energetic pathways and sarcomeric composition between fetal and normal adult myocardium 2-5. Furthermore, fetal modules were identified that were involved in membrane lipid metabolism, nervous system development, and innate and humoral immunity whose importance to developing myocardium, if confirmed in experimental model systems, enriches the understanding of myocardial development.

It was found that key fetal pathways of myocardial energetics previously demonstrated to be recapitulated in myocardial adaptation (Hansson A, Hance N, Dufour E, Rantanen A, Hultenby K, Clayton D A, Wibom R, Larsson N G. A switch in metabolism precedes increased mitochondrial biogenesis in respiratory chain-deficient mouse hearts. Proc Natl Acad Sci USA. 2004; 101:3136-3141) were represented in gene modules that were preserved between fetal and failing and hypertrophied myocardium. Novel pathways that were shared between developing and failing/hypertrophied myocardium were also identified in the analysis of the present invention and may represent key stress response pathways important to both the fetal circulation and myocardial adaptation. It is yet unclear which of these pathways may represent maladaptive cardiovascular stress responses.

This set of recapitulated modules represented a small proportion of the identified fetal gene program and there was little overlap between fetal modules recapitulated in heart failure and those recapitulated in cardiac hypertrophy. These findings have important implications for the understanding of myocardial adaptation to injury. The hypothesis that a coordinated program of developmental gene expression is recapitulated in myocardial adaptation is accepted (Vanderheyden M, Mullens W, Delrue L, Goethals M, de Bruyne B, Wijns W, Geelen P, Verstreken S, Wellens F, Bartunek J. Myocardial gene expression in heart failure patients treated with cardiac resynchronization therapy responders versus nonresponders. J Am Coll Cardiol. 2008; 51:129-136). Results according to an embodiment of the present invention suggest that this model of myocardial adaptation may be inadequate to describe the genomic response to myocardial stress. Instead, the spectrum of myocardial adaptation in which compensatory hypertrophy progresses to myocardial failure appears to involve diverse and plastic pathways of genomic response which are not easily distilled to one coordinated program of fetal gene expression. Furthermore, it was found that the higher order organization of genomic response, represented by connections between modules of shared gene expression, was disparate between developing, failing and hypertrophied myocardium.

Several regulators of expression, including transcriptional activators and repressors, histone deacetylases, and microRNAs, have been shown to modulate transcription and translation of portions of the gene expression program of the developing heart and heart failure and hypertrophy (Thattaliyath B D, Livi C B, Steinhelper M E, Toney G M, Firulli A B. HAND1 and HAND2 are expressed in the adult-rodent heart and are modulated during cardiac hypertrophy. Biochem Biophys Res Commun. 2002; 297:870-875; Kuwahara K, Saito Y, Takano M, Arai Y, Yasuno S, Nakagawa Y, Takahashi N, Adachi Y, Takemura G, Horie M, Miyamoto Y, Morisaki T, Kuratomi S, Noma A, Fujiwara H, Yoshimasa Y, Kinoshita H, Kawakami R, Kishimoto I, Nakanishi M, Usami S, Saito Y, Harada M, Nakao K. NRSF regulates the fetal cardiac gene program and maintains normal cardiac structure and function. Embo J. 2003; 22:6310-6321; Trivedi C M, Luo Y, Yin Z, Zhang M, Zhu W, Wang T, Floss T, Goettlicher M, Noppinger P R, Wurst W, Ferrari V A, Abrams C S, Gruber P J, Epstein J A. Hdac2 regulates the cardiac hypertrophic response by modulating Gsk3 beta activity. Nat Med. 2007; 13:324-331; Thum T, Galuppo P, Wolf C, Fiedler J, Kneitz S, van Laake L W, Doevendans P A, Mummery C L, Borlak J, Haverich A, Gross C, Engelhardt S, Ertl G, Bauersachs J. MicroRNAs in the human heart: a clue to fetal gene reprogramming in heart failure. Circulation. 2007; 116:258-267; van Rooij E, Sutherland L B, Liu N, Williams A H, McAnally J, Gerard R D, Richardson J A, Olson E N. A signature pattern of stress-responsive microRNAs that can evoke cardiac hypertrophy and heart failure. Proc Natl Acad Sci USA. 2006; 103: 18255-18260). Here, a novel association of the transcription factor ZIC-2 with gene coexpression modules common to myocardial development and adult myocardial adapation was identified. Loss of function mutations in this transcription factor are associated with a defect of forebrain development, holoprosencephaly, complex skeletal defects and congenital heart disease (Grinberg I, Millen K J. The ZIC gene family in development and disease. Clin Genet. 2005; 67:290-296). Modules common to developing and failing myocardium were enriched in targets of HOXA5, a transcription factor with known roles in lung development in mammals and apoptotic heart morphogenesis in amphibians (Kim C, Nielsen H C. Hoxa-5 in mouse developing lung: cell-specific expression and retinoic acid regulation. Am J Physiol Lung Cell Mol Physiol. 2000; 279:L863-871; Grier D G, Thompson A, Lappin T R, Halliday H L. Quantification of Hox and surfactant protein-B transcription during murine lung development. Neonatology. 2009; 96:50-60; Gaur A, Bhatia R, Spring-Mills E, Lemanski L F, Dube D K. The heart of metamorphosing Mexican axolotl but not that of the cardiac mutant is associated with the upregulation of Hox A5. Biochem Biophys Res Commun. 1998; 245:746-751). Targets of the transcription factor FOXN1, which is known to be involved in thymic development and lymphocyte regulation, were found in modules shared between developing and hypertrophied myocardium (Coffer P J, Burgering B M. Forkhead-box transcription factors and their role in the immune system. Nat Rev Immunol. 2004; 4:889-899). This transcription factor is involved in cardiomyocte-rich embryoid body development in pharyngeal endoderm and other members of the forkhead box transcription factor family have been implicated in human and murine heart failure (Hidaka K, Nitta T, Sugawa R, Schwartz R J, Amagai T, Nitta S, Takahama Y, Morisaki T. Differentiation of Pharyngeal Endoderm and Derivatives from Mouse Embryonic Stem Cells. Stem Cells Dev. 2010; 19:1735-1743; Hannenhalli S, Putt M E, Gilmore J M, Wang J, Parmacek M S, Epstein J A, Morrisey E E, Margulies K B, Cappola T P. Transcriptional genomics associates FOX transcription factors with human heart failure. Circulation. 2006; 114: 1269-1276).

In an embodiment of the present invention, evidence is shown of the role of these transcription factors in modulation of the gene programs common to developing myocardium and myocardial adaptation. With experimental confirmation of the role of these transcription factors inmodulation of gene expression programs of the developing heart and identification of additional common transcription factor and microRNA targets, it may be possible to identify regulators of fetal gene networks that allow for manipulation of maladaptive portions of the program.

Myocardial expression data was evaluated from disparate sources which utilized different experimental model systems and different tissue preparation, transcript isolation, and microarray techniques. This can be considered a strength of the present invention. It is unlikely that a single model from one laboratory adequately captures the diversity of disease. By concentrating on the findings common to many different models and techniques from many different laboratories, focus can be placed on the most robust changes common to all. Further, normalization minimized between-array differences, while a module identification technique robust to noise was used with an iterative approach to validate modules.

Due to the data from human samples, an embodiment of the present invention concentrated on murine experimental models.

CONCLUSION

In an embodiment of the present invention, a gene expression topology of the developing and diseased heart is described. Key transcriptional regulators of the fetal gene expression program are identified. Novel module conservation algorithms are applied to address the question of the recapitulation of fetal gene markers and gene networks in heart failure and hypertrophy. While marker genes are clearly upregulated in gene networks common to developing and diseased myocardium, they are not found to be the most highly connected genes. In addition, evidence was found for a coordinated recapitulation of gene expression programs found in the developing heart that is recapitulated in myocardial adaptation.

There are over 1600 single-gene ("Mendelian") inherited disorders for which the molecular basis is unknown. An additional 1800 suspected Mendelian traits have unknown genetic basis. Current approaches to identifying the genetic basis of disease (positional cloning, linkage analysis) are costly and time consuming and have limited sensitivity for defining genetic syndromes. The advent of whole genome sequencing has allowed increased sensitivity for polymorphisms associated with disease, but there is a need for better prioritization of putative gene targets in families with inherited disease syndromes. The method described here leverages the wealth of information from gene expression, protein interaction, and genetic variation to prioritize genes for co-segregation analysis.

Hierarchical link clustering is computationally intensive. The present invention can be implemented with hierarchical clustering of genes based on topological overlap, a similarity measure that captures the degree of shared network neighbors. Based on results of "leave-one-out" cross-validation, the threshold can be modified for step length (degree of separation between network neighbors) in identification of genes related to known disease genes. In another embodiment, clustering phenotypes can be considered based on shared genetic and clinical features to enlarge the starting scaffold set of disease genes.

It should be appreciated by those skilled in the art that the specific embodiments disclosed above may be readily utilized as a basis for modifying or designing other algorithms or systems. It should also be appreciated by those skilled in the art that such modifications do not depart from the scope of the invention as set forth in the appended claims.

What is claimed is:

1. A computer implemented method for generating a gene specific diagnostic platform comprising:
    obtaining a first set of genetic data using a computing device, wherein the first set of genetic data identifies genes and gene expression associated with the genes;
    generating a co-expression network of the set of gene expression data using the computing device, wherein the co-expression network identifies a set of modules of genes with similar patterns of gene expression;
    obtaining a set of known disease associated genes using the computing device;
    identifying at least one module from the set of modules associated with at least one known disease associated gene from the set of known disease associated genes using the computing device;
    obtaining a set of genetic variants, wherein the set of genetic variants identifies known genetic variants associated with genes using the computing device;
    identifying at least one gene from the set of genetic variants associated with the at least one module associated with at least one known disease associated gene using the computing device; and
    creating a gene specific diagnostic platform based on the at least on gene within the at least one module associated with the at least one known disease associated gene, wherein the gene specific diagnostic platform is used for molecular diagnosis of an individual for inherited disease syndromes.

2. The method of claim 1,
wherein the generating a co-expression network step comprises the steps of:
    querying the first set of genetic data using a set of terms of interest to retrieve a subset of the first set of genetic data associated with the terms of interest using the computing device;
    performing data combination and normalization on the subset of the first set of genetic data using the computing device to produce a set of normalized genetic data;
    generating a first gene co-expression network using the set of normalized genetic data using the computing device, wherein:
        the gene co-expression network comprises a plurality of vertices and a plurality of edges;
        each of the plurality of edges represents a link between two of the plurality of vertices;
        the plurality of vertices contain data representing genes; and
        the plurality of edges comprise a length value representing the degree of connection strength between two vertices that the edge links;
    identifying a set of gene co-expression modules within the first gene co-expression network based upon agglomerative hierarchical clustering using the computing device, wherein each gene co-expression module of the set of gene co-expression modules comprises a subset of the plurality of vertices containing data predicted to describe a plurality of trait-associated genes.

3. The method of claim 2, wherein identifying the set of gene co-expression modules comprises:
identifying at least one hierarchical cluster of edges of the first gene co-expression network graph data structure using the computing device; and
identifying at least one modular sub-network from the at least one hierarchical cluster using the computing device, wherein the plurality of trait-associated genes are located within the at least one modular sub-network.

4. The method of claim 2, wherein each gene co-expression module of the set of gene co-expression modules is identified based on path length of the subset of the plurality of vertex data structures to at least one known disease gene.

5. The method of claim 2, wherein the generating a co-expression network step further comprises the steps of:
obtaining a second set of genetic data, wherein the second set of genetic data identifies genes and gene expression associated with the genes using the computing device;
querying the second set of genetic data using the set of terms of interest to retrieve a subset of the second set of genetic data associated with the terms of interest using the computing device using the computing device;
performing data combination and normalization on the second set of genetic data to produce a second set of normalized genetic data using the computing device;
generating a second gene co-expression network using the second set of normalized genetic data using the computing device, wherein:
the second gene co-expression network graph comprises a plurality of vertices and a plurality of edges;
each of the plurality of edges represents a link between two of the plurality of vertices;
the plurality of vertices contain data representing genes; and
the plurality of edges comprise a length value representing the degree of connection strength between two vertices that the edge links;
identifying a second set of gene co-expression modules within the second gene co-expression network based upon agglomerative hierarchical clustering using the computing device, wherein each gene co-expression module of the second set of gene co-expression modules comprises a subset of the plurality of vertices containing data predicted to describe a plurality of trait-associated genes; and
determining reproducibility of each gene co-expression module in the set of gene co-expression modules by calculating intramodular connectivity preservation between each gene in each gene co-expression module in the set of gene co-expression modules and the same gene in each gene co-expression module in the second set of gene co-expression modules using the computing device, wherein the reproducibility indicates module preservation.

6. The method of claim 5, wherein the second set of genetic data comprises microarray data from diseased model system tissues.

7. The method of claim 1, wherein the first set of genetic data comprises microarray data from fetal model system tissues.

8. The method of claim 1, wherein the first set of genetic data comprises genome wide genotyping data.

9. The method of claim 1, wherein the gene specific diagnostic platform is selected from the group consisting of a capture-based sequencing and hybridization-based genotyping platform.

10. A system for generating a gene specific diagnostic platform comprising:
a processor; and
a memory connected to the processor and storing an application, wherein the application directs the processor to:
obtain a first set of genetic data, wherein the first set of genetic data identifies genes and gene expression associated with the genes;
generate a co-expression network of the set of gene expression data, wherein the co-expression network identifies a set of modules of genes with similar patterns of gene expression;
obtain a set of known disease associated genes;
identify at least one module from the set of modules associated with at least one known disease associated gene from the set of known disease associated genes;
obtain a set of genetic variants, wherein the set of genetic variants identifies known genetic variants associated with genes;
identify at least one gene from the set of genetic variants associated with the at least one module associated with at least one known disease associated gene; and
create a gene specific diagnostic platform based on the at least one gene within the at least one module associated with the at least one known disease associated gene, wherein the gene specific diagnostic platform is used for molecular diagnosis of an individual for inherited disease syndromes.

11. The system of claim 10, wherein the generation of the first gene co-expression network is accomplished by the application directing the processor to:
query the first set of genetic data using a set of terms of interest to retrieve a subset of the first set of genetic data associated with the terms of interest;
perform data combination and normalization on the subset of the first set of genetic data to produce a set of normalized genetic data;
generate a first gene co-expression network using the set of normalized genetic data, wherein:
the gene co-expression network comprises a plurality of vertices and a plurality of edges;
each of the plurality of edges represents a link between two of the plurality of vertices;
the plurality of vertices contain data representing genes; and
the plurality of edges comprise a length value representing the degree of connection strength between two vertices that the edge links;
identify a set of gene co-expression modules within the first gene co-expression network based upon agglomerative hierarchical clustering, wherein each gene co-expression module of the set of gene co-expression modules comprises a subset of the plurality of vertices containing data predicted to describe a plurality of trait-associated genes.

12. The system of claim 11, wherein the application further directs the processor to identify the set of gene co-expression modules by:
generating at least one hierarchical cluster of edges of the first gene co-expression network graph data structure using the computing device; and identifying at least one modular sub-network from the at least one hierarchical cluster using the computing device, wherein the plurality of trait-associated genes are located within the at least one modular sub-network.

13. The system of claim 11, wherein each gene co-expression module of the set of gene co-expression modules is identified based on path length of the subset of the plurality of vertex data structures to at least one known disease gene.

14. The system of claim 11, wherein the generation of the first gene co-expression network is accomplished by the application further directing the processor to:
obtain a second set of genetic data, wherein the second set of genetic data identifies genes and gene expression associated with the genes;
querying the second set of genetic data using the set of terms of interest to retrieve a subset of the second set of genetic data associated with the terms of interest using the computing device;
perform data combination and normalization on the second set of genetic data to produce a second set of normalized genetic data;
generate a second gene co-expression network using the second set of normalized genetic data, wherein:
the second gene co-expression network graph comprises a plurality of vertices and a plurality of edges;
each of the plurality of edges represents a link between two of the plurality of vertices;
the plurality of vertices contain data representing genes; and
the plurality of edges comprise a length value representing the degree of connection strength between two vertices that the edge links;
identify a second set of gene co-expression modules within the second gene co-expression network based upon agglomerative hierarchical clustering, wherein each gene co-expression module of the second set of gene co-expression modules comprises a subset of the plurality of vertices containing data predicted to describe a plurality of trait-associated genes; and
determine reproducibility of each gene co-expression module from the set of gene co-expression modules by calculating intramodular connectivity preservation between each gene in each gene co-expression module in the set of gene co-expression modules and the same gene in each gene co-expression module in the second set of gene co-expression modules, wherein the reproducibility indicates module preservation.

15. The system of claim 14, wherein the second set of genetic data comprises microarray data from diseased model system tissues.

16. The system of claim 10, wherein the first set of genetic data comprises microarray data from fetal model system tissues.

17. The system of claim 10, wherein the first set of genetic data comprises data obtained from genome wide genotyping.

18. The system of claim 10, wherein the gene specific diagnostic platform is selected from the group consisting of a capture-based sequencing and hybridization-based genotyping platform.

19. A non-transitory machine-readable medium including instructions that, when executed by a processing unit, cause the processing unit to generate a gene specific diagnostic platform, the method performed using a computing device by performing the following operations:
obtaining a first set of genetic data, wherein the first set of genetic data identifies genes and gene expression associated with the genes;
generating a co-expression network of the set of gene expression data, wherein the co-expression network identifies a set of modules of genes with similar patterns of gene expression;
obtaining a set of known disease associated genes;
identifying at least one module from the set of modules associated with at least one known disease associated gene from the set of known disease associated genes;
obtaining a set of genetic variants, wherein the set of genetic variants identifies known genetic variants associated with genes;
identifying at least one gene from the set of genetic variants associated with the at least one module associated with at least one known disease associated gene; and
creating a gene specific diagnostic platform based on the at least one gene within the at least one module associated with the at least one known disease associated gene, wherein the gene specific diagnostic platform is used for molecular diagnosis of an individual for inherited disease syndromes.

20. The non-transitory machine-readable medium of claim 19, wherein the generating a co-expression network step comprises the steps of:
querying the first set of genetic data using a set of terms of interest to retrieve a subset of the first set of genetic data associated with the terms of interest using the computing device;
performing data combination and normalization on the subset of the first set of genetic data to produce a set of normalized genetic data;
generating a first gene co-expression network using the set of normalized genetic data, wherein:
the gene co-expression network comprises a plurality of vertices and a plurality of edges;
each of the plurality of edges represents a link between two of the plurality of vertices;
the plurality of vertices contain data representing genes; and
the plurality of edges comprise a length value representing the degree of connection strength between two vertices that the edge links;
identifying a set of gene co-expression modules within the first gene co-expression network based upon agglomerative hierarchical clustering, wherein each gene co-expression module of the set of gene co-expression modules comprises a subset of the plurality of vertices containing data predicted to describe a plurality of trait-associated genes.

21. The non-transitory machine-readable medium of claim 19, wherein the gene specific diagnostic platform is selected from the group consisting of a capture-based sequencing and hybridization-based genotyping platform.

* * * * *